US005837457A

United States Patent [19]
Liu et al.

[11] Patent Number: 5,837,457
[45] Date of Patent: Nov. 17, 1998

[54] MARKERS FOR DETECTION OF CHROMOSOME 16 REARRANGEMENTS

[75] Inventors: Pu Liu, Rockville; Francis S. Collins, Bethesda, both of Md.; Michael J. Siciliano; David Claxton, both of Houston, Tex.

[73] Assignees: The Regents of the University of Michigan, Ann Arbor, Mich.; The Board of Regents University of Texas System, Austin, Tex.

[21] Appl. No.: 533,306

[22] Filed: Sep. 25, 1995

Related U.S. Application Data

[63] Continuation of Ser. No. 99,869, Jul. 29, 1993, abandoned.
[51] Int. Cl.$^6$ .................................................. H04N 1/32
[52] U.S. Cl. ............................... 435/6; 435/91.2; 436/63; 436/64; 536/23.5; 536/24.31; 536/24.33; 935/6; 935/8; 935/9; 935/78
[58] Field of Search ..................... 435/6, 91.2; 436/64, 436/63; 536/23.5, 24.31, 24.33; 935/6, 8, 9, 11, 78

[56] References Cited

PUBLICATIONS

Arthur, D.C. et al., "Partial Deletion of the Long Arm of Chromosome 16 and Bone Marrow Eosinophilia in Acute Nonlymphocytic Leukemia: A New Associaion," *Blood* 61:995–998 (1983).

Babij, P. et al., "Myosin Heavy Chain Isoform Diversity in Smooth Muscle is Produced by Differential RNA Processing," *J. Mol. Biol.* 210:673–679 (1989).

Bae, S.C. et al., "Isolation of PEBPαB cDNA Representing the Mouse Homolog of Human Acute Myeloid Leukemia Gene, AML1," *Oncogene* 8:809–814 (1993).

Bennett, J.M. et al., "Proposed Revised Criteria for the Classification of Acute Myeloid Leukemia," *Ann. Intern. Med.* 103:626–629 (1985).

Borrow, A.D. et al., "Molecular Analsysis of Acute Promyelocytic Leukemia Breakpoint Cluster Region on Chromosome 17," *Science* 249:1577–1580 (1990).

Callen, D. F. et al., "Precise Localisation of the Long Arm Breakpoint of the Inv(6) of ANNL M4E0 and Progress Towards Closing this Breakpoint," *Am. J. Human Genet.* 51(4):A57 (1992).

Dauwerse, J.G. et al., "Extensive Cross–Homology Between the Long and the Short Arm of Chromosome 16 May Explain Leukemic Inversions and Translocations," *Blood* 79:1299–1304 (1992).

Deng, et al., "Smooth Muscle Myosin Heavy Chain Locus (MYH11) Maps to 16p13.13–p.13.12 and Establishes a New Region of Conserved Syntheny between Human 16p and Mouse 16," *Genomics* 18: 156–159 (1993).

Finger, L.R. et al., "A Common Mechanism of Chromosomal Translocation in T–and B–Cell Neoplasia," *Science* 234:982–985 (1986).

Kamachi, Y. et al., "Purification of a Mouse Nuclear Factor That Binds to both the A and B Cores of the Polyomarvius Enhancer," *J. Virol.* 64:4808–4819 (1990).

Kania, M.A. et al., "The Drosophilia Segmentation Gene Runt Encodes a Novel Nuclear Regulatory Protein that is also Expressed in the Developing Nervous System," *Genes Dev.* 4:1701–1713 (1990).

Kiehart, D.P., "Molecular Genetic Dissection of Myosin Heavy Chain Function," *Cell* 60:347–350 (1990).

(List continued on next page.)

*Primary Examiner*—Carla J. Myers
*Attorney, Agent, or Firm*—Harness, Dickey & Pierce, P.L.C.

[57] ABSTRACT

The breakpoints of the pericentric inversion of chromosome 16 have been cloned. Two genes, one at each breakpoint, have also been identified, as well as several forms of the inversion 16 fusion gene. Diagnostic applications for chromosome 16 abnormalities and, particularly acute myeloid leukemia are also within the scope of the present invention.

35 Claims, 11 Drawing Sheets

Normal 16

Inv 16

OTHER PUBLICATIONS

Le Beau, M.M. et al., "Association of an Inversion of Chromosome 16 with Abnormal Marrow Eosinophils in Acute Myelomoncytic Leukemia," *N. Engl. J. Med.* 309:630–636 (1983).

Liu, P. et al., "Identification of Yeast Artificial Chromosomes Containing the Inversion 16 p–Arm Breakpoint Associated with Acute Myelomoncytic Leukemia," *Blood* 82:716–721 (1993).

Liu, P. et al., "Efficiency and Limitations of the hn–cDNA Library Approach for the Isolation of Human Transcribed Genes from Hybrid Cells," *Somat. Cell Mol. Genet.* 18:7–18 (1992).

Liu, P. et al., P. et al., "Dual Alu Polymerase Chain Reaction Primers and Conditions of Isolation of Human Chromosome Painting Probes from Hybrid Cells." Can. Genet. Cytogen. 65:93–99 (1993).

Matsuoka, R. et al., "Human Smooth Muscle Myosin Heavy Chain Gene Mapped to Chromosomal Region 16q12," *Am. J. Med. Genet.* 46:61–67 (1993).

Nagai, R. et al., "Characterization of a Mammalian Smooth Muscle Myosin Heavy Chain cDNA Clone and its Expression in Various Smooth Muscle Types." *PNAS (USA)* 85:1047–1051 (1988).

Nagai, R. et al., "Identification of Two Types of Smooth Muscle Myosin Heavy Chain Isoforms by cDNA Cloning and Immunoblot Analysis," *J. Biol. Chem.* 264:9734–9737 (1989).

Ogawa, E. et al., "PEBP2/PEA2 Represents a Family of Transcription Factors Homologous to the Products of the Drosophjila Runt Gene and the Human AML1 Gene," PNAS (USA). 90:6859–6863 (1993).

Ogawa, E. et al., "Molecular Cloning and Characterization of PEBP2β, the Heterodimeric Partner of a Novel *Drosophila* Runt–Related DNA Binding Protein PEBP2α," *Virology* 194:314–331 (1993).

Redondo, J.M. et al., "Indistinguishable Nuclear Factor Binding to Functional Core Sites of the T–Cell Receptor δ and Murine Leukemia Virus Enhancers," *Mol. Cell. Biol.* 12:4817–4823 (1992).

Speck, N.A. et al., "Six Distinct Nuclear Factors Interact with the 75–Base–Pair Repeat of the Moloney Leukemia Virus Enhancer," *Mol. Cell. Biol.* 7:1101–1110 (1987).

Speck, N.A. et al., "Mutation of the Core or Adjacent LVb Elements of the Moloney Murine Leukemia Virus Enhancer Alters Disease Specificity," *Genes Dev.* 4:233–242 (1990).

Wang, S. et al., "Purification of Core–Binding Factor, a Protein that Binds the Conserved Core Site in Murine Leukemia Virus Enhancers," *Mol. Cell. Biol.* 12:89–102 (1992).

Wang, S. et al., "Cloning and Characterization of Subunits of the T–Cell Receptor and Murine Leukemia Virus Enhancers Core–Binding Factor," *Mol. Cell. Biol.* 13:3324–3339 (1993).

Wessels, J.W. et al., "Two Distinct Loci on the Short Arm of Chromosome 16 are Involved in Myeloid Leukemia," *Blood* 77:1555–1559 (1991).

Yanagisawa, M. et al., "Complete Primary Structure of Vertebrate Smooth Muscle Myosin Heary Chain Deduced from its Complementary DNA Sequence," *J. Mol. Biol.* 198:143–157 (1987).

Yanagisawa, K. et al., "Established and Characterization of a New Human Leukemia Cell Line Derived from $M_4E_0$," *Blood* 78:451 (1991).

Caller et al, Am J Human Genetics, Oct. 1992, vol. 51, No. 4, A57, Abstract #217.

Wang et al, Molec Cell Biol (Jun. 1993) 13:3324–3339.

Nagai et al, The J Biol Chem (1989) 264:9734–9737.

Matsuoka et al American J Med Genetics (Apr. 1993) 46:61–67.

Ogawa et al. *Virology* (1993) 194:314–331.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1960 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens
        ( C ) INDIVIDUAL ISOLATE: Samples 3- 6
        ( F ) TISSUE TYPE: Acute myelomonocytic leukemia, M4Eo
            subtype (inv16)

( v i i i ) POSITION IN GENOME:
        ( A ) CHROMOSOME/SEGMENT: 16[inv(16)(p13q22)]

( i x ) FEATURE:
        ( A ) NAME/KEY: CDS
        ( B ) LOCATION: 1..1731

( x ) PUBLICATION INFORMATION:
        ( A ) AUTHORS: Liu, Pu
            Tarle, Susan A.
            Hajra, Amitav Claxton, David F.
Marlton, Paula
Freedman, Matthew
Siciliano, Michael J.
Collins, Francis S.
(B) TITLE: Fusion between transcription factor
CBFB/PEBP2B and a myosin heavy chain in acute
myelomonocytic leukemia
(C) JOURNAL: Science
(G) DATE: August 1-1993
(K) RELEVANT RESIDUES IN SEQ ID NO:1: FROM 451 TO 534

(x) PUBLICATION INFORMATION:
(A) AUTHORS: Liu, Pu
Claxton, David F.
Marlton, Paula
Hajra, Jeanette
Freedman, Matthew
Chandrasekharappa, Settara C.
Yanagisawa, Kohsuke
Stallings, Raymond L.
Collins, Francis S.
Siciliano, Michael J.
(B) TITLE: Identification of yeast artificial
chromosomes containing the inversion 16 p-arm
breakpoint associated with acute myelomonocytic
leukemia
(C) JOURNAL: Blood
(G) DATE: 1993

(xi) SEQUENCE DESCRIPTION: SEQ ID NO:1:

| CCG | CGC | GTC | GTG | CCC | GAC | CAG | AGA | AGC | AAG | TTC | GAG | AAC | GAG | GAG | TTT | 48 |
| Pro | Arg | Val | Val | Pro | Asp | Gln | Arg | Ser | Lys | Phe | Glu | Asn | Glu | Glu | Phe | |
| 1 | | | | 5 | | | | | 10 | | | | | 15 | | |

| TTT | AGG | AAG | CTG | AGC | CGC | GAG | TGT | GAG | ATT | AAG | TAC | ACG | GGC | TTC | AGG | 96 |
| Phe | Arg | Lys | Leu | Ser | Arg | Glu | Cys | Glu | Ile | Lys | Tyr | Thr | Gly | Phe | Arg | |
| | | | 20 | | | | 25 | | | | | 30 | | | | |

| GAC | CGG | CCC | CAC | GAG | GAA | CGC | CAG | GCA | CGC | TTC | CAG | AAC | GCC | TGC | CGC | 144 |
| Asp | Arg | Pro | His | Glu | Glu | Arg | Gln | Ala | Arg | Phe | Gln | Asn | Ala | Cys | Arg | |
| | | 35 | | | | 40 | | | | | 45 | | | | | |

| GAC | GGC | CGC | TCG | GAA | ATC | GCT | TTT | GTG | GCC | ACA | GGA | ACC | AAT | CTG | TCT | 192 |
| Asp | Gly | Arg | Ser | Glu | Ile | Ala | Phe | Val | Ala | Thr | Gly | Thr | Asn | Leu | Ser | |
| | 50 | | | | 55 | | | | | 60 | | | | | | |

| CTC | CAA | TTT | TTT | CCG | GCC | AGC | TGG | CAG | GGA | GAA | CAG | CGA | CAA | ACA | CCT | 240 |
| Leu | Gln | Phe | Phe | Pro | Ala | Ser | Trp | Gln | Gly | Glu | Gln | Arg | Gln | Thr | Pro | |
| 65 | | | | 70 | | | | | 75 | | | | | 80 | | |

| AGC | CGA | GAG | TAT | GTC | GAC | TTA | GAA | AGA | GAA | GCA | GGC | AAG | GTA | TAT | TTG | 288 |
| Ser | Arg | Glu | Tyr | Val | Asp | Leu | Glu | Arg | Glu | Ala | Gly | Lys | Val | Tyr | Leu | |
| | | | | 85 | | | | | 90 | | | | | 95 | | |

| AAG | GCT | CCC | ATG | ATT | CTG | AAT | GGA | GTC | TGT | GTT | ATC | TGG | AAA | GGC | TGG | 336 |
| Lys | Ala | Pro | Met | Ile | Leu | Asn | Gly | Val | Cys | Val | Ile | Trp | Lys | Gly | Trp | |
| | | | 100 | | | | | 105 | | | | | 110 | | | |

| ATT | GAT | CTC | CAA | AGA | CTG | GAT | GGT | ATG | GGC | TGT | CTG | GAG | TTT | GAT | GAG | 384 |
| Ile | Asp | Leu | Gln | Arg | Leu | Asp | Gly | Met | Gly | Cys | Leu | Glu | Phe | Asp | Glu | |
| | | | 115 | | | | | 120 | | | | | 125 | | | |

| GAG | CGA | GCC | CAG | CAG | GAG | GAT | GCA | TTA | GCA | CAA | CAG | GCC | TTT | GAA | GAG | 432 |
| Glu | Arg | Ala | Gln | Gln | Glu | Asp | Ala | Leu | Ala | Gln | Gln | Ala | Phe | Glu | Glu | |
| | 130 | | | | | 135 | | | | | 140 | | | | | |

| GCT | CGG | AGA | AGG | ACA | CGC | GAA | TTT | GAA | GAT | AGA | GAC | AGG | TCT | CAT | CGG | 480 |
| Ala | Arg | Arg | Arg | Thr | Arg | Glu | Phe | Glu | Asp | Arg | Asp | Arg | Ser | His | Arg | |
| 145 | | | | | 150 | | | | | 155 | | | | | 160 | |

| GAG | GAA | ATG | GAG | GTC | CAT | GAG | CTG | GAG | AAG | TCC | AAG | CGG | GCC | CTG | GAG | 528 |
| Glu | Glu | Met | Glu | Val | His | Glu | Leu | Glu | Lys | Ser | Lys | Arg | Ala | Leu | Glu | |
| | | | | 165 | | | | | 170 | | | | | 175 | | |

| ACC | CAG | ATG | GAG | GAG | ATG | AAG | ACG | CAG | CTG | GAA | GAG | CTG | GAG | GAC | GAG | 576 |
| Thr | Gln | Met | Glu | Glu | Met | Lys | Thr | Gln | Leu | Glu | Glu | Leu | Glu | Asp | Glu | |
| | | 180 | | | | | 185 | | | | | 190 | | | | |

| | | | | | | | | | | | | | | | | |
|---|---|---|---|---|---|---|---|---|---|---|---|---|---|---|---|---|
| CTG | CAA | GCC | TCG | GAG | GAC | GCC | AAA | CTG | CGG | CTG | GAA | GTC | AAC | ATG | CAG | 624 |
| Leu | Gln | Ala | Ser | Glu | Asp | Ala | Lys | Leu | Arg | Leu | Glu | Val | Asn | Met | Gln | |
| | | | | 195 | | | | 200 | | | | 205 | | | | |
| GCG | CTC | AAG | GGC | CAG | TTC | GAA | AGG | GAT | CTC | CAA | GCC | CGG | GAC | GAG | CAG | 672 |
| Ala | Leu | Lys | Gly | Gln | Phe | Glu | Arg | Asp | Leu | Gln | Ala | Arg | Asp | Glu | Gln | |
| | 210 | | | | 215 | | | | | 220 | | | | | | |
| AAT | GAG | GAG | AAG | AGG | AGG | CAA | CTG | CAG | AGA | CAG | CTT | CAC | GAG | TAT | GAG | 720 |
| Asn | Glu | Glu | Lys | Arg | Arg | Gln | Leu | Gln | Arg | Gln | Leu | His | Glu | Tyr | Glu | |
| 225 | | | | | 230 | | | | | 235 | | | | | 240 | |
| ACG | GAA | CTG | GAA | GAC | GAG | CGA | AAC | GAA | CGT | GCC | CTG | GCA | GCT | GCA | GCA | 768 |
| Thr | Glu | Leu | Glu | Asp | Glu | Arg | Asn | Glu | Arg | Ala | Leu | Ala | Ala | Ala | Ala | |
| | | | | 245 | | | | | 250 | | | | | 255 | | |
| AAG | AAG | AAG | CTG | GAA | GGG | GAC | CTG | AAA | GAC | CTG | GAG | CTT | CAG | GCC | GAC | 816 |
| Lys | Lys | Lys | Leu | Glu | Gly | Asp | Leu | Lys | Asp | Leu | Glu | Leu | Gln | Ala | Asp | |
| | | | 260 | | | | | 265 | | | | | 270 | | | |
| TCT | GCC | ATC | AAG | GGG | AGG | GAG | GAA | GCC | ATC | AAG | CAG | CTA | CGC | AAA | CTG | 864 |
| Ser | Ala | Ile | Lys | Gly | Arg | Glu | Glu | Ala | Ile | Lys | Gln | Leu | Arg | Lys | Leu | |
| | | | 275 | | | | | 280 | | | | | 285 | | | |
| CAG | GCT | CAG | ATG | AAG | GAC | TTT | CAA | AGA | GAG | CTG | GAA | GAT | GCC | CGT | GCC | 912 |
| Gln | Ala | Gln | Met | Lys | Asp | Phe | Gln | Arg | Glu | Leu | Glu | Asp | Ala | Arg | Ala | |
| | 290 | | | | | 295 | | | | | 300 | | | | | |
| TCC | AGA | GAT | GAG | ATC | TTT | GCC | ACA | GCC | AAA | GAG | AAT | GAG | AAG | AAA | GCC | 960 |
| Ser | Arg | Asp | Glu | Ile | Phe | Ala | Thr | Ala | Lys | Glu | Asn | Glu | Lys | Lys | Ala | |
| 305 | | | | | 310 | | | | | 315 | | | | | 320 | |
| AAG | AGC | TTG | GAA | GCA | GAC | CTC | ATG | CAG | CTA | CAA | GAG | GAC | CTC | GCC | GCC | 1008 |
| Lys | Ser | Leu | Glu | Ala | Asp | Leu | Met | Gln | Leu | Gln | Glu | Asp | Leu | Ala | Ala | |
| | | | | 325 | | | | | 330 | | | | | 335 | | |
| GCT | GAG | AGG | GCT | CGC | AAA | CAA | GCG | GAC | CTC | GAG | AAG | GAG | GAA | CTG | GCA | 1056 |
| Ala | Glu | Arg | Ala | Arg | Lys | Gln | Ala | Asp | Leu | Glu | Lys | Glu | Glu | Leu | Ala | |
| | | | 340 | | | | | 345 | | | | | 350 | | | |
| GAG | GAG | CTG | GCC | AGT | AGC | CTG | TCG | GGA | AGG | AAC | GCA | CTC | CAG | GAC | GAG | 1104 |
| Glu | Glu | Leu | Ala | Ser | Ser | Leu | Ser | Gly | Arg | Asn | Ala | Leu | Gln | Asp | Glu | |
| | | 355 | | | | | 360 | | | | | 365 | | | | |
| AAG | CGC | CGC | CTG | GAG | GCC | CGG | ATC | GCC | CAG | CTG | GAG | GAG | GAG | CTG | GAG | 1152 |
| Lys | Arg | Arg | Leu | Glu | Ala | Arg | Ile | Ala | Gln | Leu | Glu | Glu | Glu | Leu | Glu | |
| | 370 | | | | | 375 | | | | | 380 | | | | | |
| GAG | GAG | CAG | GGC | AAC | ATG | GAG | GCC | ATG | AGC | GAC | CGG | GTC | CGC | AAA | GCC | 1200 |
| Glu | Glu | Gln | Gly | Asn | Met | Glu | Ala | Met | Ser | Asp | Arg | Val | Arg | Lys | Ala | |
| 385 | | | | | 390 | | | | | 395 | | | | | 400 | |
| ACA | CAG | CAG | GCC | GAG | CAG | CTC | AGC | AAC | GAG | CTG | GCC | ACA | GAG | CGC | AGC | 1248 |
| Thr | Gln | Gln | Ala | Glu | Gln | Leu | Ser | Asn | Glu | Leu | Ala | Thr | Glu | Arg | Ser | |
| | | | | 405 | | | | | 410 | | | | | 415 | | |
| ACG | GCC | CAG | AAG | AAT | GAG | AGT | GCC | CGG | CAG | CAG | CTC | GAG | CGG | CAG | AAC | 1296 |
| Thr | Ala | Gln | Lys | Asn | Glu | Ser | Ala | Arg | Gln | Gln | Leu | Glu | Arg | Gln | Asn | |
| | | | 420 | | | | | 425 | | | | | 430 | | | |
| AAG | GAG | CTC | CGG | AGC | AAG | CTC | CAC | GAG | ATG | GAG | GGG | GCC | GTC | AAG | TCC | 1344 |
| Lys | Glu | Leu | Arg | Ser | Lys | Leu | His | Glu | Met | Glu | Gly | Ala | Val | Lys | Ser | |
| | | 435 | | | | | 440 | | | | | 445 | | | | |
| AAG | TTC | AAG | TCC | ACC | ATC | GCG | GCG | CTG | GAG | GCC | AAG | ATT | GCA | CAG | CTG | 1392 |
| Lys | Phe | Lys | Ser | Thr | Ile | Ala | Ala | Leu | Glu | Ala | Lys | Ile | Ala | Gln | Leu | |
| | 450 | | | | 455 | | | | | 460 | | | | | | |
| GAG | GAG | CAG | GTC | GAG | CAG | GAG | GCC | AGA | GAG | AAA | CAG | GCA | GCC | ACC | AAG | 1440 |
| Glu | Glu | Gln | Val | Glu | Gln | Glu | Ala | Arg | Glu | Lys | Gln | Ala | Ala | Thr | Lys | |
| 465 | | | | | 470 | | | | | 475 | | | | | 480 | |
| TCG | CTG | AAG | CAG | AAA | GAC | AAG | AAG | CTG | AAG | GAA | ATC | TTG | CTG | CAG | GTG | 1488 |
| Ser | Leu | Lys | Gln | Lys | Asp | Lys | Lys | Leu | Lys | Glu | Ile | Leu | Leu | Gln | Val | |
| | | | | 485 | | | | | 490 | | | | | 495 | | |
| GAG | GAC | GAG | CGC | AAG | ATG | GCC | GAG | CAG | TAC | AAG | GAG | CAG | GCA | GAG | AAA | 1536 |
| Glu | Asp | Glu | Arg | Lys | Met | Ala | Glu | Gln | Tyr | Lys | Glu | Gln | Ala | Glu | Lys | |
| | | | 500 | | | | | 505 | | | | | 510 | | | |

-continued

| | | | | | | | | | | | | | | | | |
|---|---|---|---|---|---|---|---|---|---|---|---|---|---|---|---|---|
| GGC | AAT | GCC | AGG | GTC | AAG | CAG | CTC | AAG | AGG | CAG | CTG | GAG | GAG | GCA | GAG | 1584 |
| Gly | Asn | Ala | Arg | Val | Lys | Gln | Leu | Lys | Arg | Gln | Leu | Glu | Glu | Ala | Glu | |
| | | 515 | | | | 520 | | | | | 525 | | | | | |
| GAG | GAG | TCC | CAG | CGC | ATC | AAC | GCC | AAC | CGC | AGG | AAG | CTG | CAG | CGG | GAG | 1632 |
| Glu | Glu | Ser | Gln | Arg | Ile | Asn | Ala | Asn | Arg | Arg | Lys | Leu | Gln | Arg | Glu | |
| | 530 | | | | | 535 | | | | | 540 | | | | | |
| CTG | GAT | GAG | GCC | ACG | GAG | AGC | AAC | GAG | GCC | ATG | GGC | CGT | GAG | GTG | AAC | 1680 |
| Leu | Asp | Glu | Ala | Thr | Glu | Ser | Asn | Glu | Ala | Met | Gly | Arg | Glu | Val | Asn | |
| 545 | | | | 550 | | | | | 555 | | | | | 560 | | |
| GCA | CTC | AAG | AGC | AAG | CTC | AGA | GGG | CCC | CCC | CCA | CAG | GAA | ACT | TCG | CAG | 1728 |
| Ala | Leu | Lys | Ser | Lys | Leu | Arg | Gly | Pro | Pro | Pro | Gln | Glu | Thr | Ser | Gln | |
| | | | | 565 | | | | | 570 | | | | | 575 | | |

| | | | | |
|---|---|---|---|---|
| TGATGCACCA | GGCGAGGAAA | CGAGACCTCT | TTCGTTCCTT | CTAGAAGGTC | TGGAGGACGT | 1788 |
| AGAGTTATTG | AAAATGCAGA | TGGTTCTGAG | GAGGAACTGG | ACACTCGAGA | CGCAGACTTC | 1848 |
| AATGGAACCA | AGGCCAGTGA | ATAAGCAACT | TTCTACAGTT | TTGCACCACG | GCAAGAAAAC | 1908 |
| CAAAACCAA | AACAAACAAA | CAAAAAAAAC | CCAACAACAA | CCCGAACAAG | AC | 1960 |

(2) INFORMATION FOR SEQ ID NO:2:

(i) SEQUENCE CHARACTERISTICS:
        (A) LENGTH: 576 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Pro | Arg | Val | Val | Pro | Asp | Gln | Arg | Ser | Lys | Phe | Glu | Asn | Glu | Phe |
| 1 | | | | 5 | | | | | 10 | | | | | 15 |
| Phe | Arg | Lys | Leu | Ser | Arg | Glu | Cys | Glu | Ile | Lys | Tyr | Thr | Gly | Phe | Arg |
| | | | 20 | | | | | 25 | | | | | 30 | |
| Asp | Arg | Pro | His | Glu | Glu | Arg | Gln | Ala | Arg | Phe | Gln | Asn | Ala | Cys | Arg |
| | | | 35 | | | | | 40 | | | | | 45 | |
| Asp | Gly | Arg | Ser | Glu | Ile | Ala | Phe | Val | Ala | Thr | Gly | Thr | Asn | Leu | Ser |
| | | 50 | | | | | 55 | | | | | 60 | | |
| Leu | Gln | Phe | Phe | Pro | Ala | Ser | Trp | Gln | Gly | Glu | Gln | Arg | Gln | Thr | Pro |
| 65 | | | | | 70 | | | | | 75 | | | | | 80 |
| Ser | Arg | Glu | Tyr | Val | Asp | Leu | Glu | Arg | Glu | Ala | Gly | Lys | Val | Tyr | Leu |
| | | | | 85 | | | | | 90 | | | | | 95 | |
| Lys | Ala | Pro | Met | Ile | Leu | Asn | Gly | Val | Cys | Val | Ile | Trp | Lys | Gly | Trp |
| | | | | 100 | | | | | 105 | | | | | 110 | |
| Ile | Asp | Leu | Gln | Arg | Leu | Asp | Gly | Met | Gly | Cys | Leu | Glu | Phe | Asp | Glu |
| | | | 115 | | | | | 120 | | | | | 125 | | |
| Glu | Arg | Ala | Gln | Gln | Glu | Asp | Ala | Leu | Ala | Gln | Gln | Ala | Phe | Glu | Glu |
| | | 130 | | | | | 135 | | | | | 140 | | | |
| Ala | Arg | Arg | Arg | Thr | Arg | Glu | Phe | Glu | Asp | Arg | Asp | Arg | Ser | His | Arg |
| 145 | | | | | 150 | | | | | 155 | | | | | 160 |
| Glu | Glu | Met | Glu | Val | His | Glu | Leu | Glu | Lys | Ser | Lys | Arg | Ala | Leu | Glu |
| | | | | 165 | | | | | 170 | | | | | 175 | |
| Thr | Gln | Met | Glu | Glu | Met | Lys | Thr | Gln | Leu | Glu | Leu | Glu | Leu | Asp | Glu |
| | | | 180 | | | | | 185 | | | | | 190 | | |
| Leu | Gln | Ala | Ser | Glu | Asp | Ala | Lys | Leu | Arg | Leu | Glu | Val | Asn | Met | Gln |
| | | | 195 | | | | | 200 | | | | | 205 | | |
| Ala | Leu | Lys | Gly | Gln | Phe | Glu | Arg | Asp | Leu | Gln | Ala | Arg | Asp | Glu | Gln |
| | | 210 | | | | | 215 | | | | | 220 | | | |
| Asn | Glu | Glu | Lys | Arg | Arg | Gln | Leu | Gln | Arg | Gln | Leu | His | Glu | Tyr | Glu |
| 225 | | | | | 230 | | | | | 235 | | | | | 240 |

| Thr | Glu | Leu | Glu | Asp | Glu | Arg | Asn | Glu | Arg | Ala | Leu | Ala | Ala | Ala | Ala |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |
| Lys | Lys | Lys | Leu | Glu | Gly | Asp | Leu | Lys | Asp | Leu | Glu | Leu | Gln | Ala | Asp |
|     |     |     | 260 |     |     |     | 265 |     |     |     |     | 270 |     |     |     |
| Ser | Ala | Ile | Lys | Gly | Arg | Glu | Glu | Ala | Ile | Lys | Gln | Leu | Arg | Lys | Leu |
|     |     | 275 |     |     |     | 280 |     |     |     |     | 285 |     |     |     |     |
| Gln | Ala | Gln | Met | Lys | Asp | Phe | Gln | Arg | Glu | Leu | Glu | Asp | Ala | Arg | Ala |
|     | 290 |     |     |     |     | 295 |     |     |     |     | 300 |     |     |     |     |
| Ser | Arg | Asp | Glu | Ile | Phe | Ala | Thr | Ala | Lys | Glu | Asn | Glu | Lys | Lys | Ala |
| 305 |     |     |     |     | 310 |     |     |     |     | 315 |     |     |     |     | 320 |
| Lys | Ser | Leu | Glu | Ala | Asp | Leu | Met | Gln | Leu | Gln | Glu | Asp | Leu | Ala | Ala |
|     |     |     |     | 325 |     |     |     |     | 330 |     |     |     |     | 335 |     |
| Ala | Glu | Arg | Ala | Arg | Lys | Gln | Ala | Asp | Leu | Glu | Lys | Glu | Glu | Leu | Ala |
|     |     |     | 340 |     |     |     |     | 345 |     |     |     |     | 350 |     |     |
| Glu | Glu | Leu | Ala | Ser | Ser | Leu | Ser | Gly | Arg | Asn | Ala | Leu | Gln | Asp | Glu |
|     |     |     | 355 |     |     |     |     | 360 |     |     |     | 365 |     |     |     |
| Lys | Arg | Arg | Leu | Glu | Ala | Arg | Ile | Ala | Gln | Leu | Glu | Glu | Glu | Leu | Glu |
|     |     | 370 |     |     |     |     | 375 |     |     |     |     | 380 |     |     |     |
| Glu | Glu | Gln | Gly | Asn | Met | Glu | Ala | Met | Ser | Asp | Arg | Val | Arg | Lys | Ala |
| 385 |     |     |     |     | 390 |     |     |     |     | 395 |     |     |     |     | 400 |
| Thr | Gln | Gln | Ala | Glu | Gln | Leu | Ser | Asn | Glu | Leu | Ala | Thr | Glu | Arg | Ser |
|     |     |     |     | 405 |     |     |     |     | 410 |     |     |     |     | 415 |     |
| Thr | Ala | Gln | Lys | Asn | Glu | Ser | Ala | Arg | Gln | Gln | Leu | Glu | Arg | Gln | Asn |
|     |     |     | 420 |     |     |     |     | 425 |     |     |     |     | 430 |     |     |
| Lys | Glu | Leu | Arg | Ser | Lys | Leu | His | Glu | Met | Glu | Gly | Ala | Val | Lys | Ser |
|     |     |     | 435 |     |     |     | 440 |     |     |     |     | 445 |     |     |     |
| Lys | Phe | Lys | Ser | Thr | Ile | Ala | Ala | Leu | Glu | Ala | Lys | Ile | Ala | Gln | Leu |
|     | 450 |     |     |     |     | 455 |     |     |     |     | 460 |     |     |     |     |
| Glu | Glu | Gln | Val | Glu | Gln | Glu | Ala | Arg | Glu | Lys | Gln | Ala | Ala | Thr | Lys |
| 465 |     |     |     |     | 470 |     |     |     |     | 475 |     |     |     |     | 480 |
| Ser | Leu | Lys | Gln | Lys | Asp | Lys | Lys | Leu | Lys | Glu | Ile | Leu | Leu | Gln | Val |
|     |     |     |     | 485 |     |     |     |     | 490 |     |     |     |     | 495 |     |
| Glu | Asp | Glu | Arg | Lys | Met | Ala | Glu | Gln | Tyr | Lys | Glu | Gln | Ala | Glu | Lys |
|     |     |     | 500 |     |     |     |     | 505 |     |     |     |     | 510 |     |     |
| Gly | Asn | Ala | Arg | Val | Lys | Gln | Leu | Lys | Arg | Gln | Leu | Glu | Glu | Ala | Glu |
|     |     | 515 |     |     |     |     | 520 |     |     |     |     | 525 |     |     |     |
| Glu | Glu | Ser | Gln | Arg | Ile | Asn | Ala | Asn | Arg | Arg | Lys | Leu | Gln | Arg | Glu |
|     |     | 530 |     |     |     |     | 535 |     |     |     | 540 |     |     |     |     |
| Leu | Asp | Glu | Ala | Thr | Glu | Ser | Asn | Glu | Ala | Met | Gly | Arg | Glu | Val | Asn |
| 545 |     |     |     |     | 550 |     |     |     |     | 555 |     |     |     |     | 560 |
| Ala | Leu | Lys | Ser | Lys | Leu | Arg | Gly | Pro | Pro | Pro | Gln | Glu | Thr | Ser | Gln |
|     |     |     |     | 565 |     |     |     | 570 |     |     |     |     | 575 |     |     |

( 2 ) INFORMATION FOR SEQ ID NO:3:

( i ) SEQUENCE CHARACTERISTICS:
        ( A ) LENGTH: 2887 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:

(A) ORGANISM: Homo sapiens
(C) INDIVIDUAL ISOLATE: Sample 1
(F) TISSUE TYPE: Acute myelomonocytic leukemia, M4Eo subtype (inv16)

(viii) POSITION IN GENOME:
(A) CHROMOSOME/SEGMENT: 16[inv(16)(p13q22)]

(ix) FEATURE:
(A) NAME/KEY: CDS
(B) LOCATION: 1..2658

(xi) SEQUENCE DESCRIPTION: SEQ ID NO:3:

```
CCG  CGC  GTC  GTG  CCC  GAC  CAG  AGA  AGC  AAG  TTC  GAG  AAC  GAG  GAG  TTT      48
Pro  Arg  Val  Val  Pro  Asp  Gln  Arg  Ser  Lys  Phe  Glu  Asn  Glu  Glu  Phe
 1                    5                        10                       15

TTT  AGG  AAG  CTG  AGC  CGC  GAG  TGT  GAG  ATT  AAG  TAC  ACG  GGC  TTC  AGG      96
Phe  Arg  Lys  Leu  Ser  Arg  Glu  Cys  Glu  Ile  Lys  Tyr  Thr  Gly  Phe  Arg
          20                             25                       30

GAC  CGG  CCC  CAC  GAG  GAA  CGC  CAG  GCA  CGC  TTC  CAG  AAC  GCC  TGC  CGC     144
Asp  Arg  Pro  His  Glu  Glu  Arg  Gln  Ala  Arg  Phe  Gln  Asn  Ala  Cys  Arg
               35                    40                       45

GAC  GGC  CGC  TCG  GAA  ATC  GCT  TTT  GTG  GCC  ACA  GGA  ACC  AAT  CTG  TCT     192
Asp  Gly  Arg  Ser  Glu  Ile  Ala  Phe  Val  Ala  Thr  Gly  Thr  Asn  Leu  Ser
          50                    55                       60

CTC  CAA  TTT  TTT  CCG  GCC  AGC  TGG  CAG  GGA  GAA  CAG  CGA  CAA  ACA  CCT     240
Leu  Gln  Phe  Phe  Pro  Ala  Ser  Trp  Gln  Gly  Glu  Gln  Arg  Gln  Thr  Pro
 65                    70                       75                       80

AGC  CGA  GAG  TAT  GTC  GAC  TTA  GAA  AGA  GAA  GCA  GGC  AAG  GTA  TAT  TTG     288
Ser  Arg  Glu  Tyr  Val  Asp  Leu  Glu  Arg  Glu  Ala  Gly  Lys  Val  Tyr  Leu
                    85                        90                       95

AAG  GCT  CCC  ATG  ATT  CTG  AAT  GGA  GTC  TGT  GTT  ATC  TGG  AAA  GGC  TGG     336
Lys  Ala  Pro  Met  Ile  Leu  Asn  Gly  Val  Cys  Val  Ile  Trp  Lys  Gly  Trp
               100                        105                       110

ATT  GAT  CTC  CAA  AGA  CTG  GAT  GGT  ATG  GGC  TGT  CTG  GAG  TTT  GAT  GAG     384
Ile  Asp  Leu  Gln  Arg  Leu  Asp  Gly  Met  Gly  Cys  Leu  Glu  Phe  Asp  Glu
               115                        120                       125

GAG  CGA  GCC  CAG  CAG  GAG  GAT  GCA  TTA  GCA  CAA  CAG  GCC  TTT  GAA  GAG     432
Glu  Arg  Ala  Gln  Gln  Glu  Asp  Ala  Leu  Ala  Gln  Gln  Ala  Phe  Glu  Glu
     130                        135                       140

GCT  CGG  AGA  AGG  ACA  CGC  GAA  TTT  GAA  GAT  AGA  GAC  AGG  TCT  CAT  CGG     480
Ala  Arg  Arg  Arg  Thr  Arg  Glu  Phe  Glu  Asp  Arg  Asp  Arg  Ser  His  Arg
145                        150                       155                  160

GAG  GAA  ATG  GAG  GCC  AAG  GCG  AAC  CTA  GAC  AAG  AAT  AAG  CAG  ACG  CTG     528
Glu  Glu  Met  Glu  Ala  Lys  Ala  Asn  Leu  Asp  Lys  Asn  Lys  Gln  Thr  Leu
                         165                       170                  175

GAG  AAA  GAG  AAC  GCA  GAC  CTG  GCC  GGG  GAG  CTG  CGG  GTC  CTG  GGC  CAG     576
Glu  Lys  Glu  Asn  Ala  Asp  Leu  Ala  Gly  Glu  Leu  Arg  Val  Leu  Gly  Gln
               180                        185                       190

GCC  AAG  CAG  GAG  GTG  GAA  CAT  AAG  AAG  AAG  AAG  CTG  GAG  GCG  CAG  GTG     624
Ala  Lys  Gln  Glu  Val  Glu  His  Lys  Lys  Lys  Lys  Leu  Glu  Ala  Gln  Val
          195                        200                       205

CAG  GAG  CTG  CAG  TCC  AAG  TGC  AGC  GAT  GGG  GAG  CGG  GCC  CGG  GCG  GAG     672
Gln  Glu  Leu  Gln  Ser  Lys  Cys  Ser  Asp  Gly  Glu  Arg  Ala  Arg  Ala  Glu
     210                        215                       220

CTC  AAT  GAC  AAA  GTC  CAC  AAG  CTG  CAG  AAT  GAA  GTT  GAG  AGC  GTC  ACA     720
Leu  Asn  Asp  Lys  Val  His  Lys  Leu  Gln  Asn  Glu  Val  Glu  Ser  Val  Thr
225                        230                       235                  240

GGG  ATG  CTT  AAC  GAG  GCC  GAG  GGG  AAG  GCC  ATT  AAG  CTG  GCC  AAG  GAC     768
Gly  Met  Leu  Asn  Glu  Ala  Glu  Gly  Lys  Ala  Ile  Lys  Leu  Ala  Lys  Asp
                    245                        250                       255

GTG  GCG  TCC  CTC  AGT  TCC  CAG  CTC  CAG  GAC  ACC  CAG  GAG  TTG  CTT  CAA     816
Val  Ala  Ser  Leu  Ser  Ser  Gln  Leu  Gln  Asp  Thr  Gln  Glu  Leu  Leu  Gln
```

```
                      260                           265                           270
GAA  GAA  ACC  CGG  CAG  AAG  CTC  AAC  GTG  TCT  ACG  AAG  CTG  CGC  CAG  CTG            864
Glu  Glu  Thr  Arg  Gln  Lys  Leu  Asn  Val  Ser  Thr  Lys  Leu  Arg  Gln  Leu
          275                      280                      285

GAG  GAG  GAG  CGG  AAC  AGC  CTG  CAA  GAC  CAG  CTG  GAC  GAG  GAG  ATG  GAG            912
Glu  Glu  Glu  Arg  Asn  Ser  Leu  Gln  Asp  Gln  Leu  Asp  Glu  Glu  Met  Glu
          290                      295                      300

GCC  AAG  CAG  AAC  CTG  GAG  CGC  CAC  ATC  TCC  ACT  CTC  AAC  ATC  CAG  CTC            960
Ala  Lys  Gln  Asn  Leu  Glu  Arg  His  Ile  Ser  Thr  Leu  Asn  Ile  Gln  Leu
305                      310                      315                      320

TCC  GAC  TCG  AAG  AAG  AAG  CTG  CAG  GAC  TTT  GCC  AGC  ACC  GTG  GAA  GCT           1008
Ser  Asp  Ser  Lys  Lys  Lys  Leu  Gln  Asp  Phe  Ala  Ser  Thr  Val  Glu  Ala
                    325                      330                      335

CTG  GAA  GAG  GGG  AAG  AAG  AGG  TTC  CAG  AAG  GAG  ATC  GAG  AAC  CTC  ACC           1056
Leu  Glu  Glu  Gly  Lys  Lys  Arg  Phe  Gln  Lys  Glu  Ile  Glu  Asn  Leu  Thr
               340                      345                      350

CAG  CAG  TAC  GAG  GAG  AAG  GCG  GCC  GCT  TAT  GAT  AAA  CTG  GAA  AAG  ACC           1104
Gln  Gln  Tyr  Glu  Glu  Lys  Ala  Ala  Ala  Tyr  Asp  Lys  Leu  Glu  Lys  Thr
          355                      360                      365

AAG  AAC  AGG  CTT  CAG  CAG  GAG  CTG  GAC  GAC  CTG  GTT  GTT  GAT  TTG  GAC           1152
Lys  Asn  Arg  Leu  Gln  Gln  Glu  Leu  Asp  Asp  Leu  Val  Val  Asp  Leu  Asp
     370                      375                      380

AAC  CAG  CGG  CAA  CTC  GTG  TCC  AAC  CTG  GAA  AAG  AAG  CAG  AGG  AAA  TTT           1200
Asn  Gln  Arg  Gln  Leu  Val  Ser  Asn  Leu  Glu  Lys  Lys  Gln  Arg  Lys  Phe
385                      390                      395                      400

GAT  CAG  TTG  TTA  GCC  GAG  GAG  AAA  AAC  ATC  TCT  TCC  AAA  TAC  GCG  GAT           1248
Asp  Gln  Leu  Leu  Ala  Glu  Glu  Lys  Asn  Ile  Ser  Ser  Lys  Tyr  Ala  Asp
                    405                      410                      415

GAG  AGG  GAC  AGA  GCT  GAG  GCA  GAA  GCC  AGG  GAG  AAG  GAA  ACC  AAG  GCC           1296
Glu  Arg  Asp  Arg  Ala  Glu  Ala  Glu  Ala  Arg  Glu  Lys  Glu  Thr  Lys  Ala
               420                      425                      430

CTG  TCC  CTG  GCT  CGG  GCC  CTT  GAA  GAG  GCC  TTG  GAA  GCC  AAA  GAG  GAA           1344
Leu  Ser  Leu  Ala  Arg  Ala  Leu  Glu  Glu  Ala  Leu  Glu  Ala  Lys  Glu  Glu
          435                      440                      445

CTC  GAG  CGG  ACC  AAC  AAA  ATG  CTC  AAA  GCC  GAA  ATG  GAA  GAC  CTG  GTC           1392
Leu  Glu  Arg  Thr  Asn  Lys  Met  Leu  Lys  Ala  Glu  Met  Glu  Asp  Leu  Val
     450                      455                      460

AGC  TCC  AAG  GAT  GAC  GTG  GGC  AAG  AAC  GTC  CAT  GAG  CTG  GAG  AAG  TCC           1440
Ser  Ser  Lys  Asp  Asp  Val  Gly  Lys  Asn  Val  His  Glu  Leu  Glu  Lys  Ser
465                      470                      475                      480

AAG  CGG  GCC  CTG  GAG  ACC  CAG  ATG  GAG  GAG  ATG  AAG  ACG  CAG  CTG  GAA           1488
Lys  Arg  Ala  Leu  Glu  Thr  Gln  Met  Glu  Glu  Met  Lys  Thr  Gln  Leu  Glu
                    485                      490                      495

GAG  CTG  GAG  GAC  GAG  CTG  CAA  GCC  TCG  GAG  GAC  GCC  AAA  CTG  CGG  CTG           1536
Glu  Leu  Glu  Asp  Glu  Leu  Gln  Ala  Ser  Glu  Asp  Ala  Lys  Leu  Arg  Leu
               500                      505                      510

GAA  GTC  AAC  ATG  CAG  GCG  CTC  AAG  GGC  CAG  TTC  GAA  AGG  GAT  CTC  CAA           1584
Glu  Val  Asn  Met  Gln  Ala  Leu  Lys  Gly  Gln  Phe  Glu  Arg  Asp  Leu  Gln
          515                      520                      525

GCC  CGG  GAC  GAG  CAG  AAT  GAG  GAG  AAG  AGG  AGG  CAA  CTG  CAG  AGA  CAG           1632
Ala  Arg  Asp  Glu  Gln  Asn  Glu  Glu  Lys  Arg  Arg  Gln  Leu  Gln  Arg  Gln
     530                      535                      540

CTT  CAC  GAG  TAT  GAG  ACG  GAA  CTG  GAA  GAC  GAG  CGA  AAC  GAA  CGT  GCC           1680
Leu  His  Glu  Tyr  Glu  Thr  Glu  Leu  Glu  Asp  Glu  Arg  Asn  Glu  Arg  Ala
545                      550                      555                      560

CTG  GCA  GCT  GCA  GCA  AAG  AAG  AAG  CTG  GAA  GGG  GAC  CTG  AAA  GAC  CTG           1728
Leu  Ala  Ala  Ala  Ala  Lys  Lys  Lys  Leu  Glu  Gly  Asp  Leu  Lys  Asp  Leu
                    565                      570                      575

GAG  CTT  CAG  GCC  GAC  TCT  GCC  ATC  AAG  GGG  AGG  GAG  GAA  GCC  ATC  AAG           1776
Glu  Leu  Gln  Ala  Asp  Ser  Ala  Ile  Lys  Gly  Arg  Glu  Glu  Ala  Ile  Lys
```

```
                      580                          585                          590
CAG  CTA  CGC  AAA  CTG  CAG  GCT  CAG  ATG  AAG  GAC  TTT  CAA  AGA  GAG  CTG       1824
Gln  Leu  Arg  Lys  Leu  Gln  Ala  Gln  Met  Lys  Asp  Phe  Gln  Arg  Glu  Leu
          595                      600                      605

GAA  GAT  GCC  CGT  GCC  TCC  AGA  GAT  GAG  ATC  TTT  GCC  ACA  GCC  AAA  GAG       1872
Glu  Asp  Ala  Arg  Ala  Ser  Arg  Asp  Glu  Ile  Phe  Ala  Thr  Ala  Lys  Glu
     610                      615                      620

AAT  GAG  AAG  AAA  GCC  AAG  AGC  TTG  GAA  GCA  GAC  CTC  ATG  CAG  CTA  CAA       1920
Asn  Glu  Lys  Lys  Ala  Lys  Ser  Leu  Glu  Ala  Asp  Leu  Met  Gln  Leu  Gln
625                      630                      635                      640

GAG  GAC  CTC  GCC  GCC  GCT  GAG  AGG  GCT  CGC  AAA  CAA  GCG  GAC  CTC  GAG       1968
Glu  Asp  Leu  Ala  Ala  Ala  Glu  Arg  Ala  Arg  Lys  Gln  Ala  Asp  Leu  Glu
               645                      650                      655

AAG  GAG  GAA  CTG  GCA  GAG  GAG  CTG  GCC  AGT  AGC  CTG  TCG  GGA  AGG  AAC       2016
Lys  Glu  Glu  Leu  Ala  Glu  Glu  Leu  Ala  Ser  Ser  Leu  Ser  Gly  Arg  Asn
                    660                      665                      670

GCA  CTC  CAG  GAC  GAG  AAG  CGC  CGC  CTG  GAG  GCC  CGG  ATC  GCC  CAG  CTG       2064
Ala  Leu  Gln  Asp  Glu  Lys  Arg  Arg  Leu  Glu  Ala  Arg  Ile  Ala  Gln  Leu
          675                      680                      685

GAG  GAG  GAG  CTG  GAG  GAG  GAG  CAG  GGC  AAC  ATG  GAG  GCC  ATG  AGC  GAC       2112
Glu  Glu  Glu  Leu  Glu  Glu  Glu  Gln  Gly  Asn  Met  Glu  Ala  Met  Ser  Asp
     690                      695                      700

CGG  GTC  CGC  AAA  GCC  ACA  CAG  CAG  GCC  GAG  CAG  CTC  AGC  AAC  GAG  CTG       2160
Arg  Val  Arg  Lys  Ala  Thr  Gln  Gln  Ala  Glu  Gln  Leu  Ser  Asn  Glu  Leu
705                      710                      715                      720

GCC  ACA  GAG  CGC  AGC  ACG  GCC  CAG  AAG  AAT  GAG  AGT  GCC  CGG  CAG  CAG       2208
Ala  Thr  Glu  Arg  Ser  Thr  Ala  Gln  Lys  Asn  Glu  Ser  Ala  Arg  Gln  Gln
               725                      730                      735

CTC  GAG  CGG  CAG  AAC  AAG  GAG  CTC  CGG  AGC  AAG  CTC  CAC  GAG  ATG  GAG       2256
Leu  Glu  Arg  Gln  Asn  Lys  Glu  Leu  Arg  Ser  Lys  Leu  His  Glu  Met  Glu
                    740                      745                      750

GGG  GCC  GTC  AAG  TCC  AAG  TTC  AAG  TCC  ACC  ATC  GCG  GCG  CTG  GAG  GCC       2304
Gly  Ala  Val  Lys  Ser  Lys  Phe  Lys  Ser  Thr  Ile  Ala  Ala  Leu  Glu  Ala
          755                      760                      765

AAG  ATT  GCA  CAG  CTG  GAG  GAG  CAG  GTC  GAG  CAG  GAG  GCC  AGA  GAG  AAA       2352
Lys  Ile  Ala  Gln  Leu  Glu  Glu  Gln  Val  Glu  Gln  Glu  Ala  Arg  Glu  Lys
     770                      775                      780

CAG  GCA  GCC  ACC  AAG  TCG  CTG  AAG  CAG  AAA  GAC  AAG  AAG  CTG  AAG  GAA       2400
Gln  Ala  Ala  Thr  Lys  Ser  Leu  Lys  Gln  Lys  Asp  Lys  Lys  Leu  Lys  Glu
785                      790                      795                      800

ATC  TTG  CTG  CAG  GTG  GAG  GAC  GAG  CGC  AAG  ATG  GCC  GAG  CAG  TAC  AAG       2448
Ile  Leu  Leu  Gln  Val  Glu  Asp  Glu  Arg  Lys  Met  Ala  Glu  Gln  Tyr  Lys
               805                      810                      815

GAG  CAG  GCA  GAG  AAA  GGC  AAT  GCC  AGG  GTC  AAG  CAG  CTC  AAG  AGG  CAG       2496
Glu  Gln  Ala  Glu  Lys  Gly  Asn  Ala  Arg  Val  Lys  Gln  Leu  Lys  Arg  Gln
                    820                      825                      830

CTG  GAG  GAG  GCA  GAG  GAG  GAG  TCC  CAG  CGC  ATC  AAC  GCC  AAC  CGC  AGG       2544
Leu  Glu  Glu  Ala  Glu  Glu  Glu  Ser  Gln  Arg  Ile  Asn  Ala  Asn  Arg  Arg
          835                      840                      845

AAG  CTG  CAG  CGG  GAG  CTG  GAT  GAG  GCC  ACG  GAG  AGC  AAC  GAG  GCC  ATG       2592
Lys  Leu  Gln  Arg  Glu  Leu  Asp  Glu  Ala  Thr  Glu  Ser  Asn  Glu  Ala  Met
     850                      855                      860

GGC  CGT  GAG  GTG  AAC  GCA  CTC  AAG  AGC  AAG  CTC  AGA  GGG  CCC  CCC  CCA       2640
Gly  Arg  Glu  Val  Asn  Ala  Leu  Lys  Ser  Lys  Leu  Arg  Gly  Pro  Pro  Pro
865                      870                      875                      880

CAG  GAA  ACT  TCG  CAG  TGATGCACCA  GGCGAGGAAA  CGAGACCTCT  TTCGTTCCTT            2695
Gln  Glu  Thr  Ser  Gln
               885

CTAGAAGGTC  TGGAGGACGT  AGAGTTATTG  AAAATGCAGA  TGGTTCTGAG  GAGGAACTGG             2755
```

```
ACACTCGAGA CGCAGACTTC AATGGAACCA AGGCCAGTGA ATAAGCAACT TTCTACAGTT    2815

TTGCACCACG GCAAGAAAAC CAAAAACCAA AACAAACAAA CAAAAAAAAC CCAACAACAA    2875

CCCGAACAAG AC                                                       2887
```

( 2 ) INFORMATION FOR SEQ ID NO:4:

( i ) SEQUENCE CHARACTERISTICS:
        ( A ) LENGTH: 885 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Pro  Arg  Val  Val  Pro  Asp  Gln  Arg  Ser  Lys  Phe  Glu  Asn  Glu  Glu  Phe
 1              5                        10                       15

Phe  Arg  Lys  Leu  Ser  Arg  Glu  Cys  Glu  Ile  Lys  Tyr  Thr  Gly  Phe  Arg
            20                       25                       30

Asp  Arg  Pro  His  Glu  Glu  Arg  Gln  Ala  Arg  Phe  Gln  Asn  Ala  Cys  Arg
            35                       40                       45

Asp  Gly  Arg  Ser  Glu  Ile  Ala  Phe  Val  Ala  Thr  Gly  Thr  Asn  Leu  Ser
       50                       55                       60

Leu  Gln  Phe  Phe  Pro  Ala  Ser  Trp  Gln  Gly  Glu  Gln  Arg  Gln  Thr  Pro
65                       70                       75                       80

Ser  Arg  Glu  Tyr  Val  Asp  Leu  Glu  Arg  Glu  Ala  Gly  Lys  Val  Tyr  Leu
                 85                       90                       95

Lys  Ala  Pro  Met  Ile  Leu  Asn  Gly  Val  Cys  Val  Ile  Trp  Lys  Gly  Trp
                100                      105                      110

Ile  Asp  Leu  Gln  Arg  Leu  Asp  Gly  Met  Gly  Cys  Leu  Glu  Phe  Asp  Glu
            115                      120                      125

Glu  Arg  Ala  Gln  Gln  Glu  Asp  Ala  Leu  Ala  Gln  Gln  Ala  Phe  Glu  Glu
       130                      135                      140

Ala  Arg  Arg  Arg  Thr  Arg  Glu  Phe  Glu  Asp  Arg  Asp  Arg  Ser  His  Arg
145                      150                      155                      160

Glu  Glu  Met  Glu  Ala  Lys  Ala  Asn  Leu  Asp  Lys  Asn  Lys  Gln  Thr  Leu
                165                      170                      175

Glu  Lys  Glu  Asn  Ala  Asp  Leu  Ala  Gly  Glu  Leu  Arg  Val  Leu  Gly  Gln
                180                      185                      190

Ala  Lys  Gln  Glu  Val  Glu  His  Lys  Lys  Lys  Leu  Glu  Ala  Gln  Val
            195                      200                      205

Gln  Glu  Leu  Gln  Ser  Lys  Cys  Ser  Asp  Gly  Glu  Arg  Ala  Arg  Ala  Glu
       210                      215                      220

Leu  Asn  Asp  Lys  Val  His  Lys  Leu  Gln  Asn  Glu  Val  Glu  Ser  Val  Thr
225                      230                      235                      240

Gly  Met  Leu  Asn  Glu  Ala  Glu  Gly  Lys  Ala  Ile  Lys  Leu  Ala  Lys  Asp
                245                      250                      255

Val  Ala  Ser  Leu  Ser  Ser  Gln  Leu  Gln  Asp  Thr  Gln  Glu  Leu  Leu  Gln
            260                      265                      270

Glu  Glu  Thr  Arg  Gln  Lys  Leu  Asn  Val  Ser  Thr  Lys  Leu  Arg  Gln  Leu
            275                      280                      285

Glu  Glu  Glu  Arg  Asn  Ser  Leu  Gln  Asp  Gln  Leu  Asp  Glu  Glu  Met  Glu
       290                      295                      300

Ala  Lys  Gln  Asn  Leu  Glu  Arg  His  Ile  Ser  Thr  Leu  Asn  Ile  Gln  Leu
305                      310                      315                      320

Ser  Asp  Ser  Lys  Lys  Lys  Leu  Gln  Asp  Phe  Ala  Ser  Thr  Val  Glu  Ala
                325                      330                      335
```

| | | | | | | | | | | | | | |
|---|---|---|---|---|---|---|---|---|---|---|---|---|---|
| Leu | Glu | Glu | Gly 340 | Lys | Lys | Arg | Phe | Gln 345 | Lys | Glu | Ile | Glu | Asn 350 | Leu | Thr |
| Gln | Gln | Tyr 355 | Glu | Glu | Lys | Ala | Ala 360 | Ala | Tyr | Asp | Lys 365 | Leu | Glu | Lys | Thr |
| Lys | Asn 370 | Arg | Leu | Gln | Gln 375 | Glu | Leu | Asp | Asp | Leu 380 | Val | Val | Asp | Leu | Asp |
| Asn 385 | Gln | Arg | Gln | Leu | Val 390 | Ser | Asn | Leu | Glu | Lys 395 | Gln | Arg | Lys | Phe 400 |
| Asp | Gln | Leu | Leu | Ala 405 | Glu | Glu | Lys | Asn | Ile 410 | Ser | Ser | Lys | Tyr | Ala 415 | Asp |
| Glu | Arg | Asp | Arg 420 | Ala | Glu | Ala | Glu | Ala 425 | Arg | Glu | Lys | Glu | Thr 430 | Lys | Ala |
| Leu | Ser | Leu | Ala 435 | Arg | Ala | Leu | Glu 440 | Glu | Ala | Leu | Glu | Ala 445 | Lys | Glu | Glu |
| Leu | Glu | Arg 450 | Thr | Asn | Lys | Met 455 | Leu | Lys | Ala | Glu | Met 460 | Glu | Asp | Leu | Val |
| Ser 465 | Ser | Lys | Asp | Asp | Val 470 | Gly | Lys | Asn | Val | His 475 | Glu | Leu | Glu | Lys | Ser 480 |
| Lys | Arg | Ala | Leu | Glu 485 | Thr | Gln | Met | Glu 490 | Glu | Met | Lys | Thr | Gln 495 | Leu | Glu |
| Glu | Leu | Glu | Asp 500 | Glu | Leu | Gln | Ala | Ser 505 | Glu | Asp | Ala | Lys | Leu 510 | Arg | Leu |
| Glu | Val | Asn | Met 515 | Gln | Ala | Leu | Lys | Gly 520 | Gln | Phe | Glu | Arg 525 | Asp | Leu | Gln |
| Ala | Arg | Asp 530 | Glu | Gln | Asn | Glu 535 | Glu | Lys | Arg | Arg | Gln 540 | Leu | Gln | Arg | Gln |
| Leu 545 | His | Glu | Tyr | Glu | Thr 550 | Glu | Leu | Glu | Asp | Glu 555 | Arg | Asn | Glu | Arg | Ala 560 |
| Leu | Ala | Ala | Ala | Ala 565 | Lys | Lys | Lys | Leu | Glu 570 | Gly | Asp | Leu | Lys | Asp 575 | Leu |
| Glu | Leu | Gln | Ala 580 | Asp | Ser | Ala | Ile | Lys 585 | Gly | Arg | Glu | Glu | Ala 590 | Ile | Lys |
| Gln | Leu | Arg 595 | Lys | Leu | Gln | Ala | Gln 600 | Met | Lys | Asp | Phe | Gln 605 | Arg | Glu | Leu |
| Glu | Asp | Ala 610 | Arg | Ala | Ser | Arg 615 | Asp | Glu | Ile | Phe | Ala 620 | Thr | Ala | Lys | Glu |
| Asn 625 | Glu | Lys | Lys | Ala | Lys 630 | Ser | Leu | Glu | Ala | Asp 635 | Leu | Met | Gln | Leu | Gln 640 |
| Glu | Asp | Leu | Ala | Ala 645 | Ala | Glu | Arg | Ala | Arg 650 | Lys | Gln | Ala | Asp | Leu 655 | Glu |
| Lys | Glu | Glu | Leu 660 | Ala | Glu | Glu | Leu | Ala 665 | Ser | Ser | Leu | Ser | Gly 670 | Arg | Asn |
| Ala | Leu | Gln | Asp 675 | Glu | Lys | Arg | Arg | Leu 680 | Glu | Ala | Arg | Ile | Ala 685 | Gln | Leu |
| Glu | Glu | Glu 690 | Leu | Glu | Glu | Glu | Gln 695 | Gly | Asn | Met | Glu | Ala 700 | Met | Ser | Asp |
| Arg 705 | Val | Arg | Lys | Ala | Thr 710 | Gln | Gln | Ala | Glu | Gln 715 | Leu | Ser | Asn | Glu | Leu 720 |
| Ala | Thr | Glu | Arg | Ser 725 | Thr | Ala | Gln | Lys | Asn 730 | Glu | Ser | Ala | Arg | Gln 735 |
| Leu | Glu | Arg | Gln 740 | Asn | Lys | Glu | Leu | Arg 745 | Ser | Lys | Leu | His 750 | Glu | Met | Glu |
| Gly | Ala | Val | Lys | Ser | Lys | Phe | Lys | Ser | Thr | Ile | Ala | Ala | Leu | Glu | Ala |

|   |   |   |   |   | 755 |   |   |   |   | 760 |   |   |   |   | 765 |   |   |
|---|---|---|---|---|---|---|---|---|---|---|---|---|---|---|---|---|---|
| Lys | Ile | Ala | Gln | Leu | Glu | Glu | Gln | Val | Glu | Gln | Glu | Ala | Arg | Glu | Lys |   |   |
|   | 770 |   |   |   |   | 775 |   |   |   | 780 |   |   |   |   |   |   |   |
| Gln | Ala | Ala | Thr | Lys | Ser | Leu | Lys | Gln | Lys | Asp | Lys | Lys | Leu | Lys | Glu |   |   |
| 785 |   |   |   |   | 790 |   |   |   | 795 |   |   |   |   |   | 800 |   |   |
| Ile | Leu | Leu | Gln | Val | Glu | Asp | Glu | Arg | Lys | Met | Ala | Glu | Gln | Tyr | Lys |   |   |
|   |   |   |   | 805 |   |   |   | 810 |   |   |   |   |   | 815 |   |   |   |
| Glu | Gln | Ala | Glu | Lys | Gly | Asn | Ala | Arg | Val | Lys | Gln | Leu | Lys | Arg | Gln |   |   |
|   |   |   | 820 |   |   |   |   | 825 |   |   |   |   | 830 |   |   |   |   |
| Leu | Glu | Glu | Ala | Glu | Glu | Glu | Ser | Gln | Arg | Ile | Asn | Ala | Asn | Arg | Arg |   |   |
|   |   | 835 |   |   |   |   | 840 |   |   |   |   | 845 |   |   |   |   |   |
| Lys | Leu | Gln | Arg | Glu | Leu | Asp | Glu | Ala | Thr | Glu | Ser | Asn | Glu | Ala | Met |   |   |
|   | 850 |   |   |   |   | 855 |   |   |   |   | 860 |   |   |   |   |   |   |
| Gly | Arg | Glu | Val | Asn | Ala | Leu | Lys | Ser | Lys | Leu | Arg | Gly | Pro | Pro | Pro |   |   |
| 865 |   |   |   |   | 870 |   |   |   |   | 875 |   |   |   |   | 880 |   |   |
| Gln | Glu | Thr | Ser | Gln |   |   |   |   |   |   |   |   |   |   |   |   |   |
|   |   |   |   | 885 |   |   |   |   |   |   |   |   |   |   |   |   |   |

( 2 ) INFORMATION FOR SEQ ID NO:5:

( i ) SEQUENCE CHARACTERISTICS:
        ( A ) LENGTH: 2680 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens
        ( C ) INDIVIDUAL ISOLATE: Sample 2
        ( F ) TISSUE TYPE: Acute myelomonocytic leukemia, M4Eo
            subtype (inv16)

( v i i i ) POSITION IN GENOME:
        ( A ) CHROMOSOME/SEGMENT: 16[inv(16)(p13q22)]

( i x ) FEATURE:
        ( A ) NAME/KEY: CDS
        ( B ) LOCATION: 1..2451

( x i ) SEQUENCE DESCRIPTION: SEQ ID NO:5:

| CCG | CGC | GTC | GTG | CCC | GAC | CAG | AGA | AGC | AAG | TTC | GAG | AAC | GAG | GAG | TTT | 48 |
|---|---|---|---|---|---|---|---|---|---|---|---|---|---|---|---|---|
| Pro | Arg | Val | Val | Pro | Asp | Gln | Arg | Ser | Lys | Phe | Glu | Asn | Glu | Glu | Phe |   |
| 1 |   |   |   | 5 |   |   |   |   | 10 |   |   |   |   | 15 |   |   |
| TTT | AGG | AAG | CTG | AGC | CGC | GAG | TGT | GAG | ATT | AAG | TAC | ACG | GGC | TTC | AGG | 96 |
| Phe | Arg | Lys | Leu | Ser | Arg | Glu | Cys | Glu | Ile | Lys | Tyr | Thr | Gly | Phe | Arg |   |
|   |   |   | 20 |   |   |   |   | 25 |   |   |   |   | 30 |   |   |   |
| GAC | CGG | CCC | CAC | GAG | GAA | CGC | CAG | GCA | CGC | TTC | CAG | AAC | GCC | TGC | CGC | 144 |
| Asp | Arg | Pro | His | Glu | Glu | Arg | Gln | Ala | Arg | Phe | Gln | Asn | Ala | Cys | Arg |   |
|   |   | 35 |   |   |   |   | 40 |   |   |   |   | 45 |   |   |   |   |
| GAC | GGC | CGC | TCG | GAA | ATC | GCT | TTT | GTG | GCC | ACA | GGA | ACC | AAT | CTG | TCT | 192 |
| Asp | Gly | Arg | Ser | Glu | Ile | Ala | Phe | Val | Ala | Thr | Gly | Thr | Asn | Leu | Ser |   |
|   | 50 |   |   |   |   | 55 |   |   |   |   | 60 |   |   |   |   |   |
| CTC | CAA | TTT | TTT | CCG | GCC | AGC | TGG | CAG | GGA | GAA | CAG | CGA | CAA | ACA | CCT | 240 |
| Leu | Gln | Phe | Phe | Pro | Ala | Ser | Trp | Gln | Gly | Glu | Gln | Arg | Gln | Thr | Pro |   |
| 65 |   |   |   |   | 70 |   |   |   |   | 75 |   |   |   |   | 80 |   |
| AGC | CGA | GAG | TAT | GTC | GAC | TTA | GAA | AGA | GAA | GCA | GGC | AAG | GTA | TAT | TTG | 288 |
| Ser | Arg | Glu | Tyr | Val | Asp | Leu | Glu | Arg | Glu | Ala | Gly | Lys | Val | Tyr | Leu |   |
|   |   |   |   | 85 |   |   |   | 90 |   |   |   |   | 95 |   |   |   |

| | | | | | | | | | | | | | | | | |
|---|---|---|---|---|---|---|---|---|---|---|---|---|---|---|---|---|
| AAG | GCT | CCC | ATG | ATT | CTG | AAT | GGA | GTC | TGT | GTT | ATC | TGG | AAA | GGC | TGG | 336 |
| Lys | Ala | Pro | Met | Ile | Leu | Asn | Gly | Val | Cys | Val | Ile | Trp | Lys | Gly | Trp | |
| | | | 100 | | | | 105 | | | | | 110 | | | | |
| ATT | GAT | CTC | CAA | AGA | CTG | GAT | GGT | ATG | GGC | TGT | CTG | GAG | TTT | GAT | GAG | 384 |
| Ile | Asp | Leu | Gln | Arg | Leu | Asp | Gly | Met | Gly | Cys | Leu | Glu | Phe | Asp | Glu | |
| | | | 115 | | | | 120 | | | | | 125 | | | | |
| GAG | CGA | GCC | CAG | CAG | GAG | GAT | GCA | TTA | GCA | CAA | CAG | GCC | TTT | GAA | GAG | 432 |
| Glu | Arg | Ala | Gln | Gln | Glu | Asp | Ala | Leu | Ala | Gln | Gln | Ala | Phe | Glu | Glu | |
| | 130 | | | | | 135 | | | | | 140 | | | | | |
| GCT | CGG | AGA | AGG | ACA | CGC | GAA | TTT | GAA | GAT | AGA | GAC | AGG | TCT | CAT | CGG | 480 |
| Ala | Arg | Arg | Arg | Thr | Arg | Glu | Phe | Glu | Asp | Arg | Asp | Arg | Ser | His | Arg | |
| 145 | | | | | 150 | | | | | 155 | | | | | 160 | |
| GAG | GAA | ATG | GAG | AAT | GAA | GTT | GAG | AGC | GTC | ACA | GGG | ATG | CTT | AAC | GAG | 528 |
| Glu | Glu | Met | Glu | Asn | Glu | Val | Glu | Ser | Val | Thr | Gly | Met | Leu | Asn | Glu | |
| | | | | 165 | | | | | 170 | | | | | 175 | | |
| GCC | GAG | GGG | AAG | GCC | ATT | AAG | CTG | GCC | AAG | GAC | GTG | GCG | TCC | CTC | AGT | 576 |
| Ala | Glu | Gly | Lys | Ala | Ile | Lys | Leu | Ala | Lys | Asp | Val | Ala | Ser | Leu | Ser | |
| | | | 180 | | | | 185 | | | | | 190 | | | | |
| TCC | CAG | CTC | CAG | GAC | ACC | CAG | GAG | TTG | CTT | CAA | GAA | GAA | ACC | CGG | CAG | 624 |
| Ser | Gln | Leu | Gln | Asp | Thr | Gln | Glu | Leu | Leu | Gln | Glu | Glu | Thr | Arg | Gln | |
| | | | 195 | | | | 200 | | | | | 205 | | | | |
| AAG | CTC | AAC | GTG | TCT | ACG | AAG | CTG | CGC | CAG | CTG | GAG | GAG | GAG | CGG | AAC | 672 |
| Lys | Leu | Asn | Val | Ser | Thr | Lys | Leu | Arg | Gln | Leu | Glu | Glu | Glu | Arg | Asn | |
| | | 210 | | | | | 215 | | | | | 220 | | | | |
| AGC | CTG | CAA | GAC | CAG | CTG | GAC | GAG | GAG | ATG | GAG | GCC | AAG | CAG | AAC | CTG | 720 |
| Ser | Leu | Gln | Asp | Gln | Leu | Asp | Glu | Glu | Met | Glu | Ala | Lys | Gln | Asn | Leu | |
| 225 | | | | | 230 | | | | | 235 | | | | | 240 | |
| GAG | CGC | CAC | ATC | TCC | ACT | CTC | AAC | ATC | CAG | CTC | TCC | GAC | TCG | AAG | AAG | 768 |
| Glu | Arg | His | Ile | Ser | Thr | Leu | Asn | Ile | Gln | Leu | Ser | Asp | Ser | Lys | Lys | |
| | | | | 245 | | | | | 250 | | | | | 255 | | |
| AAG | CTG | CAG | GAC | TTT | GCC | AGC | ACC | GTG | GAA | GCT | CTG | GAA | GAG | GGG | AAG | 816 |
| Lys | Leu | Gln | Asp | Phe | Ala | Ser | Thr | Val | Glu | Ala | Leu | Glu | Glu | Gly | Lys | |
| | | | 260 | | | | 265 | | | | | 270 | | | | |
| AAG | AGG | TTC | CAG | AAG | GAG | ATC | GAG | AAC | CTC | ACC | CAG | CAG | TAC | GAG | GAG | 864 |
| Lys | Arg | Phe | Gln | Lys | Glu | Ile | Glu | Asn | Leu | Thr | Gln | Gln | Tyr | Glu | Glu | |
| | | 275 | | | | | 280 | | | | | 285 | | | | |
| AAG | GCG | GCC | GCT | TAT | GAT | AAA | CTG | GAA | AAG | ACC | AAG | AAC | AGG | CTT | CAG | 912 |
| Lys | Ala | Ala | Ala | Tyr | Asp | Lys | Leu | Glu | Lys | Thr | Lys | Asn | Arg | Leu | Gln | |
| | 290 | | | | | 295 | | | | | 300 | | | | | |
| CAG | GAG | CTG | GAC | GAC | CTG | GTT | GTT | GAT | TTG | GAC | AAC | CAG | CGG | CAA | CTC | 960 |
| Gln | Glu | Leu | Asp | Asp | Leu | Val | Val | Asp | Leu | Asp | Asn | Gln | Arg | Gln | Leu | |
| 305 | | | | | 310 | | | | | 315 | | | | | 320 | |
| GTG | TCC | AAC | CTG | GAA | AAG | AAG | CAG | AGG | AAA | TTT | GAT | CAG | TTG | TTA | GCC | 1008 |
| Val | Ser | Asn | Leu | Glu | Lys | Lys | Gln | Arg | Lys | Phe | Asp | Gln | Leu | Leu | Ala | |
| | | | | 325 | | | | | 330 | | | | | 335 | | |
| GAG | GAG | AAA | AAC | ATC | TCT | TCC | AAA | TAC | GCG | GAT | GAG | AGG | GAC | AGA | GCT | 1056 |
| Glu | Glu | Lys | Asn | Ile | Ser | Ser | Lys | Tyr | Ala | Asp | Glu | Arg | Asp | Arg | Ala | |
| | | | 340 | | | | | 345 | | | | | 350 | | | |
| GAG | GCA | GAA | GCC | AGG | GAG | AAG | GAA | ACC | AAG | GCC | CTG | TCC | CTG | GCT | CGG | 1104 |
| Glu | Ala | Glu | Ala | Arg | Glu | Lys | Glu | Thr | Lys | Ala | Leu | Ser | Leu | Ala | Arg | |
| | | 355 | | | | | 360 | | | | | 365 | | | | |
| GCC | CTT | GAA | GAG | GCC | TTG | GAA | GCC | AAA | GAG | GAA | CTC | GAG | CGG | ACC | AAC | 1152 |
| Ala | Leu | Glu | Glu | Ala | Leu | Glu | Ala | Lys | Glu | Glu | Leu | Glu | Arg | Thr | Asn | |
| | 370 | | | | | 375 | | | | | 380 | | | | | |
| AAA | ATG | CTC | AAA | GCC | GAA | ATG | GAA | GAC | CTG | GTC | AGC | TCC | AAG | GAT | GAC | 1200 |
| Lys | Met | Leu | Lys | Ala | Glu | Met | Glu | Asp | Leu | Val | Ser | Ser | Lys | Asp | Asp | |
| 385 | | | | | 390 | | | | | 395 | | | | | 400 | |
| GTG | GGC | AAG | AAC | GTC | CAT | GAG | CTG | GAG | AAG | TCC | AAG | CGG | GCC | CTG | GAG | 1248 |
| Val | Gly | Lys | Asn | Val | His | Glu | Leu | Glu | Lys | Ser | Lys | Arg | Ala | Leu | Glu | |
| | | | | 405 | | | | | 410 | | | | | 415 | | |

| | | | | | | | | | | | | | | | | |
|---|---|---|---|---|---|---|---|---|---|---|---|---|---|---|---|---|
| ACC | CAG | ATG | GAG | GAG | ATG | AAG | ACG | CAG | CTG | GAA | GAG | CTG | GAG | GAC | GAG | 1296 |
| Thr | Gln | Met | Glu 420 | Glu | Met | Lys | Thr 425 | Gln | Leu | Glu | Glu | Leu 430 | Glu | Asp | Glu | |
| CTG | CAA | GCC | TCG | GAG | GAC | GCC | AAA | CTG | CGG | CTG | GAA | GTC | AAC | ATG | CAG | 1344 |
| Leu | Gln | Ala | Ser 435 | Glu | Asp | Ala | Lys 440 | Leu | Arg | Leu | Glu | Val 445 | Asn | Met | Gln | |
| GCG | CTC | AAG | GGC | CAG | TTC | GAA | AGG | GAT | CTC | CAA | GCC | CGG | GAC | GAG | CAG | 1392 |
| Ala | Leu | Lys 450 | Gly | Gln | Phe | Glu | Arg 455 | Asp | Leu | Gln | Ala | Arg 460 | Asp | Glu | Gln | |
| AAT | GAG | GAG | AAG | AGG | AGG | CAA | CTG | CAG | AGA | CAG | CTT | CAC | GAG | TAT | GAG | 1440 |
| Asn 465 | Glu | Glu | Lys | Arg 470 | Arg | Gln | Leu | Gln | Arg 475 | Gln | Leu | His | Glu | Tyr 480 | Glu | |
| ACG | GAA | CTG | GAA | GAC | GAG | CGA | AAC | GAA | CGT | GCC | CTG | GCA | GCT | GCA | GCA | 1488 |
| Thr | Glu | Leu | Glu | Asp 485 | Glu | Arg | Asn | Glu | Arg 490 | Ala | Leu | Ala | Ala | Ala 495 | Ala | |
| AAG | AAG | AAG | CTG | GAA | GGG | GAC | CTG | AAA | GAC | CTG | GAG | CTT | CAG | GCC | GAC | 1536 |
| Lys | Lys | Lys | Leu 500 | Glu | Gly | Asp | Leu | Lys 505 | Asp | Leu | Glu | Leu | Gln 510 | Ala | Asp | |
| TCT | GCC | ATC | AAG | GGG | AGG | GAG | GAA | GCC | ATC | AAG | CAG | CTA | CGC | AAA | CTG | 1584 |
| Ser | Ala | Ile 515 | Lys | Gly | Arg | Glu | Glu 520 | Ala | Ile | Lys | Gln | Leu 525 | Arg | Lys | Leu | |
| CAG | GCT | CAG | ATG | AAG | GAC | TTT | CAA | AGA | GAG | CTG | GAA | GAT | GCC | CGT | GCC | 1632 |
| Gln | Ala | Gln | Met 530 | Lys | Asp | Phe | Gln 535 | Arg | Glu | Leu | Glu | Asp 540 | Ala | Arg | Ala | |
| TCC | AGA | GAT | GAG | ATC | TTT | GCC | ACA | GCC | AAA | GAG | AAT | GAG | AAG | AAA | GCC | 1680 |
| Ser | Arg | Asp 545 | Glu | Ile | Phe | Ala | Thr 550 | Ala | Lys | Glu | Asn | Glu 555 | Lys | Lys | Ala 560 | |
| AAG | AGC | TTG | GAA | GCA | GAC | CTC | ATG | CAG | CTA | CAA | GAG | GAC | CTC | GCC | GCC | 1728 |
| Lys | Ser | Leu | Glu | Ala 565 | Asp | Leu | Met | Gln | Leu 570 | Gln | Glu | Asp | Leu | Ala 575 | Ala | |
| GCT | GAG | AGG | GCT | CGC | AAA | CAA | GCG | GAC | CTC | GAG | AAG | GAG | GAA | CTG | GCA | 1776 |
| Ala | Glu | Arg | Ala 580 | Arg | Lys | Gln | Ala | Asp 585 | Leu | Glu | Lys | Glu | Glu 590 | Leu | Ala | |
| GAG | GAG | CTG | GCC | AGT | AGC | CTG | TCG | GGA | AGG | AAC | GCA | CTC | CAG | GAC | GAG | 1824 |
| Glu | Glu | Leu 595 | Ala | Ser | Ser | Leu | Ser 600 | Gly | Arg | Asn | Ala | Leu 605 | Gln | Asp | Glu | |
| AAG | CGC | CGC | CTG | GAG | GCC | CGG | ATC | GCC | CAG | CTG | GAG | GAG | GAG | CTG | GAG | 1872 |
| Lys | Arg 610 | Arg | Leu | Glu | Ala | Arg 615 | Ile | Ala | Gln | Leu | Glu 620 | Glu | Glu | Leu | Glu | |
| GAG | GAG | CAG | GGC | AAC | ATG | GAG | GCC | ATG | AGC | GAC | CGG | GTC | CGC | AAA | GCC | 1920 |
| Glu 625 | Glu | Gln | Gly | Asn | Met 630 | Glu | Ala | Met | Ser | Asp 635 | Arg | Val | Arg | Lys | Ala 640 | |
| ACA | CAG | CAG | GCC | GAG | CAG | CTC | AGC | AAC | GAG | CTG | GCC | ACA | GAG | CGC | AGC | 1968 |
| Thr | Gln | Gln | Ala | Glu 645 | Gln | Leu | Ser | Asn | Glu 650 | Leu | Ala | Thr | Glu | Arg 655 | Ser | |
| ACG | GCC | CAG | AAG | AAT | GAG | AGT | GCC | CGG | CAG | CAG | CTC | GAG | CGG | CAG | AAC | 2016 |
| Thr | Ala | Gln | Lys 660 | Asn | Glu | Ser | Ala | Arg 665 | Gln | Gln | Leu | Glu | Arg 670 | Gln | Asn | |
| AAG | GAG | CTC | CGG | AGC | AAG | CTC | CAC | GAG | ATG | GAG | GGG | GCC | GTC | AAG | TCC | 2064 |
| Lys | Glu | Leu | Arg 675 | Ser | Lys | Leu | His | Glu 680 | Met | Glu | Gly | Ala | Val 685 | Lys | Ser | |
| AAG | TTC | AAG | TCC | ACC | ATC | GCG | GCG | CTG | GAG | GCC | AAG | ATT | GCA | CAG | CTG | 2112 |
| Lys | Phe | Lys 690 | Ser | Thr | Ile | Ala | Ala 695 | Leu | Glu | Ala | Lys | Ile 700 | Ala | Gln | Leu | |
| GAG | GAG | CAG | GTC | GAG | CAG | GAG | GCC | AGA | GAG | AAA | CAG | GCA | GCC | ACC | AAG | 2160 |
| Glu 705 | Glu | Gln | Val | Glu | Gln 710 | Glu | Ala | Arg | Glu | Lys 715 | Gln | Ala | Ala | Thr | Lys 720 | |
| TCG | CTG | AAG | CAG | AAA | GAC | AAG | AAG | CTG | AAG | GAA | ATC | TTG | CTG | CAG | GTG | 2208 |
| Ser | Leu | Lys | Gln | Lys 725 | Asp | Lys | Lys | Leu | Lys 730 | Glu | Ile | Leu | Leu | Gln 735 | Val | |

| | | | | | | | | | | | | | | | | |
|---|---|---|---|---|---|---|---|---|---|---|---|---|---|---|---|---|
| GAG | GAC | GAG | CGC | AAG | ATG | GCC | GAG | CAG | TAC | AAG | GAG | CAG | GCA | GAG | AAA | 2256 |
| Glu | Asp | Glu | Arg | Lys | Met | Ala | Glu | Gln | Tyr | Lys | Glu | Gln | Ala | Glu | Lys | |
| | | | 740 | | | | | 745 | | | | | 750 | | | |
| GGC | AAT | GCC | AGG | GTC | AAG | CAG | CTC | AAG | AGG | CAG | CTG | GAG | GAG | GCA | GAG | 2304 |
| Gly | Asn | Ala | Arg | Val | Lys | Gln | Leu | Lys | Arg | Gln | Leu | Glu | Glu | Ala | Glu | |
| | | 755 | | | | | 760 | | | | | 765 | | | | |
| GAG | GAG | TCC | CAG | CGC | ATC | AAC | GCC | AAC | CGC | AGG | AAG | CTG | CAG | CGG | GAG | 2352 |
| Glu | Glu | Ser | Gln | Arg | Ile | Asn | Ala | Asn | Arg | Arg | Lys | Leu | Gln | Arg | Glu | |
| 770 | | | | | 775 | | | | | 780 | | | | | | |
| CTG | GAT | GAG | GCC | ACG | GAG | AGC | AAC | GAG | GCC | ATG | GGC | CGT | GAG | GTG | AAC | 2400 |
| Leu | Asp | Glu | Ala | Thr | Glu | Ser | Asn | Glu | Ala | Met | Gly | Arg | Glu | Val | Asn | |
| 785 | | | | | 790 | | | | | 795 | | | | | 800 | |
| GCA | CTC | AAG | AGC | AAG | CTC | AGA | GGG | CCC | CCC | CAG | GAA | ACT | TCG | CAG | | 2448 |
| Ala | Leu | Lys | Ser | Lys | Leu | Arg | Gly | Pro | Pro | Gln | Glu | Thr | Ser | Gln | | |
| | | | | 805 | | | | | 810 | | | | | 815 | | |

```
TGATGCACCA GGCGAGGAAA CGAGACCTCT TCGTTCCTT CTAGAAGGTC TGGAGGACGT    2508
AGAGTTATTG AAAATGCAGA TGGTTCTGAG GAGGAACTGG ACACTCGAGA CGCAGACTTC    2568
AATGGAACCA AGGCCAGTGA ATAAGCAACT TTCTACAGTT TTGCACCACG GCAAGAAAAC    2628
CAAAAACCAA AACAAACAAA CAAAAAAAAC CCAACAACAA CCCGAACAAG AC            2680
```

( 2 ) INFORMATION FOR SEQ ID NO:6:

( i ) SEQUENCE CHARACTERISTICS:
        ( A ) LENGTH: 816 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Pro | Arg | Val | Val | Pro | Asp | Gln | Arg | Ser | Lys | Phe | Glu | Asn | Glu | Phe |
| 1 | | | | 5 | | | | | 10 | | | | | 15 |
| Phe | Arg | Lys | Leu | Ser | Arg | Glu | Cys | Glu | Ile | Lys | Tyr | Thr | Gly | Phe | Arg |
| | | | 20 | | | | | 25 | | | | | 30 | | |
| Asp | Arg | Pro | His | Glu | Glu | Arg | Gln | Ala | Arg | Phe | Gln | Asn | Ala | Cys | Arg |
| | | 35 | | | | | 40 | | | | | 45 | | | |
| Asp | Gly | Arg | Ser | Glu | Ile | Ala | Phe | Val | Ala | Thr | Gly | Thr | Asn | Leu | Ser |
| | 50 | | | | | 55 | | | | | 60 | | | | |
| Leu | Gln | Phe | Phe | Pro | Ala | Ser | Trp | Gln | Gly | Glu | Gln | Arg | Gln | Thr | Pro |
| 65 | | | | | 70 | | | | | 75 | | | | | 80 |
| Ser | Arg | Glu | Tyr | Val | Asp | Leu | Glu | Arg | Glu | Ala | Gly | Lys | Val | Tyr | Leu |
| | | | | 85 | | | | | 90 | | | | | 95 | |
| Lys | Ala | Pro | Met | Ile | Leu | Asn | Gly | Val | Cys | Val | Ile | Trp | Lys | Gly | Trp |
| | | | 100 | | | | | 105 | | | | | 110 | | |
| Ile | Asp | Leu | Gln | Arg | Leu | Asp | Gly | Met | Gly | Cys | Leu | Glu | Phe | Asp | Glu |
| | | | 115 | | | | | 120 | | | | | 125 | | |
| Glu | Arg | Ala | Gln | Gln | Glu | Asp | Ala | Leu | Ala | Gln | Gln | Ala | Phe | Glu | Glu |
| | | 130 | | | | | 135 | | | | | 140 | | | |
| Ala | Arg | Arg | Arg | Thr | Arg | Glu | Phe | Glu | Asp | Arg | Asp | Arg | Ser | His | Arg |
| 145 | | | | | 150 | | | | | 155 | | | | | 160 |
| Glu | Glu | Met | Glu | Asn | Glu | Val | Glu | Ser | Val | Thr | Gly | Met | Leu | Asn | Glu |
| | | | | 165 | | | | | 170 | | | | | 175 | |
| Ala | Glu | Gly | Lys | Ala | Ile | Lys | Leu | Ala | Lys | Asp | Val | Ala | Ser | Leu | Ser |
| | | | 180 | | | | | 185 | | | | | 190 | | |
| Ser | Gln | Leu | Gln | Asp | Thr | Gln | Glu | Leu | Leu | Gln | Glu | Glu | Thr | Arg | Gln |
| | | | 195 | | | | | 200 | | | | | 205 | | |
| Lys | Leu | Asn | Val | Ser | Thr | Lys | Leu | Arg | Gln | Leu | Glu | Glu | Glu | Arg | Asn |

|     |     |     |     |     |     |     |     |     |     |     |     |     |     |     |
| --- | --- | --- | --- | --- | --- | --- | --- | --- | --- | --- | --- | --- | --- | --- |
|     |     |     | 210 |     |     |     |     | 215 |     |     |     |     | 220 |     |
| Ser 225 | Leu | Gln | Asp | Gln | Leu 230 | Asp | Glu | Glu | Met | Glu 235 | Ala | Lys | Gln | Asn 240 |
| Glu | Arg | His | Ile | Ser 245 | Thr | Leu | Asn | Ile | Gln 250 | Leu | Ser | Asp | Ser | Lys 255 |
| Lys | Leu | Gln | Asp | Phe 260 | Ala | Ser | Thr | Val | Glu 265 | Ala | Leu | Glu | Glu | Gly 270 | Lys |
| Lys | Arg | Phe 275 | Gln | Lys | Glu | Ile | Glu 280 | Asn | Leu | Thr | Gln | Gln 285 | Tyr | Glu | Glu |
| Lys | Ala 290 | Ala | Ala | Tyr | Asp | Lys 295 | Leu | Glu | Lys | Thr | Lys 300 | Asn | Arg | Leu | Gln |
| Gln 305 | Glu | Leu | Asp | Asp | Leu 310 | Val | Val | Asp | Leu | Asp 315 | Asn | Gln | Arg | Gln | Leu 320 |
| Val | Ser | Asn | Leu | Glu 325 | Lys | Lys | Gln | Arg | Lys 330 | Phe | Asp | Gln | Leu | Leu 335 | Ala |
| Glu | Glu | Lys | Asn 340 | Ile | Ser | Ser | Lys | Tyr 345 | Ala | Asp | Glu | Arg | Asp 350 | Arg | Ala |
| Glu | Ala | Glu 355 | Ala | Arg | Glu | Lys | Glu 360 | Thr | Lys | Ala | Leu | Ser 365 | Leu | Ala | Arg |
| Ala | Leu 370 | Glu | Glu | Ala | Leu | Glu 375 | Ala | Lys | Glu | Glu | Leu 380 | Glu | Arg | Thr | Asn |
| Lys 385 | Met | Leu | Lys | Ala | Glu 390 | Met | Glu | Asp | Leu | Val 395 | Ser | Ser | Lys | Asp | Asp 400 |
| Val | Gly | Lys | Asn | Val 405 | His | Glu | Leu | Glu | Lys 410 | Ser | Lys | Arg | Ala | Leu 415 | Glu |
| Thr | Gln | Met | Glu 420 | Glu | Met | Lys | Thr | Gln 425 | Leu | Glu | Glu | Leu | Glu 430 | Asp | Glu |
| Leu | Gln | Ala | Ser 435 | Glu | Asp | Ala | Lys | Leu 440 | Arg | Leu | Glu | Val | Asn 445 | Met | Gln |
| Ala | Leu | Lys 450 | Gly | Gln | Phe | Glu | Arg 455 | Asp | Leu | Gln | Ala | Arg 460 | Asp | Glu | Gln |
| Asn 465 | Glu | Glu | Lys | Arg | Arg 470 | Gln | Leu | Gln | Arg | Gln 475 | Leu | His | Glu | Tyr | Glu 480 |
| Thr | Glu | Leu | Glu | Asp 485 | Glu | Arg | Asn | Glu | Arg 490 | Ala | Leu | Ala | Ala | Ala 495 | Ala |
| Lys | Lys | Lys | Leu 500 | Glu | Gly | Asp | Leu | Lys 505 | Asp | Leu | Glu | Leu | Gln 510 | Ala | Asp |
| Ser | Ala | Ile | Lys 515 | Gly | Arg | Glu | Glu | Ala 520 | Ile | Lys | Gln | Leu | Arg 525 | Lys | Leu |
| Gln | Ala | Gln | Met 530 | Lys | Asp | Phe | Gln | Arg 535 | Glu | Leu | Glu | Asp | Ala 540 | Arg | Ala |
| Ser | Arg | Asp | Glu | Ile 545 | Phe | Ala | Thr | Ala | Lys 550 | Glu | Asn | Glu | Lys | Lys 555 | Ala 560 |
| Lys | Ser | Leu | Glu | Ala 565 | Asp | Leu | Met | Gln | Leu 570 | Gln | Glu | Asp | Leu | Ala 575 | Ala |
| Ala | Glu | Arg | Ala 580 | Arg | Lys | Gln | Ala | Asp 585 | Leu | Glu | Lys | Glu | Glu 590 | Leu | Ala |
| Glu | Glu | Leu | Ala 595 | Ser | Ser | Leu | Ser | Gly 600 | Arg | Asn | Ala | Leu | Gln 605 | Asp | Glu |
| Lys | Arg | Arg 610 | Leu | Glu | Ala | Arg | Ile 615 | Ala | Gln | Leu | Glu | Glu 620 | Glu | Leu | Glu |
| Glu 625 | Glu | Gln | Gly | Asn | Met 630 | Glu | Ala | Met | Ser | Asp 635 | Arg | Val | Arg | Lys | Ala 640 |

```
Thr  Gln  Gln  Ala  Glu  Gln  Leu  Ser  Asn  Glu  Leu  Ala  Thr  Glu  Arg  Ser
              645                     650                     655

Thr  Ala  Gln  Lys  Asn  Glu  Ser  Ala  Arg  Gln  Gln  Leu  Glu  Arg  Gln  Asn
              660                     665                     670

Lys  Glu  Leu  Arg  Ser  Lys  Leu  His  Glu  Met  Glu  Gly  Ala  Val  Lys  Ser
         675                     680                     685

Lys  Phe  Lys  Ser  Thr  Ile  Ala  Ala  Leu  Glu  Ala  Lys  Ile  Ala  Gln  Leu
         690                     695                     700

Glu  Glu  Gln  Val  Glu  Gln  Glu  Ala  Arg  Glu  Lys  Gln  Ala  Ala  Thr  Lys
705                     710                     715                     720

Ser  Leu  Lys  Gln  Lys  Asp  Lys  Lys  Leu  Lys  Glu  Ile  Leu  Leu  Gln  Val
                   725                     730                     735

Glu  Asp  Glu  Arg  Lys  Met  Ala  Glu  Gln  Tyr  Lys  Glu  Gln  Ala  Glu  Lys
              740                     745                     750

Gly  Asn  Ala  Arg  Val  Lys  Gln  Leu  Lys  Arg  Gln  Leu  Glu  Glu  Ala  Glu
         755                     760                     765

Glu  Glu  Ser  Gln  Arg  Ile  Asn  Ala  Asn  Arg  Arg  Lys  Leu  Gln  Arg  Glu
         770                     775                     780

Leu  Asp  Glu  Ala  Thr  Glu  Ser  Asn  Glu  Ala  Met  Gly  Arg  Glu  Val  Asn
785                     790                     795                     800

Ala  Leu  Lys  Ser  Lys  Leu  Arg  Gly  Pro  Pro  Pro  Gln  Glu  Thr  Ser  Gln
                   805                     810                     815
```

(2) INFORMATION FOR SEQ ID NO:7:

(i) SEQUENCE CHARACTERISTICS:
        (A) LENGTH: 2883 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens
        (C) INDIVIDUAL ISOLATE: Composite RL9a clone and PCR product (vii) IMMEDIATE SOURCE:
        (A) LIBRARY: HeLa
        (B) CLONE: RL9a (viii) POSITION IN GENOME:
        (A) CHROMOSOME/SEGMENT: 16

(ix) FEATURE:
        (A) NAME/KEY: CDS
        (B) LOCATION: 1..543

(xi) SEQUENCE DESCRIPTION: SEQ ID NO:7:

```
CCG  CGC  GTC  GTG  CCC  GAC  CAG  AGA  AGC  AAG  TTC  GAG  AAC  GAG  GAG  TTT      48
Pro  Arg  Val  Val  Pro  Asp  Gln  Arg  Ser  Lys  Phe  Glu  Asn  Glu  Glu  Phe
  1                     5                      10                      15

TTT  AGG  AAG  CTG  AGC  CGC  GAG  TGT  GAG  ATT  AAG  TAC  ACG  GGC  TTC  AGG      96
Phe  Arg  Lys  Leu  Ser  Arg  Glu  Cys  Glu  Ile  Lys  Tyr  Thr  Gly  Phe  Arg
              20                      25                      30

GAC  CGG  CCC  CAC  GAG  GAA  CGC  CAG  GCA  CGC  TTC  CAG  AAC  GCC  TGC  CGC     144
Asp  Arg  Pro  His  Glu  Glu  Arg  Gln  Ala  Arg  Phe  Gln  Asn  Ala  Cys  Arg
         35                      40                      45

GAC  GGC  CGC  TCG  GAA  ATC  GCT  TTT  GTG  GCC  ACA  GGA  ACC  AAT  CTG  TCT     192
Asp  Gly  Arg  Ser  Glu  Ile  Ala  Phe  Val  Ala  Thr  Gly  Thr  Asn  Leu  Ser
    50                      55                      60
```

```
CTC  CAA  TTT  TTT  CCG  GCC  AGC  TGG  CAG  GGA  GAA  CAG  CGA  CAA  ACA  CCT       240
Leu  Gln  Phe  Phe  Pro  Ala  Ser  Trp  Gln  Gly  Glu  Gln  Arg  Gln  Thr  Pro
 65                 70                      75                      80

AGC  CGA  GAG  TAT  GTC  GAC  TTA  GAA  AGA  GAA  GCA  GGC  AAG  GTA  TAT  TTG       288
Ser  Arg  Glu  Tyr  Val  Asp  Leu  Glu  Arg  Glu  Ala  Gly  Lys  Val  Tyr  Leu
                         85                      90                      95

AAG  GCT  CCC  ATG  ATT  CTG  AAT  GGA  GTC  TGT  GTT  ATC  TGG  AAA  GGC  TGG       336
Lys  Ala  Pro  Met  Ile  Leu  Asn  Gly  Val  Cys  Val  Ile  Trp  Lys  Gly  Trp
               100                     105                     110

ATT  GAT  CTC  CAA  AGA  CTG  GAT  GGT  ATG  GGC  TGT  CTG  GAG  TTT  GAT  GAG       384
Ile  Asp  Leu  Gln  Arg  Leu  Asp  Gly  Met  Gly  Cys  Leu  Glu  Phe  Asp  Glu
                    115                     120                     125

GAG  CGA  GCC  CAG  CAG  GAG  GAT  GCA  TTA  GCA  CAA  CAG  GCC  TTT  GAA  GAG       432
Glu  Arg  Ala  Gln  Gln  Glu  Asp  Ala  Leu  Ala  Gln  Gln  Ala  Phe  Glu  Glu
      130                     135                     140

GCT  CGG  AGA  AGG  ACA  CGC  GAA  TTT  GAA  GAT  AGA  GAC  AGG  TCT  CAT  CGG       480
Ala  Arg  Arg  Arg  Thr  Arg  Glu  Phe  Glu  Asp  Arg  Asp  Arg  Ser  His  Arg
145                      150                     155                     160

GAG  GAA  ATG  GAG  GTG  AGA  GTT  TCA  CAG  CTG  CTG  GCA  GTA  ACT  GGC  AAG       528
Glu  Glu  Met  Glu  Val  Arg  Val  Ser  Gln  Leu  Leu  Ala  Val  Thr  Gly  Lys
                         165                     170                     175

AAG  ACA  ACA  AGA  CCC  TAGTCCTGGT  TCCAATTTAG  GTGGTGGTGA  TGACCTCAAA              583
Lys  Thr  Thr  Arg  Pro
                    180

CTTCGTTAAT  TAATAGCACA  GCAGATGTGT  GCTGCCCATC  TTTACATACA  CATTGCTTCT              643

AGTTGGCAGA  AATAATTGAT  TAAAAGACCA  GAAACTGTGA  TAACTGGAGG  TACTACGGTC              703

TATTTCTCAA  CCTTAGGCAG  TAATAGACAT  CACAAACTGC  CATGGTTTTG  CACTATGATT              763

ATAATACCTG  CATTTCTAAT  TTTTTAAGCA  TGTAGCCAGT  AATAATTTGA  AGTTTTTTTT              823

CTATGCAAGC  TTACCTTGTT  GGCATTATTT  TAGGGAGTTG  AAACTATCAA  CTGTAAAGCT              883

CCTTTTCTTC  CACTTTAATT  TAAAAGTTCA  TGTCATTTAA  AAACAAGTCA  AGAAATTAAA              943

ATTGTATCAG  AGGGTTTTCT  CTAATCATTT  TTTCTATTTT  TTTTTTGTA   CTTCTAGATG             1003

TTTTGGTTAT  ACAGCTTCAT  TTAGATGAG   CATTCTTATT  TTTTGTTTTG  TTTGCCCCAT             1063

TTCCTTTTGT  GTTTTTATAG  TCTATAGCAT  TTTAAAACTG  CTGATGTTGT  TTGCATTATT             1123

TACAGGCTAA  AAACTTAGTA  GCATAGAGCT  GTCTGCCACA  GCCTTCTGAC  AAAGTTTACA             1183

GTTATTAAAG  TTGCAGTATC  CTTTTAAATG  CTAGTAATCA  GCACTCTTTC  TTTTTTTTTT             1243

TTTTAATGAGA  GACAGGGTCT  CGCAGTGTTG  CCCAGGCTGG  TCTCGAACTC  CTGGCATCAA            1303

GCGATCCTCC  TGCCTTAGCC  TCCCAGAGTA  CTGGGATTAC  AGGCTCTTTC  TTTTTAAACA             1363

TAAAAGTTTT  AAATTGGTAT  TAACTCTGTA  CTCTGCCCTA  GATTGTTTTA  GCTTCTGTTC             1423

TGTAATCATG  AGTTTGGTTG  GAGATATTCT  CCATAGATGA  TCTTCTACTG  AAATGCCTAA             1483

AGAAGTCACA  GGCTGGCTTC  TGTTTTATTC  AGGGATTTTT  TTAAAAAGTC  AATCAGAAAA             1543

GGGATACTGG  AGCTTCTTCA  TGTATGTAAC  AGCATATTAA  ACTGGAGACA  GTGATGAATC             1603

AGCTACAAAG  GTAATATTGT  ATTAAAATCA  TGTTTAAGAT  AGCTGCTTTT  ATGTGTATTT             1663

TATATTGCAT  GCTTTTGTAA  AAACATGCTG  GGTGATGAAA  GATTAGTTTT  AGAGAGAAAA             1723

TGTTCATCTG  TGCAGAGGAT  GCATTTTCTT  CCATTAATTC  TGGAAAAAAC  GTTCACAGTT             1783

ATATATATGG  TATTTTGCAA  AAGGACTATT  AATAGAACCT  TTTGAGATGA  ATTAATGTAA             1843

GAATATTTTT  TAAATAGGCT  TACTGTCAAA  TTGCAACTTT  TTTTTAGAT   ACAGAGTGGA             1903

AAACAGTGCT  AAGTCATTTG  GCACCTCCTT  ACAAATATTT  TTTCATGGTC  ACATTTATTA             1963

AATGTTACTA  CATTTCTGAA  TTTTTGAAAA  ATGTATTTTA  TCATTAAATG  GCATTATTTT             2023
```

```
CAAAGGGTGA  AAAACTGACA  CAGTCAATTC  AGAAAATGGA  CTGAAGTCTG  AATAAGGTCA   2083

TTGCATTTAA  AAAGCATATA  ACTGTACTTG  ACTGATGAGG  GAGGTGTTAC  TTTCATTGTA   2143

TATAGGTCTT  ATTTCATAAA  CAGATATCCT  GTATCAAATA  AAAGTATTTG  TTATATATTT   2203

GAAGTTATGC  ATGGAAGGA   GTGTGTTTAA  ATTGTTACAA  ACAATAATGC  GTCATTAAAG   2263

GCCATGCTGA  TCTTGCATAA  CTATAAGTAC  TATGAATGAA  TTTGGTTGGT  TTTGGTGTTG   2323

TACAGCTCAC  ATGTTTACAC  ACTCAGTGCC  CTAATTTCCC  CTGAGGGAAT  CGCTTTTTAA   2383

GTGATCCTTA  CAGTGGTGTT  TTATGTTACT  TTATTACAGA  GCTCCTTGGT  TTTTTACTTC   2443

TGCACTTAAA  TTTTTTTAAA  TAACATGATG  ATGGTACATT  TTCCTCTATT  GTCTAGCTAA   2503

GGGCTTTCGG  TCCACCAGTA  AATAAGATCA  AATGCTCTTA  AATGTTCCTG  TTACCATCCT   2563

AATGTAAATA  CTGGATTTTT  CTGTCATTTA  GCACCATGCT  GCTTCTGTCT  GTCTTAATGC   2623

TGGCATTAAG  ATCATGAGCC  CTTTTCTCC   AGTAGTACAG  GCTTTGAAAA  CTACTTCTAT   2683

TAAGTTATTG  ATGCAATTTG  ATATTTTTC   ATAATCTATA  TTTAAACAAA  ATTACATCAT   2743

TGCATCATCT  TTTCTAAATT  CATCTCCATT  AAAACTTGCC  TTAAGCTACC  AGATTGCTTT   2803

TGCCACCATT  GGCCATACTG  TGTGTTTGTT  TGTTTAATTT  ACTTTCACAA  TAAACTTCTG   2863

TGTAGTAAAA  AAAAAAAAA                                                   2883
```

( 2 ) INFORMATION FOR SEQ ID NO:8:

( i ) SEQUENCE CHARACTERISTICS:
 ( A ) LENGTH: 181 amino acids
 ( B ) TYPE: amino acid
 ( D ) TOPOLOGY: linear ( i i ) MOLECULE TYPE: protein ( x i ) SEQUENCE DESCRIPTION: SEQ ID NO:8:

```
Pro  Arg  Val  Val  Pro  Asp  Gln  Arg  Ser  Lys  Phe  Glu  Asn  Glu  Glu  Phe
 1                  5                       10                      15

Phe  Arg  Lys  Leu  Ser  Arg  Glu  Cys  Glu  Ile  Lys  Tyr  Thr  Gly  Phe  Arg
                20                       25                      30

Asp  Arg  Pro  His  Glu  Glu  Arg  Gln  Ala  Arg  Phe  Gln  Asn  Ala  Cys  Arg
           35                       40                      45

Asp  Gly  Arg  Ser  Glu  Ile  Ala  Phe  Val  Ala  Thr  Gly  Thr  Asn  Leu  Ser
     50                       55                      60

Leu  Gln  Phe  Phe  Pro  Ala  Ser  Trp  Gln  Gly  Glu  Gln  Arg  Gln  Thr  Pro
 65                      70                       75                      80

Ser  Arg  Glu  Tyr  Val  Asp  Leu  Glu  Arg  Glu  Ala  Gly  Lys  Val  Tyr  Leu
                85                       90                      95

Lys  Ala  Pro  Met  Ile  Leu  Asn  Gly  Val  Cys  Val  Ile  Trp  Lys  Gly  Trp
               100                      105                     110

Ile  Asp  Leu  Gln  Arg  Leu  Asp  Gly  Met  Gly  Cys  Leu  Glu  Phe  Asp  Glu
          115                      120                     125

Glu  Arg  Ala  Gln  Gln  Glu  Asp  Ala  Leu  Ala  Gln  Gln  Ala  Phe  Glu  Glu
     130                      135                     140

Ala  Arg  Arg  Arg  Thr  Arg  Glu  Phe  Glu  Asp  Arg  Asp  Arg  Ser  His  Arg
145                      150                     155                     160

Glu  Glu  Met  Glu  Val  Arg  Val  Ser  Gln  Leu  Leu  Ala  Val  Thr  Gly  Lys
               165                      170                     175

Lys  Thr  Thr  Arg  Pro
               180
```

( 2 ) INFORMATION FOR SEQ ID NO:9:

( i ) SEQUENCE CHARACTERISTICS:
        ( A ) LENGTH: 754 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
        ( A ) CHROMOSOME/SEGMENT: 16

( i x ) FEATURE:
        ( A ) NAME/KEY: CDS
        ( B ) LOCATION: 1..543

( x i ) SEQUENCE DESCRIPTION: SEQ ID NO:9:

```
CCG  CGC  GTC  GTG  CCC  GAC  CAG  AGA  AGC  AAG  TTC  GAG  AAC  GAG  GAG  TTT       48
Pro  Arg  Val  Val  Pro  Asp  Gln  Arg  Ser  Lys  Phe  Glu  Asn  Glu  Glu  Phe
 1               5                        10                       15

TTT  AGG  AAG  CTG  AGC  CGC  GAG  TGT  GAG  ATT  AAG  TAC  ACG  GGC  TTC  AGG       96
Phe  Arg  Lys  Leu  Ser  Arg  Glu  Cys  Glu  Ile  Lys  Tyr  Thr  Gly  Phe  Arg
              20                        25                       30

GAC  CGG  CCC  CAC  GAG  GAA  CGC  CAG  GCA  CGC  TTC  CAG  AAC  GCC  TGC  CGC      144
Asp  Arg  Pro  His  Glu  Glu  Arg  Gln  Ala  Arg  Phe  Gln  Asn  Ala  Cys  Arg
              35                        40                       45

GAC  GGC  CGC  TCG  GAA  ATC  GCT  TTT  GTG  GCC  ACA  GGA  ACC  AAT  CTG  TCT      192
Asp  Gly  Arg  Ser  Glu  Ile  Ala  Phe  Val  Ala  Thr  Gly  Thr  Asn  Leu  Ser
     50                        55                        60

CTC  CAA  TTT  TTT  CCG  GCC  AGC  TGG  CAG  GGA  GAA  CAG  CGA  CAA  ACA  CCT      240
Leu  Gln  Phe  Phe  Pro  Ala  Ser  Trp  Gln  Gly  Glu  Gln  Arg  Gln  Thr  Pro
 65                       70                        75                       80

AGC  CGA  GAG  TAT  GTC  GAC  TTA  GAA  AGA  GAA  GCA  GGC  AAG  GTA  TAT  TTG      288
Ser  Arg  Glu  Tyr  Val  Asp  Leu  Glu  Arg  Glu  Ala  Gly  Lys  Val  Tyr  Leu
                    85                        90                       95

AAG  GCT  CCC  ATG  ATT  CTG  AAT  GGA  GTC  TGT  GTT  ATC  TGG  AAA  GGC  TGG      336
Lys  Ala  Pro  Met  Ile  Leu  Asn  Gly  Val  Cys  Val  Ile  Trp  Lys  Gly  Trp
               100                      105                     110

ATT  GAT  CTC  CAA  AGA  CTG  GAT  GGT  ATG  GGC  TGT  CTG  GAG  TTT  GAT  GAG      384
Ile  Asp  Leu  Gln  Arg  Leu  Asp  Gly  Met  Gly  Cys  Leu  Glu  Phe  Asp  Glu
              115                      120                     125

GAG  CGA  GCC  CAG  CAG  GAG  GAT  GCA  TTA  GCA  CAA  CAG  GCC  TTT  GAA  GAG      432
Glu  Arg  Ala  Gln  Gln  Glu  Asp  Ala  Leu  Ala  Gln  Gln  Ala  Phe  Glu  Glu
     130                      135                      140

GCT  CGG  AGA  AGG  ACA  CGC  GAA  TTT  GAA  GAT  AGA  GAC  AGG  TCT  CAT  CGG      480
Ala  Arg  Arg  Arg  Thr  Arg  Glu  Phe  Glu  Asp  Arg  Asp  Arg  Ser  His  Arg
145                      150                      155                     160

GAG  GAA  ATG  GAG  GTG  AGA  GTT  TCA  CAG  CTG  CTG  GCA  GTA  ACT  GGC  AAG      528
Glu  Glu  Met  Glu  Val  Arg  Val  Ser  Gln  Leu  Leu  Ala  Val  Thr  Gly  Lys
                    165                      170                     175

AAG  ACA  ACA  AGA  CCC  TAGTCCTGGT  TCCAATTTAG  GTGGTGGTGA  TGACCTCAAA            583
Lys  Thr  Thr  Arg  Pro
               180

CTTCGTTAAT  TAATAGCACA  GCAGATGTGT  GCTGCCCATC  TTTACATACA  CATTGCTTCT             643

AGTTGGCAGA  AATAATTGAT  TAAAAGACCA  GAAACTGTGA  TAACTGGAGG  TACTACGGTC             703

TATTTCTCAA  CCTTAGGCAG  TAATAGACAT  CACAAACTGC  CATGGTTTTG  C                      754
```

( 2 ) INFORMATION FOR SEQ ID NO:10:

( i ) SEQUENCE CHARACTERISTICS:
        ( A ) LENGTH: 181 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Pro  Arg  Val  Val  Pro  Asp  Gln  Arg  Ser  Lys  Phe  Glu  Asn  Glu  Glu  Phe
  1              5                      10                      15
Phe  Arg  Lys  Leu  Ser  Arg  Glu  Cys  Glu  Ile  Lys  Tyr  Thr  Gly  Phe  Arg
              20                      25                      30
Asp  Arg  Pro  His  Glu  Glu  Arg  Gln  Ala  Arg  Phe  Gln  Asn  Ala  Cys  Arg
         35                      40                      45
Asp  Gly  Arg  Ser  Glu  Ile  Ala  Phe  Val  Ala  Thr  Gly  Thr  Asn  Leu  Ser
     50                      55                      60
Leu  Gln  Phe  Phe  Pro  Ala  Ser  Trp  Gln  Gly  Glu  Gln  Arg  Gln  Thr  Pro
 65                      70                      75                      80
Ser  Arg  Glu  Tyr  Val  Asp  Leu  Glu  Arg  Glu  Ala  Gly  Lys  Val  Tyr  Leu
                 85                      90                      95
Lys  Ala  Pro  Met  Ile  Leu  Asn  Gly  Val  Cys  Val  Ile  Trp  Lys  Gly  Trp
             100                     105                     110
Ile  Asp  Leu  Gln  Arg  Leu  Asp  Gly  Met  Gly  Cys  Leu  Glu  Phe  Asp  Glu
         115                     120                     125
Glu  Arg  Ala  Gln  Gln  Glu  Asp  Ala  Leu  Ala  Gln  Gln  Ala  Phe  Glu  Glu
     130                     135                     140
Ala  Arg  Arg  Arg  Thr  Arg  Glu  Phe  Glu  Asp  Arg  Asp  Arg  Ser  His  Arg
145                     150                     155                     160
Glu  Glu  Met  Glu  Val  Arg  Val  Ser  Gln  Leu  Leu  Ala  Val  Thr  Gly  Lys
                 165                     170                     175
Lys  Thr  Thr  Arg  Pro
             180
```

( 2 ) INFORMATION FOR SEQ ID NO:11:

( i ) SEQUENCE CHARACTERISTICS:
        ( A ) LENGTH: 22 nucleotides
        ( B ) TYPE: nucleic acid
        ( C ) STRANDEDNESS: double
        ( D ) TOPOLOGY: linear ( i i ) MOLECULE TYPE: oligonucleotide primer ( x i ) SEQUENCE DESCRIPTION: SEQ ID NO:11:

GGT TAA ATT GAC TGA AGG CAC C        22

( 2 ) INFORMATION FOR SEQ ID NO:12:

( i ) SEQUENCE CHARACTERISTICS:
        ( A ) LENGTH: 20 nucleotides
        ( B ) TYPE: nucleic acid
        ( C ) STRANDEDNESS: double
        ( D ) TOPOLOGY: linear ( i i ) MOLECULE TYPE: oligonucleotide primer ( x i ) SEQUENCE DESCRIPTION: SEQ ID NO:12:

ATG CAT CCA AAC TCG GGA TA        20

( 2 ) INFORMATION FOR SEQ ID NO:13:

(i) SEQUENCE CHARACTERISTICS:
 (A) LENGTH: 18 nucleotides
 (B) TYPE: nucleic acid
 (C) STRANDEDNESS: double
 (D) TOPOLOGY: linear (ii) MOLECULE TYPE: oligonucleotide primer (xi) SEQUENCE DESCRIPTION: SEQ ID NO:13:

TTT GCG GCC GGA ACC GAC                                    18

(2) INFORMATION FOR SEQ ID NO:14:

(i) SEQUENCE CHARACTERISTICS:
  (A) LENGTH: 20 nucleotides
  (B) TYPE: nucleic acid
  (C) STRANDEDNESS: double
  (D) TOPOLOGY: linear (ii) MOLECULE TYPE: oligonucleotide primer (xi) SEQUENCE DESCRIPTION: SEQ ID NO:14:

GCT CCG GAT CCC TAG AGA AA                                 20

MARKERS FOR DETECTION OF CHROMOSOME 16 REARRANGEMENTS

This is a continuation of U.S. patent application Ser. No. 08/099,869, filed Jul. 29, 1993, entitled "Markers for Detection of Chromosome 16 Rearrangements," by Pu Liu et al now abandoned.

FIELD OF THE INVENTION

The present invention relates generally to the genes involved in the chromosome 16 rearrangement associated with acute myeloid leukemia. More specifically, the present invention relates to the inversion 16 fusion gene. The present invention is also directed to the diagnoses and assessment of treatment for acute myeloid leukemia.

BACKGROUND OF THE INVENTION

Non-random chromosomal abnormalities have been identified in many hematologic malignancies. Cloning of the breakpoints involved in the abnormalities has led to the identification of the affected genes and the molecular genetic consequences of the rearrangements. Known proto-oncogenes have been found to be deregulated by translocations and new biomedically important genes have been identified at the breakpoints with resultant insights into the mechanisms of normal hematopoiesis as well as leukemogenesis. Solomon, E. et al., *Science* 254:1153 (1991); Nichols, J. et al. *Blood* 80:2953 (1992); Rabbits T. H., *Cell* 67:641 (1991); and Yunis, J. J. et al., *Crit. Rev. Oncogen.* 4:161 (1993). In leukemias, at least two mechanisms have been identified for the deregulation of cellular proto-oncogenes by chromosome rearrangements. The first is the juxtaposition of a cellular proto-oncogene to the regulatory elements of a tissue specific gene, particularly the immuno-globulin and T cell receptor genes, leading to the inappropriate expression of the oncogene. Leder, P. et al., *Science* 222:765 (1983); Finger, L. R. et al., *Science* 234:982 (1986). The second is gene fusion at the junction of a translocation, generating a chimeric mRNA and a protein with transforming properties. Borrow, A. D. et al., *Science* 249:1577 (1990) and de Thé, H. et al., *Nature* 347:558 (1990).

A characteristic chromosome 16 pericentric inversion, inv(16)(p13q22), has been found in almost all patients with abnormal bone marrow eosinophilia (M4Eo), which constitutes about 8% of acute myeloid leukemia (AML) patients. Arthur, D. C. et al., *Blood* 61:994 (1983); LeBeau, M. M. et al., *N. Engl. J. Med.* 309:630 (1983); Mitelman, F. et al., *Genes Chrom. Cancer* 5:57 (1992); Heim, S. et al., *Can. Suppl.* 70:1701 (1992). Given the absence of other karyotypic abnormalities in many of these patients and the fact that patients treated in several studies had the inversion chromosome disappear upon remission, a pathogenic relationship between inversion 16 and acute myelomonocytic leukemia (AMML) M4Eo has been suggested. Arthur, D. C. et al., *Blood* 61:994 (1983); LeBeau, M. M. et al., *N. Engl. J. Med.* 309:630 (1983); Mitelman, F. et al., *Genes Chrom. Cancer* 5:57 (1992); Heim, S. et al., *Can. Suppl.* 70:1701 (1992); "Fourth International Workshop on Chromosomes in Leukemia, 1982," *Can. Genet. Cytogen.* 11:275 (1984); and Bennett, J. M. et al., *Ann. Intern. Med.* 103:626 (1985).

The breakpoints associated with this chromosome rearrangement had not, however, been previously cloned. Genetic events associated with this chromosomal aberration and their relationship to leukemogenesis, therefore, remained unidentified, although some progress in identifying the molecular events associated with inversion 16 (also referred to as inv(16) herein) was made. For instance, the long arm breakpoint of inv(16) was mapped between two anonymous DNA sequence markers found to be within 450 kb from each other. Callen, D. F. et al., *Am. J. Hum. Genet.* 51:A57 (1992). By fluorescence in situ hybridization (FISH), the p arm breakpoint was mapped between anonymous cosmids located in band 16p13.13 separated by an unknown distance. Wessels, J. W. et al., *Blood* 77:1555 (1991) It was also suggested that the breakpoint was within a chromosome 16-specific repeat sequence which might play a role in the origin of chromosome 16 rearrangements in the leukemia. Dauwerse, J. G. et al., *Blood* 79:1299 (1992) and Stallings, R. L. et al., *Genomics* 13:332 (1992).

Sensitive molecular analysis has also not been available for diagnosis and monitoring of patients with inv(16) leukemia. Identification of the inversion has generally been performed with karyotyping by G-banding. This procedure however, is not very sensitive due to the poor quality of clinical samples and the fact that chromosome 16 is a short chromosome with few identifiable banding landmarks. A more recent diagnostic method utilizes isolated cosmids as probes to identify the chromosome 16 inversion by FISH. Although this is an improvement over karyotyping, problems with chromosome preparation from clinical samples still exist and all of the cytogenetic-based diagnoses are not sensitive to a small fraction of abnormal cells, i.e. are not helpful for monitoring for relapse.

It would therefore be desirable to identify the genes involved in the chromosome 16 arrangement. It would also be desirable to provide markers for the detection of chromosome 16 rearrangements. It would further be desirable to provide a method of diagnosing chromosome 16 rearrangements. It would also be desirable to provide a method of assessing treatment of acute myeloid leukemia patients. With the elucidation of the genes and breakpoints involved, conventional and genetic therapeutic approaches for the treatment of acute myeloid leukemia are also now feasible.

SUMMARY OF THE INVENTION

The breakpoints of the pericentric inversion of chromosome 16 have now been cloned and the genes at each breakpoint identified. On 16q, the inversion occurs near the end of the coding region for CBFβ, a subunit of a novel heterodimeric transcription factor regulating genes expressed in T cells. The nucleotide sequence and coding region of human CBFB (the gene for CBFβ) and their corresponding amino acid sequences are set forth in SEQ ID NOs: 7, 9 and SEQ ID Nos: 8, 10 respectively. On 16p, a smooth muscle myosin heavy chain (SMMHC) gene MYH11, is interrupted. The sequence for MYH11 has been previously reported in Matsuoka, R. et al., *Am. J. Med. Genet.* 46:61 (1993).

Several forms of an inversion 16 fusion gene and gene product have also been identified and sequenced. The nucleic acid sequences of inversion 16 fusion genes and their corresponding predicted amino acid sequences are set forth in SEQ ID NOs: 1, 3, 5 and SEQ ID NOs: 2, 4, 6, respectively. The predicted inversion 16 fusion gene product comprises the first 164 amino acids of CBFβ connected to the tail region of SMMHC.

With the identification and sequencing of the inversion gene and its corresponding gene product, nucleic acid probes and antibodies raised to the inversion product may be used within the scope of the invention in a variety of hybridization and immunological assays to screen for the presence or absence of inversion 16 gene and gene product.

Polymerase chain reaction (PCR) primers have also been produced which are capable of detecting novel gene product generated by the chromosome inversion. Functional assays to measure levels of gene function can also be employed for diagnosis or to monitor treatment progress. Assay kits for such screening and diagnosis in accordance with the principles of the invention are also provided. Therapeutic approaches, including gene therapy, also now become a possibility.

By the term "gene" is meant a nucleic acid, either genomic or synthetic, which encodes a protein product. The term "nucleic acid" as used herein is intended to mean natural or synthetic linear and sequential arrays of nucleotides and nucleosides, e.g. in cDNA, genomic DNA (gDNA), mRNA, and RNA, oligonucleotides, oligonucleosides, and derivatives thereof. The term "synthetic oligonucleotide" refers to an artificial nucleic acid (e.g. a chemically synthesized nucleic acid) having a sufficient number of nucleotides which will specifically hybridize to complementary sequences under stringent conditions; that is, from at least 10 nucleotides, but generally eighteen or more nucleotides. In addition, the term "encoding" is intended to mean the subject nucleic acid may be transcribed and translated into either the desired polypeptide or the subject protein in an appropriate expression system, e.g. when the subject nucleic acid is linked to appropriate control sequences such as promoter and enhancer elements in a suitable vector (e.g. an expression vector) and when the vector is introduced into an appropriate system or cell. The term "polypeptide" is used to mean three or more amino acids linked in a serial array. The term "fragment" as referred to herein with reference to nucleic acid (e.g., cDNA, genomic DNA, (gDNA)) is used to mean a portion of the subject nucleic acid such as constructed artificially (e.g., through chemical synthesis) or by cleaving a natural product into a multiplicity of pieces (e.g., with a nuclease or endonuclease to obtain restriction fragments). By "substantially as shown" or "substantially similar" with respect to a nucleic acid is meant sufficiently similar in structure or sequence to encode the desired polypeptide or protein product, or with respect to a polypeptide sufficiently similar in structure or sequence to serve its principal function.

The term "capable of hybridizing under stringent conditions" is used to mean annealing a first nucleic acid is capable of annealing to a complementary second nucleic acid under stringent conditions (described below). For example, the first nucleic acid may be a sample of denatured DNA derived from patient cells, and the second nucleic acid may be a denatured cDNA of inversion 16 fusion gene. Hybridization under stringent conditions includes, e.g., high temperature and/or low salt content, which tend to disfavor hybridization of dissimilar nucleotide sequences. A suitable protocol involves hybridization in 6×SSC at 42° C. in hybridization solution containing formamide, followed by washing with 1×SSC at 55° C. Other experimental conditions for controlling stringency are described in Maniatis, T., et al., *Molecular Cloning; A Laboratory Manual*, Cold Springs Harbor Laboratory, Cold Springs, N.Y., 1982, at pages 387–389; and also in Sambrook, Fritsch, and Maniatis, *Molecular Cloning; A Laboratory Manual, Second Edition*, Volume 2, Cold Springs Harbor Laboratory, Cold Springs, N.Y., 1989, pages 8.46–8.47. It will be appreciated, however, that although reference herein is made to nucleic acids or olignucleotides capable of hybridizaing under stringent conditions, hybridization in the practice of the invention need not actually be conducted under such conditions.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

BRIEF DESCRIPTION OF THE SEQUENCE LISTING

Figure 1A:
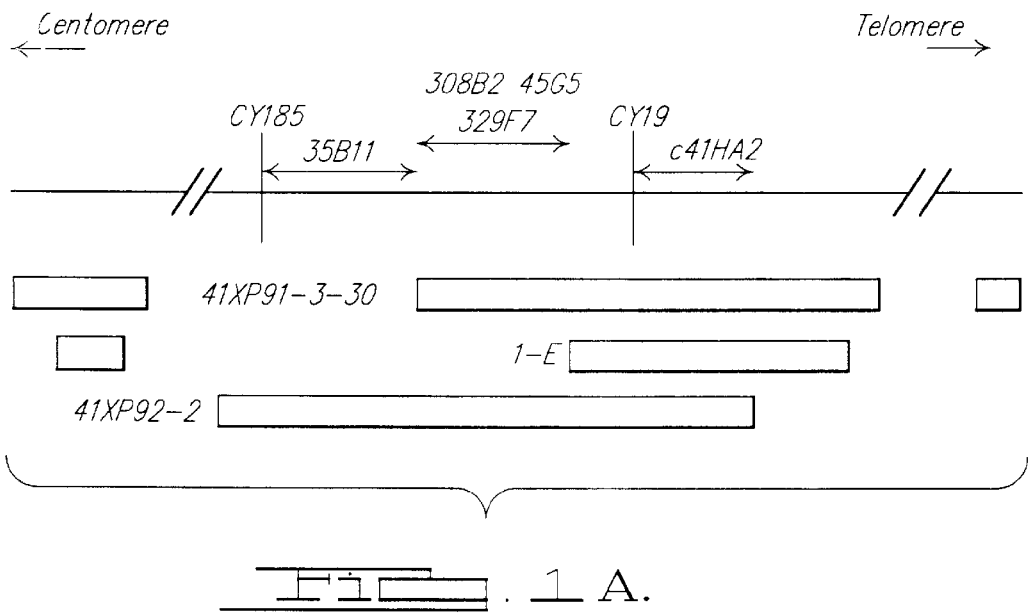
FIGS. 1A and 1B are diagrammatic representations of the locations of the human genomic chromosome 16p content of hybrid cells and recombinant clones.

SEQ ID NOs: 1, 3 and 5 represent nucleotide sequences for inv(16) fusion proteins consisting of sequence from the human CBFB (HCBFB) gene and the human MYH11 gene, as described herein. Polymerase chain reaction (PCR) was performed on total cellular RNA from the AMML cell line ME-1, which has inv(16) and is of the M4 subtype, and peripheral leukemia cells of five AMML patients with inv (16), and the sequence of the PCR products is shown.

An initiator AUG coding should precede the nucleotide sequences shown in SEQ ID NOs: 1, 3, 5, 7 and 9 and should thus be present at nucleotide postions −3, −2 and −1 of these sequences. In the ME-1 cell line and all patients examined thus far, the inv(16) breakpoint in HCBFB has been a nucleotide 492. The inv(16) breakpoint of the MYH11 gene, however, has been variable. Three patients and the ME-1 cell line all had the inv(16) sequence shown in SEQ ID NO: 1 (Samples 3–6), in which nucleotides 1 to 492 of the HCBFB genes are fused to MYH11 at nucleotide 1921 of MYH11.

One patient (sample 1) had the inv(16) sequence shown in SEQ ID NO: 3, in which nucleotides 1 to 492 of HCBFB are fused to MYH11 at nucleotide 994 of MYH11. Another patient (sample 2) had the inv(16) sequences shown in SEQ ID NO: 5, in which nucleotides 1 to 492 of HCBFB are fused to MYH11 at nucleotide 1201 of MYH11.

SEQ ID NOs: 2, 4 and 6 represent the predicted amino acid sequences corresponding to the nucleotide sequences in SEQ ID NO: 1, 3 and 5, respectively.

SEQ ID NO: 7 represents the nucleotide sequence of the HCBFB gene. The sequence for nucleotides 1 to 75 of HCBFB is derived form the sequencing of PCR products form AMML patient RNA. The remainder of the sequence, nucleotides 76 to 2883, is derived from the sequencing of clone RL9a, a cDNA clone isolated from a HeLa cell library, as described herein. SEQ ID NO: 8 represents the predicted amino acid sequence of the HCBFB gene.

SEQ ID NO: 9 corresponds to the sequence of nucleotides 1 to 754 of HCBFB, which represents its coding region. This sequence is derived from sequencing of PCR products derived from AMML patient RNA. SEQ ID NO: 10 represents the predicted amino acid sequence corresponding to the nucleotide sequence.

SEQ ID NOs: 11–14 represent the nucleotide sequences of oligonucleotide primers used in polymerase chain reactions for screening libraries.

DETAILED DESCRIPTION OF THE PREFERRED EMBODIMENTS

The 16p and 16q breakpoints involved in the pericentric inversion of chromosome 16 have been cloned. The gene CBFB, coding for CBFβ which is involved in the 16q breakpoint, has been identified and sequenced. The gene MYH11, coding for SMMHC which is involved in the 16p breakpoint, has also been identified. Several forms of an inv(16) fusion gene containing portions of both CBFB and MYH11 have also been identified and sequenced.

The present invention results in immediate as well as long-term potential applications for the management and understanding of the basis of the inv(16) problem. Previously, standard G-band cytogenetics for diagnosis of the malady was difficult given the clarity of marrow metaphase preparations and the subtle nature of the differences between the inversion and normal chromosomes. The use of fluorescence in situ hybridization (FISH) for the detection of the separation of cosmid probes located on either side of the breakpoint on the p arm (Dauwerse, J. G. et al., *Cytogen. Cell Genet.* 53:126 (1990)), though useful, is also difficult in all but the most sophisticated experimental cytogenetic laboratories because of weak signal and background problems associated with such small FISH probes. The bright, specific signals provided by either hybrid 41XP91-3-30, or YACs y757D7 or y854E2, are useful for the rapid and unambiguous identification of inv(16) in even the poorest of metaphase preparations. Furthermore, with the sequencing of the human CBFB gene, diagnostic as well as therapeutic applications are now possible.

The present invention also impacts on the present hypothesis suggesting that CH16LARs located on the p and q arms of chromosome 16 might play a role in the origin of the chromosome 16 rearrangements in AMML-M4. Dauwerse, J. G. et al., *Blood* 79:1299 (1992); Stallings, R. L. et al., *Genomics* 13:332 (1992). While there is some evidence of hybridization on the q arm using the largest (and therefore farthest reaching) of the YACs, the smaller YACS containing the inversion breakpoint and the 120 kb cosmid contig just proximal to it, do not produce FISH signals on the q arm. Since all known cosmid and YAC clones that contain CH16LARs produce FISH signals on both arms of chromosome 16 (Dauwerse, J. G. et al., *Blood* 79:1299 (1992); Stallings, R. L. et al., *Genomics* 13:332 (1992)) the repeats do not appear to be at or immediately adjacent to the p arm breakpoint. Therefore, a role for CH16LARs in the genesis of the inversion has become a less compelling hypothesis. The possibility that movement of CH16LARs from the p to q arm has some unknown position effect on genes remains another hypothesis.

The molecular cloning of the genomic DNA overlapping the breakpoints was a significant step in pinpointing the 16p and 16q breakpoints and identifying the two genes involved in the chromosomal rearrangement. As discussed above, it is now known that on 16q, the inversion occurs near the end of the coding region for CBFβ and on 16p the coding region for SMMHC is interrupted. The CBFβ protein does not contain any known DNA-binding motifs or transcriptional activation domains, and no significant homology is found to any gene or protein in GenBank. In vitro analysis shows that the mouse CBFβ/PEBP2β does not appear to bind to DNA sequences directly; rather it forms a heterodimeric complex with CBFα or PEBP2α, and stabilizes the interaction of the a with DNA. Wang, S. et al., *Mol. Cell. Biol.* 13:3324 (1993) and Ogawa, E. et al., *Virol.* 194:314 (1993). CBFα has been shown to be identical to AML1, the gene found to be disrupted in the characteristic t(8;21) translocation in the M2 subtype of AML. Wang, S. et al., *Mol. Cell. Biol.* 13:3324 (1993).

This is the first demonstration that separate subunits of a transcription factor can be involved in different leukemias. CBF must be crucial for the control of cell division and/or differentiation of the myeloid lineage since the expression of either subunit as a fusion protein leads to the blockage of differentiation and uncontrolled expansion of leukemia cells. Cytologically the two types of AMLs in which inv(16) and t(8;21) take place are different: inv(16) is a highly specific marker for the M4Eo subtype of AMML, which shows both granulocytic and monocytic differentiation and is characterized by abnormal eosinophilia in bone marrow and peripheral blood, whereas t(8;21) is highly predictive for the M2 subtype of AML which is characterized by granulocyte maturation. "Fourth International Workshop on Chromosomes in Leukemia, 1982," *Can. Genet. Cytogen.* 11:275 (1984) and Rowley, J. D., *Annal. Genet.* 16:109 (1973). Both types of leukemia have a relatively favorable prognosis.

The consistent involvement of the MYH11 gene suggests that both partners in the fusion event play a significant role. Muscle genes have been found to be fused to oncogenes in at least two reports: one between actin and the v-fgr oncogene, the other between tropomyosin and the trk oncogene. Naharro, G. et al., *Science* 223:63 (1984) and Martin-Zanca, D. et al., *Nature* 319:743 (1986). In both events, which represented isolated occurrences, truncated muscle genes were fused to a tyrosine kinase. However, neither of these two muscle gene components were found to be indispensable for the transforming capability of the oncogenes, and the actin part of the v-fgr gene actually inhibits the kinase and its transforming activity. Oskam, R. et al., *PNAS (USA)* 85:2964 (1988) and Sugita, K. et al., *J. Virol.* 63:1715 (1989).

It is not immediately apparent, therefore, what the contribution of the MYH11 gene is to the pathogenesis of inv(16) leukemia. All three breakpoints in MYH11 described herein are located in the conserved tail or rod region. This tail region of the protein contains a repeated α-helical structure, the major function of which is to form a coiled coil with another molecule in the assembly of a myosin thick filament. Kiehart, D. P., *Cell* 60:347 (1990); Nagai, R. et al., *PNAS USA* 85:1047 (1988). In six of six inv(16) patient samples an in-frame fusion mRNA was demonstrated which connects the RNA encoding the first 164 (165 including predicted initiation codon) amino acids of CBFβ with RNA encoding the tail region of SMMHC. The repeated coiled coil of SMMHC could therefore result in dimerization of two CBFβ-SMMHC molecules whereas the normal CBFβ is thought to function as a heterodimer with CBFα or PEBP2β. Speck, N. A. et al., *Mol. Cell. Biol.* 7:1101 (1987); Redondo, J. M. et al., *Mol.Cell. Biol.* 12:4817 (1992); Speck, N. A. et al., *Genes Dev.* 4:233 (1990); Wang, S. et al., *Mol. Cell. Biol.* 12:89 (1992); Kamachi, Y. et al.,*J. Virol.* 64:4808 (1990); Ogawa, E. et al., *Virol.* 194:314 (1993); Bae, S. C. et al., *Oncogene* 8:809 (1993). There are several possible mechanisms whereby this could result in a dominant transforming phenotype. The dimerized CBFβ-SMMHC protein may be able to form a more stable complex with the α subunits than that formed by wild type CBFβ, augmenting the effect of this complex on the target genes. Conversely, the CBFβ-SMMHC dimer may have a dominant-negative effect by binding a subunits with high affinity, preventing binding of the DNA target sequence. It is also possible that the SMMHC protein contributes a domain which results in inappropriate transcriptional regulation by the α/β complex. Finally, the CBFβ-SMMHC dimers may acquire some wholly new activity in transcriptional regulation.

The elucidation of these two genes as the fusion partners in an inversion leading to a common form of adult leukemia also allows for the development of a mouse model and a sensitive RT-PCR test for specific diagnosis and assessment of residual disease after treatment which are both contemplated by the present invention. The understanding of the mechanisms by which CBFβ-SMMHC transforms a particular hematopoietic lineage also leads to new and more effective therapies for this form of leukemia.

The following Specific Examples further describe the present invention.

SPECIFIC EXAMPLE 1

YEAST ARTIFICIAL CHROMOSOMES CONTAINING INVERSION-16P ARM BREAKPOINT

In the process of regional mapping of the human DNA excision repair gene ERCC4, human x UV41 hybrids were identified as containing portions of human chromosome 16p arm, overlapping at the position where ERCC4 is located, 16p13.13-p13.2. Liu, et al., *Mutagenesis* 8:199 (1993). Since this is also the region of the p arm breakpoint of inv(16) of AMML (Wessels, J. W. et al., *Blood* 77:1555 (1991)) the hybrids were tested to determine if they contained the inversion breakpoint region. Inter-Alu-PCR was performed with DNA from three hybrids which had little human DNA in them except the 16p region 41XP91-3-30, 1-E and 41XP92-2. The location of these regions is set forth in FIG. 1A, which is further discussed below.

Figures 2A, 2B, 2C, 2D, 2E, 2F:
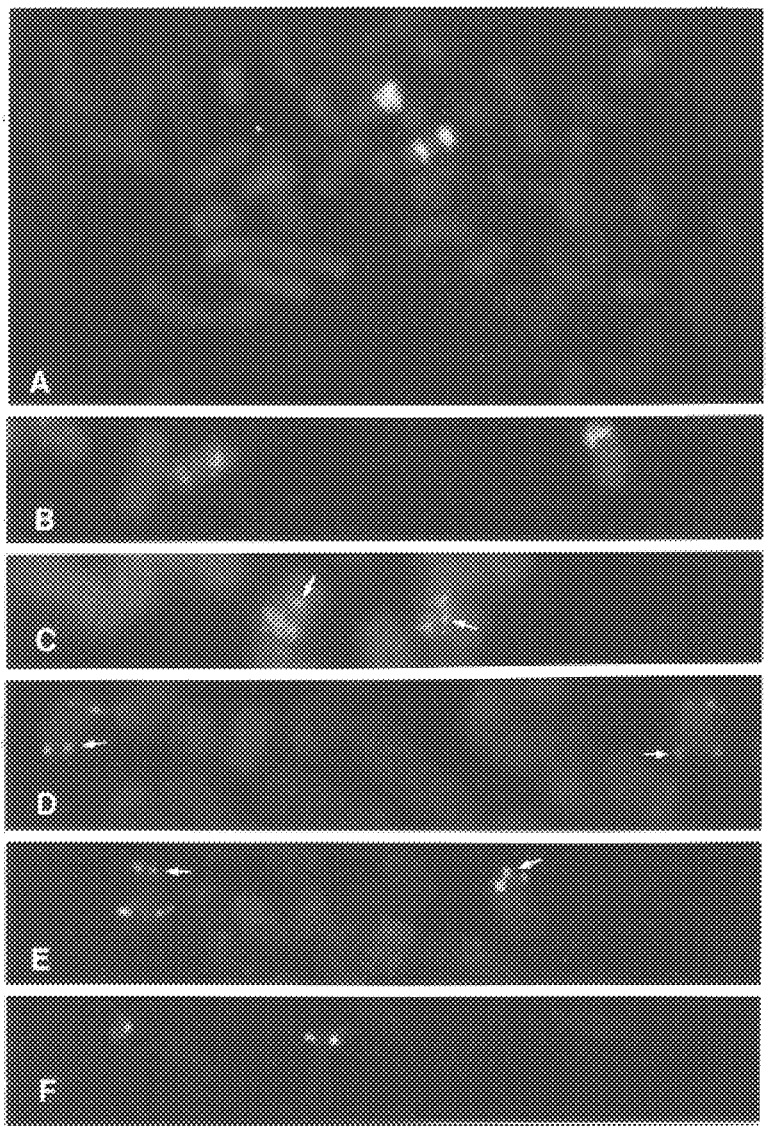
FIGS. 2A through 2L are fluorescent in situ hybridization (FISH) photomicrographs using inter-Alu-PCR products from interspecific somatic cell hybrids and YACs, as well as directly labelled cosmid DNAs as probes on inv(16) and normal cells.

The PCR products were labeled with biotin and used as competitive FISH probes (Lui, P. et al., *Can. Gen. Cytogen.* 65:93 (1993)) on metaphases from normal lymphocytes and leukemia cells from the patients with inv(16). FIGS. 2A through 2L set forth the FISH photomicrographs using inter-Alu-PCR products from interspecific somatic cell hybrids (A,B,C) and YACs (H,I,J) as well as directly labeled cosmid DNAs (D,E,F,G) as probes. FIG. 2A shows probe from hybrid 41xP91-3-30 on a bone marrow metaphase of patient 1. FIG. 2B shows a probe from hybrid 41xP92-2 on similar material. 41XP91-3-30 contained segments from the proximal, middle and distal portions of the 16p arm. Therefore, probe from this hybrid brightly identified the entire p arm of the normal chromosome (Liu, et al., *Mutagenesis* 8:199 (1993)) and, as expected, was split by the inversion, readily distinguishing the inversion chromosome with bands of fluorescence on the resultant p and q arms. As shown in FIG. 2B, signal from 41XP92-2, containing only DNA from the ERCC4 region, was also split by the inversion indicating that it also contained the p arm inversion breakpoint.

FIG. 2C shows a probe from 1-E on inv(16) cells. Probe from this hybrid identifies two zones of hybridization on normal human chromosome 16p arms, one on the distal edge of the centromere and the other in the region of ERCC4 (16p13.13-13.2). (Liu, P. et al., *Mutagenesis* 8:199 (1993)). The arrows in FIG. 2C lie in the longitudinal planes of the chromosomes and point at a region of hybridization adjacent to the centromere. In patient cells, the distance between that centromere-associated spot and the ERCC4 region is increased in one of the chromosomes (the one on the left in FIG. 2C) indicating that, as a result of the inversion the spot adjacent to the centromere is swung to the q arm. As shown in FIG. 2C, the two p arm resolvable signals visualized by probe from 1-E, one from just distal to the centromere and the other from the ERCC4 region, were separated by the inversion, placing the p arm breakpoint proximal to ERCC4 and the ERCCR region retained in hybrid 1-E.

Figures 2G, 2H, 2I, 2J, 2K, 2L:
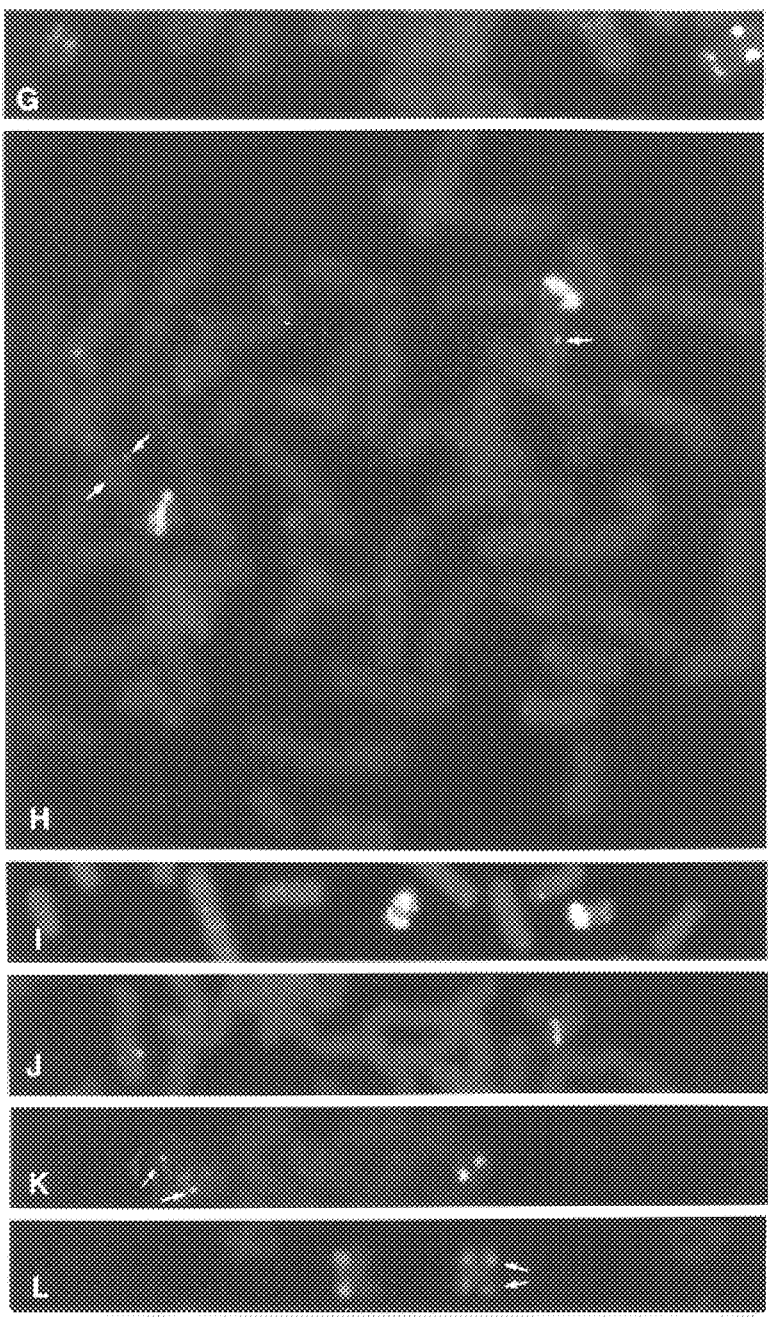

Using as markers a pair of cosmids, 327A7 and 309D3, mapped to the distal tip of the q arm on inversion 16 cells in partial metaphase (data not shown), the position of the series of p arm cosmids relative to the inversion breakpoint were determined by FISH. They were tested on the ME-1 cell line which is derived from a patient with AMML, M4Eo and inv(16), and representative patient cell preparations. FIG. 2D shows a probe from c41HA2 combined with the cosmids. The arrows in FIG. 2D indicate the positions of the q arm markers. On both the normal and inversion 16 chromosome, c41HA2 remains separated from the q arm markers indicating that it is distal to the p arm inversion breakpoint. Similar results were obtained with cosmids 308B2, 45G5, and 329F7. Signal form cosmids located distal to the breakpoint should remain on the p arm well-separated from the q arm markers such that the patten of hybridization on the inversion chromosome should be indistinguishable from the normal chromosome in cell. FIG. 2E shows probe from 35B11 combined with q arm marker cosmids (the arrows again indicating the position of markers) on inv( 16) cells in a partial metaphase. On the chromosome 16 on the right, the signals are clustered indicating that the region identified by 35B11 has been brought adjacent to the q arm markers.

c41HA2 is in an interval of human chromosome 16 distal to the portion of the chromosome contained in hybrid CY19 of the Callen chromosome 16 hybrid mapping panel. Callen, D. F. et al., *Genomics* 13:1178 (1992). Therefore, a series of cosmids that had been shown (Stallings, R. L. et al., *Genomics* 13:1031 (1992)), to be members of different cosmid-contigs located proximal to CY19 breakpoint yet distal to the next proximal interval were tested. The positions of the relevant CY breakpoints and test cosmids, relative to the regions of chromosome 16 retained in the hybrids tested for containing the inversion breakpoint, are illustrated in FIG. 1A. All cosmids tested, with the exception of 35B11, gave results identical to those of c41HA2 and were therefore located distal to the inversion breakpoint. As discussed above, only 35B11 (tested on the same patient material, ME-1 cells and cells from patients 1, 2, 4, and 5) was centromeric to the p arm inversion breakpoint in these analyses. As confirmation that probe from 35B11 identified a segment on the p arm of normal chromosome 16s, as shown in FIG. 2F, two color (35B11 yellow-green and c41HA2 red) (colors not shown) FISH indicated that 35B11 co-localized with c41HA2 on the chromosomes of normal control cells. To verify that 35B11 swung to the q arm as a result of the inversion, as shown in FIG. 2G, signals from the two cosmids were separated from each other on one of the chromosome 16s (far right vs. far left) when co-hybridized onto metaphases from patient cells.

Figure 3:
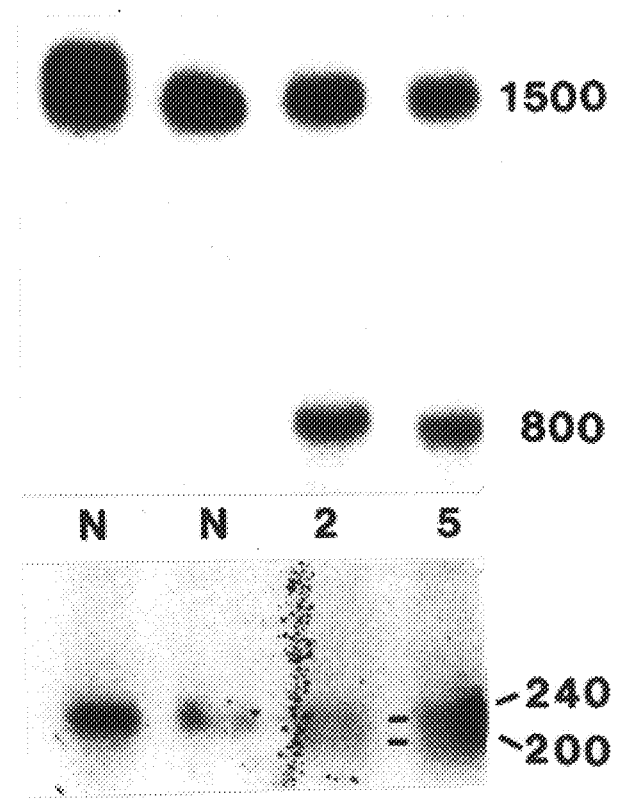
FIG. 3 is an autoradiograph of a Southern blot hybridized to a 1.2 kb repeat-free fragment from cosmid 35B11, identifying NotI and SacII macrorestriction fragments from samples from normal volunteers and patients.

Probes from representative cosmids in the CY185-CY19 interval were then used for analysis of pulsed-field-separated macrorestriction fragments from normal and leukemic cells. FIG. 3 is a Southern blot hybridization of a 1–2 kb repeat-free fragment from cosmid 35B11 identifying a novel 800 kb NotI (top panel) macrorestriction fragments from samples from two normal volunteers (n) and the leukemic cells of four patients examined, 1, 2, 4 and 5. Two of these samples, from patients 2 and 5, were similarly examined after SacII digestion (bottom panel) and were seen to have a novel 200 kb fragment in addition to the germline 240 kb fragment. Probes from the other cosmids in the region did not identify any rearranged bands with either restriction enzyme in any patient material. These data indicated that cosmid 35B11 contained DNA sequences within 240 kb of the p arm inversion breakpoint in at least some patients. Since this cosmid has been identified as nested within a 120 kb, ten-member cosmid contig at the Los Alamos National Laboratory (Claxton, D. F. et al., *Blood* 80:582 (1992)) cosmids (43F6 and 46C7) at or near the two opposite ends of the contig (FIG. 1B) were then used as FISH probe on inv(16) cells. Both gave results identical to 35B11 indicating that the entire 120 kb contig did not contain, but was centromeric to, the p arm inversion breakpoint.

Therefore, cosmids 43F6 and 46C7 were used to identify YACs containing human genomic DNA that might span the breakpoint. Several hundred base pairs from each of the two ends of both cosmids were sequenced from the two vector arms (T3 and T7) into the inserts. From these four sequences, PCR primer pairs were designed lone pair from each end of each of the two cosmids). Each of the four primer pairs was tested on each of the cosmids of the contig. The primer pair at the T3 end of 43F6 (43G6-T3) was found to be unique to this cosmid whereas the pair at the T7 end could amplify from adjacent cosmids in the contig. Likewise, the primer pair at the T7 end of 46C7 (46C7-T7) was unique to the cosmid and the pair at T3 end was not. Therefore, 43F6-T3 and 46C7-T7 primers are located at or near the far ends of the contig (FIG. 1B) and, therefore, were used to screen two YAC libraries (Washington University and CEPH).

Two positive YAC clones were identified from each YAC library (yB80B9 and yC8E12 from Washington University, and y854E2 and y757D7 from CEPH). The inserts measured 300 kb, 100 kb, 550 kb, and 780 kb respectively when sized on a pulsed field gel, blotted and probed with human $C_0t$-1 DNA (data not shown). All the YACs gave positive signals with primer sets from both cosmids at opposite ends of the contig except yC8E12. It was positive only for the primer set from 46C7 suggesting, as its size would predict, that it did not span the entire contig.

Inter-Alu-PCRs were performed on YAC DNAs. Products were then labeled with biotin and used as FISH probes on metaphases of normal lymphoblasts. DNA from y854E2 and yC8E12 proved to be non-chimeric by this assay giving single signals only on chromosome 16p arms. DNA from yB80B9 was found to be chimeric, since its DNA produced signals on 17p and an unidentified chromosome in addition to the single signals on 16p (data not shown). As shown in FIG. 2H, a probe from y757D7 on a normal human metaphase shows good specificity to the 16p arm with only tiny dots of hybridization (arrows in FIG. 2H) on the q arm. Thus, the DNA from y757D7 was also non-chimeric but appeared to contain the previously described (Dauwerse, J. G. et al., *Blood* 79:1299 (1992) and Stallings, R. L. et al., *Genomics* 13:332 (1992)) chromosome 16-specific low abundance repetitive sequences (CH16LARs) since inter-Alu-PCR product from it produced, in addition to the bright signal on chromosome 16p arm, the very faint pair of signals on the q arm.

As shown in FIG. 2I, despite the presence of the repeat sequences, when y757D7 was used to probe an ME-1 partial metaphase, the bright p arm signal was split between the p and q arms on the inversion chromosome. On the one where it is not split, the same faint hybridization as seen in FIG. 2H, is seen on the q arm. As expected, as shown in FIG. 2J, since yC8E12 does not span the contig which was shown to be proximal to the breakpoint, the FISH signal from probe from yC8E1 2 on an ME-1 partial metaphese was not split by the inversion in patient cells. Like probe from y757D7, probe from yB80B9 on an ME-1 partial metaphase and probe from y854E2 on a partial metaphase from patient 4, shown in FIGS. 2K and 2L, respectively, clearly detected split signal on one of the two chromosome 16s in the leukemic cells from all patients in the study as well as cell line ME-1. Thus, yB80B9, y854E2 and y757D7 contain human genomic DNA sequences that span the p arm inversion breakpoint in AMML.

The following is a more thorough description of the materials and methods employed in the above-described study.

Cell Lines and Patient Samples. A diagrammatic representation of the locations of the human genomic chromosome 16p content of hybrid cells and recombinant clones is set forth in FIG. 1A and 1B. Referring to FIG. 1A, the broken line indicates the 16p13.13-13.2 region and the positions marked by the CY19 hybrid (which contains chromosome sequences from the site marked to the end of the q arm) and by the CY185 hybrid (containing sequences from its site marked to the end of the q arm). Callen, D. F. et al., *Genomics* 13:1178 (1992). Above the line in FIG. 1A are the cosmids used, located according to their ability to identify fragments in the CY hybrids, e.g. c41HA2, does not hybridize to CY185 or CY19 (Liu, P. et al., *Mutagenesis* 8:199 (1993)) whereas the other cosmids hybridize to CY19 but not CY185. Stallings, R. L. et al., *Genomics* 13:1031 (1992). The blocks below the line in FIG. 1A indicate the regions contained in the designated hybrids.

Figure 1B:
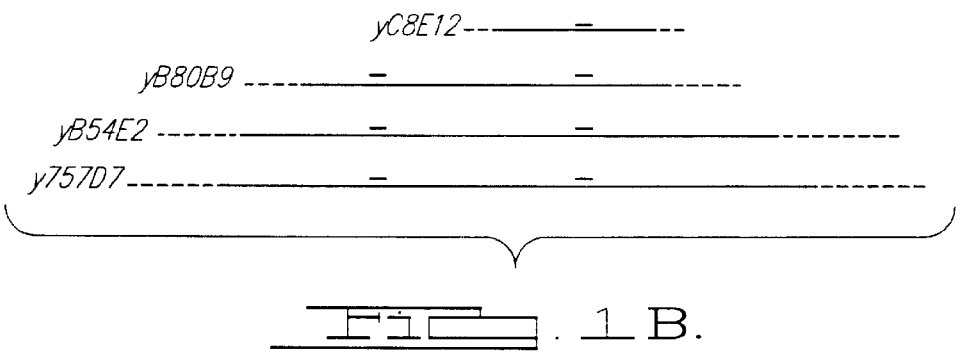

In FIG. 1B, the five short lines are a series of five cosmids which represent the tile-path of a 10 member cosmid contig containing cosmid 35B11. Positions of the 43F6-T3 and 46C7-T7 terminal primers are indicated as small horizontal bars on the appropriate cosmids. 46C7 was used as a terminal cosmid of the contig instead of 57B2 because, based on gel analysis, the latter contained vector/insert rearrangements. Positions of the isolated YACs relative to the contig and the terminal primers are indicated in the lower part of FIG. 1B.

Human x CHO somatic cell hybrids, 41XP91-3-30, 1-E, and 41XP92-2, contain different portions of the p arm of human chromosome 16, as shown in FIG. 1. A leukemic cell line, ME-1, had been established from the peripheral blood leukemia cells of an M4Eo patient with inv(16). Yanagisawa, K. et al., *Blood* 78:451 (1991). Peripheral blood cells were obtained by pheresis of six AMML patients (referred to as patient 1–6 herein) and were cryopreserved.

Vials were thawed and cells cultured for metaphase preparation or cells were embedded in agarose for DNA as described. Claxton, D. F. et al., *Blood* 80:582 (1992). Standard cytogenetics on all patients studied revealed the presence of inv16(p13;q22) in all dividing cells at presentation. In addition to this inversion, patient 2 had a t(3p;7p); patient 3 had a +22; and patient 5 had a +8. Abnormal eosinophilia was present in patients 1, 4, 5 and 6.

Cosmid Clones. Cosmid clones marking the p13.13-p13.2 region of human chromosome 16 were used to help define the inv(16) p arm breakpoint region by FISH. Cosmid c41HA2 had been defined as being closely linked to the ERCC4 locus and was isolated from a cosmid library made from hybrid 41XP91-3-30. (Liu, P. et al., *Mutagenesis* 8:199 (1993)). Cosmids of the contig identified by 35B11 were also used.

DNA Sequencing and Primer Design. Cosmid DNA was sequenced directly using T3 and T7 primers which flank the cloning site on sCos-1 (Evans, G. A. et al., *Gene* 79:9 (1989)) using the Sequenase kit (USB). Primers were designed using the PRIMER program designed and provided by Drs. E. Lander, S. Lincoln, and M. Daly, Whitehead Institute, MIT.

YAC Library Screening. Screening of both the Washington University and CEPH libraries were performed by PCR essentially as previously described. Green, E.D. et al., *PNAS (USA)* 87:1213 (1990). Primer sequences for cosmid 43F6 at the T3 end were GGTTAAATTGACTGAAGGCACC and ATGCATCCAAACTCGGGATA, set forth in SEQ. ID NOs. 11 and 12, respectively; and the PCR conditions were 94° C. for 4 min for initial denaturation, 35 cycles of 94° C. for 1 min, 60° C. for 1 min, and 72° C. for 2 min, and then a 10 min final extension at 72° C. Primer sequences for cosmid 46C7 at the T7 end were TTTGCGGCCGGAACCGAC and GCTCCGGATCCCTAGAGAAA, set forth in SEQ. ID NOs. 13 and 14, respectively. The PCR conditions were the same as that for 43F6 except the annealing temperature was 57° C. instead of 60° C. PCR reactions were conducted in 20 μl of 10 mM Tris pH 8.3, 50 mM KCl, 1.5 mM MgCl$_2$, 0.01% gelatin, 2 mM DTT, 0.1 mM dNTP, 200 ng of each primer, and 1 unit of Taq polymerase. YAC DNA isolation was performed as previously described. Chandrasekharappa, S. C. et al., "Analysis of Yeast Artificial Chromosome Clones," in Burmeister M, Ulanovsky L (eds), *Meth. Mol. Bio.* (The Humana Press Inc., NJ) 12:235 (1992)

PFGE, Southern Blotting, Filter Hybridization. PFGE: DNA samples in agarose plugs were digested for 4–6 hr with restriction enzymes as previously described (Claxton, D. F. et al., *Blood* 80:582 (1992)) using the manufacturer's recommended buffers. After digestion, plugs were loaded into gels and electrophoresed for 18 hr in a transverse alternating field electrophoresis ("TAFE") apparatus (Beckman) according to the manufacturer's recommended protocol. Electrophoresis switch time was 1 min and power was set to 280 mA. Gels were stained with ethidium bromide and photographed prior to treatment in 0.25N HCl for 7 min. Following Southern transfer, nylon membranes were hybridized with DNA fragments labelled by random priming to >10$^9$ CPM/μg using Quick-Hyb buffer (Amersham) at 65° C. for 2 hr. Final washing was 0.1×SSC and 0.1% SDS at 60°–65° C. for 20 min. Autoradiography was carried out for 1–14 days at −70° C.

Fluorescence in Situ Hybridization. Human DNA was amplified out of interspecific hybrid cell DNA by inter-Alu-PCR using dual, bi-direction, consensus Alu primers and conditions as previously described. Lui, P. et al., *Can. Gen. Cytogen.* 65:93 (1993). Human DNA was prepared from YACs in the same way except that the temperature of annealing was reduced to 55° C., and DNA from cosmids was used directly. The DNAs were prepared for FISH by biotin-labeling and then competitively hybridized with human low-C$_0$t DNA to block nonspecific repetitive DNA. Lichter, P. et al., *PNAS (USA)* 87:6634 (1990). FISH reagents were obtained from ONCOR (Gaithersburg, Md.) and were used according to the instructions supplied by the manufacturer. Probe was detected by avidin-fluorescein following in situ hybridization onto human metaphase preparations. Lui, P. et al., *Can. Gen. Cytogen.* 65:93 (1993); Pinkel, D. et al., *PNAS (USA)* 83:2934 (1986) and Dolf, G. et al., *Genes Chrom. Can.* 3:48 (1991). Two color FISH was conducted as previously described. Kallioniemi O-P. et al., *PNAS (USA)* 89:5321 (1992). Briefly, DNA from cosmid 45G5 was labeled with biotin and detected with Texas red-avidin while DNA from cosmid 35B11 was labeled with digoxigenin and detected with fluoscein conjugated anti-digoxigenin. All slides were counterstained with propidium iodide/antifade and photographed under UVL epi-illumination using a multiple pass filter.

SPECIFIC EXAMPLE 2

CLONING OF P AND Q ARM BREAKPOINTS AND IDENTIFICATION OF TWO GENES DISRUPTED BY INVERSION

Figure 4A:
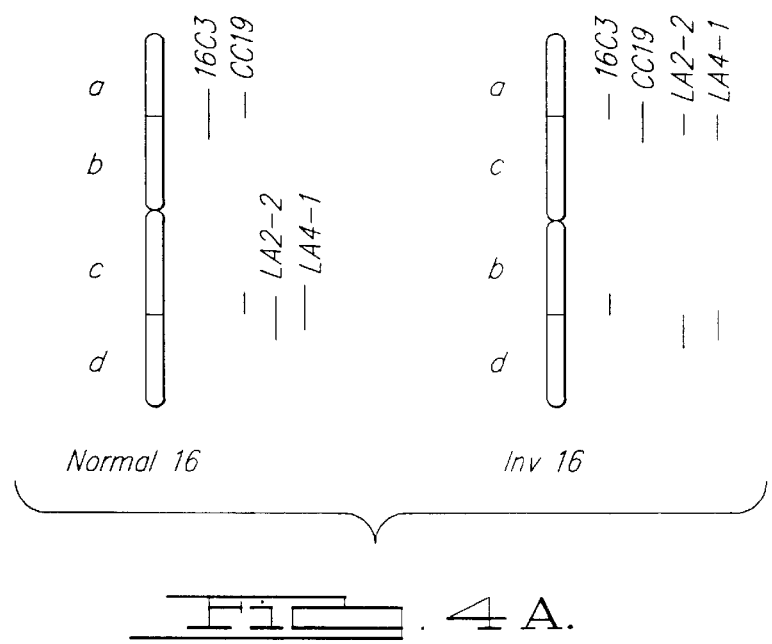
FIGS. 4A and 4B are schematic representations of the cosmids spanning the inv(16) breakpoints.
Figure 4B:
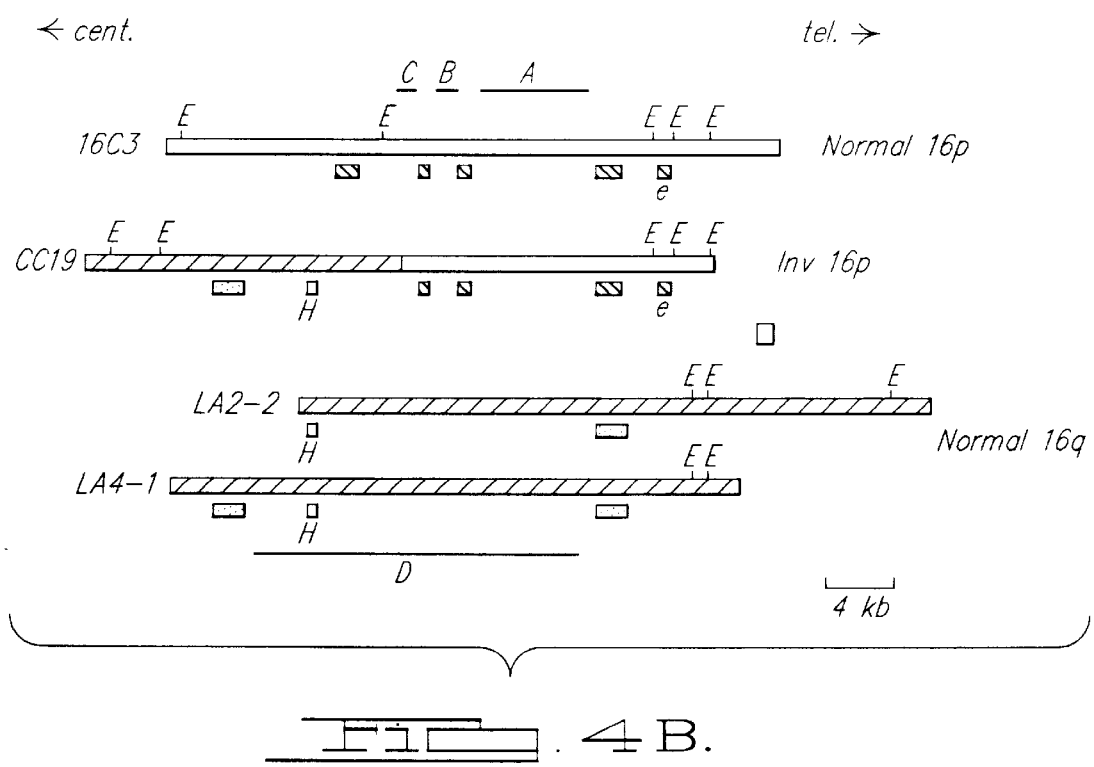

For reference, a schematic representation of the locations of the cosmids on normal and inverted chromosome 16s and a restriction map of cosmids 16C3, CC19, LA2-2 and LA4-1 is set forth in FIGS. 4A and 4B, respectively. In FIG. 4A, unfilled horizontal bars represent sequence from the p arm and shaded horizontal bars are sequence from the q arm. Solid boxes are probable exon locations for MYH11 and dotted boxes are probable exon locations for CBFB (the solid boxes with an e designate the location of 16C3e). The open boxes labeled with "H" refer to the repeat-free 0.7 kb HindII fragment used to identify LA2-2 and LA4-1. Horizontal lines labeled with letters A–D indicate intervals containing p and q arm breakpoints. The p arm breakpoints in the cell line ME-1 and three patients, are located in the A region, one patient each is located in regions B and C, and the q arm breakpoints in all six samples are located in region D. E, represents EcoRI. These Figures are further discussed below.

The Los Alamos chromosome 16 cosmid library was screened with the YACs described above in Specific Example 1 to isolate cosmids containing the p arm inversion breakpoint. Alu-PCR was conducted with DNA from YAC clones yB80B9, y854E2, y757D7, and yC8E1 2 and the 35B11 cosmid contig and the PCR products were separated by agarose gel electrophoresis. Liu, P. et al., *Can. Genet. Cytogen.* 65:93 (1993) The PCR products in common in yB80B9, y854E2, y757D7 (these three YAC clones contain the p arm breakpoint), but not present in yC8E1 2 and the cosmid contig (which do not contain the p arm breakpoint), were excised from the gel. The DNA was purified from the agarose and used as probe to screen the chromosome 16 cosmid library. Positive clones were picked and further studied. Cosmid clones so isolated were used as probes for FISH as described herein.

Figure 6:
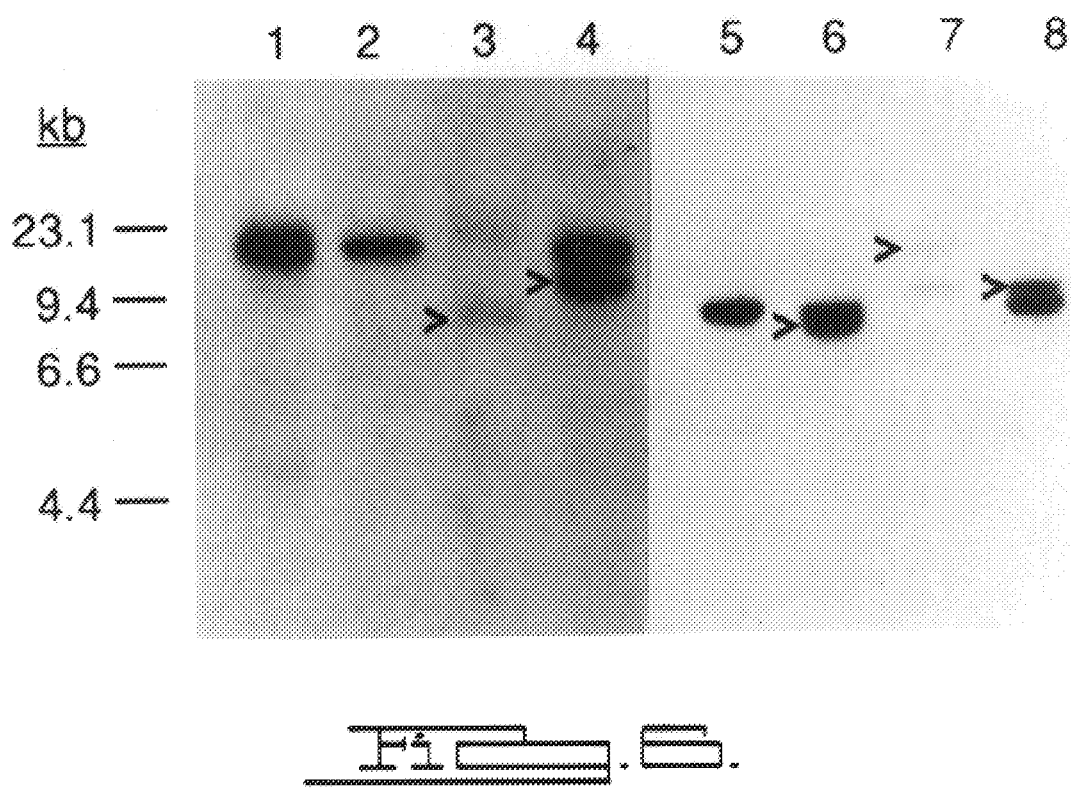
FIG. 6 is an autoradiograph of a Southern blot hybridized to $^{32}$P-labelled 16C3e DNA.

Cosmid 16C3 was used as a probe on a metaphase from the inv(16) cell line ME-1. While 16C3 generated single, discrete fluorescent signals on 16p from normal lymphoblastoid cells, one signal was detected on each arm of the inv(16) from the cell line ME-1, indicating that the 16p breakpoint lies within this cosmid. This finding was confirmed using peripheral leukemic cells from three additional patients known to have inv(16). Moreover, using a 1.2 kb EcoRI repeat-free fragment from cosmid 16C3 (designated 16C3e) as a probe, rearranged fragments were detected by Southern blot hybridization in multiple patients with several restriction endonucleases. FIG. 6C is an autoradiograph of the Southern blot hybridization with $^{32}$P-labeled 16C3e DNA. In FIG. 6, lanes 1 and 5 show DNA from a normal human fibroblast cell line; lanes 2 and 6 show DNA from inv(16) patient A, lanes 3 and 7 show DNA from inv(16) patient B; and, lanes 4 and 8 show DNA from the inv(16) cell line ME-1. DNA in lanes 1–4 was digested with HindIII and DNA in lanes 5–8 was digested with KpnI. Abnormal bands in patient sample lanes are indicated by arrowheads. The DNA in lanes 3 and 7 is under-loaded, resulting in the apparent slower migration of the hybridized bands. Southern blot hybridizations were performed as described herein.

As shown in FIG. 6, Southern blot hybridization against a human chromosome 16 regional assignment hybrid panel (Callen, D. F. et al., *Genomics* 4:348 (1989) and Chen, L. Z. et al., *Genomics* 10:308 1991)), 16C3e was assigned to 16p13.12-p13.13, between the breakpoints of hybrids CY19 and CY185, the same interval where the inv(16) p arm breakpoint was mapped in previous studies and herein. Callen, D. F. et al., *Am. J. Hum. Genet.* 51:A57 (1992); Wessels, J. W. et al., *Blood* 77:1555 (1991); Dauwerse, J. G., *Blood* 79:1299 (1992). As shown in FIG. 4B, a restriction map of the cosmid was generated. The inv(16) breakpoints in 5 patients were deduced based on the hybridization pattern of patient genomic DNA with 16C3e.

Figure 5A:
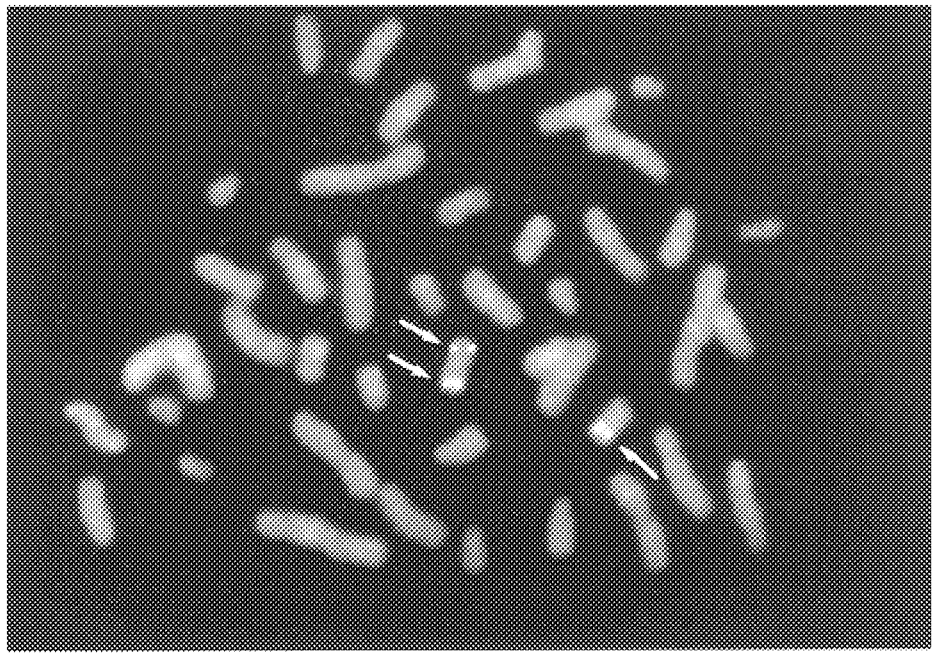
FIGS. 5A to 5C are FISH photomicrographs with cosmids at the inv(16) breakpoint.
Figure 5B:
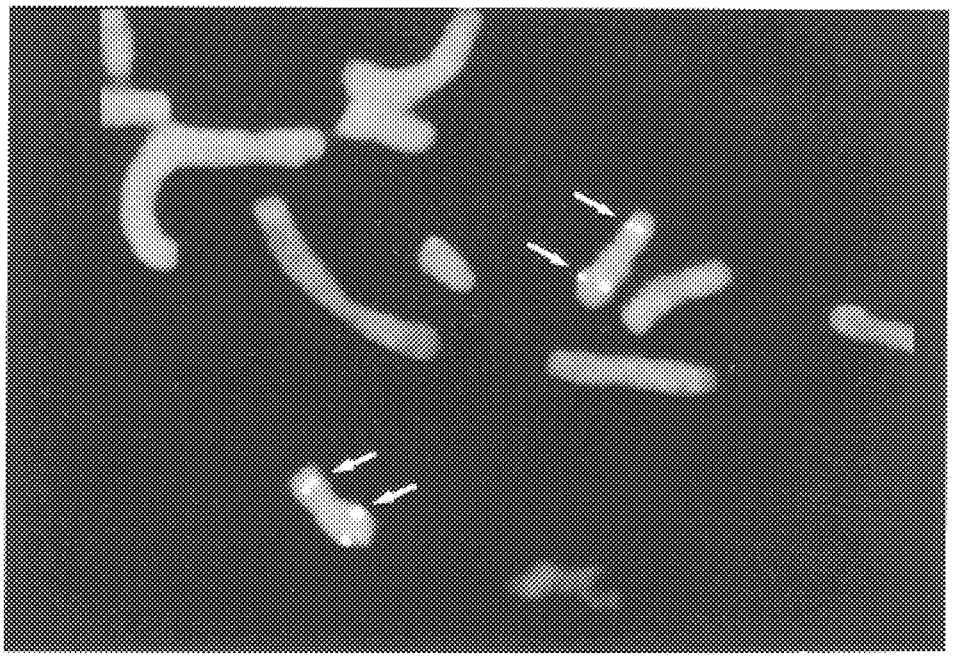

A cosmid library was constructed from the genomic DNA of peripheral leukemia cells of a patient with known inv(16). The genomic DNA from the leukemia cells of an inv(16) patient was partially digested with MboI to an average size of 40 kb and the ends filled in with dGTP and dATP. The sCOS vector was modified by inserting an XhoI linker at the BamHI site. Evans, G. A. et al., *Gene* 10 79:9 (1989). The vector was digested with XhoI and XbaI and the ends were filled in with dTTP and dCTP. The digested genomic DNA and the vector were then ligated and packaged using a commercial packaging kit (Gigapack Gold, Stratagene). The phage particles containing cosmid DNA were transducted into *E. coli* A490 cells. This library was screened with 16C3e and several cosmid clones were isolated. As shown in FIG. 5B, using these cosmids as FISH probes revealed that at least one of them, CC19, contained the fusion genomic DNA sequence: CC19 generated split signals on both chromosome 16s from normal metaphases.

Restriction mapping of CC19 showed that it contained additional restriction fragments not found in 16C3 (FIG. 4B). One of these fragments, a single copy 0.7 kb HindIII fragment from CC19, was used to hybridize to the chromosome 16 hybrid panel mentioned above. This probe was assigned to 16q13-q22.1, between hybrids CY7 and CY6, which is consistent with the assignment of the inv(16) q arm breakpoint in previous studies. Callen, D. F. et al., *Am. J. Hum. Genet.* 51 :A57 (1992); Wessels, J. W. et al., *Blood* 77:1555 (1991); Dauwerse, J. G., *Blood* 79:1299 (1992).

Figure 5C:
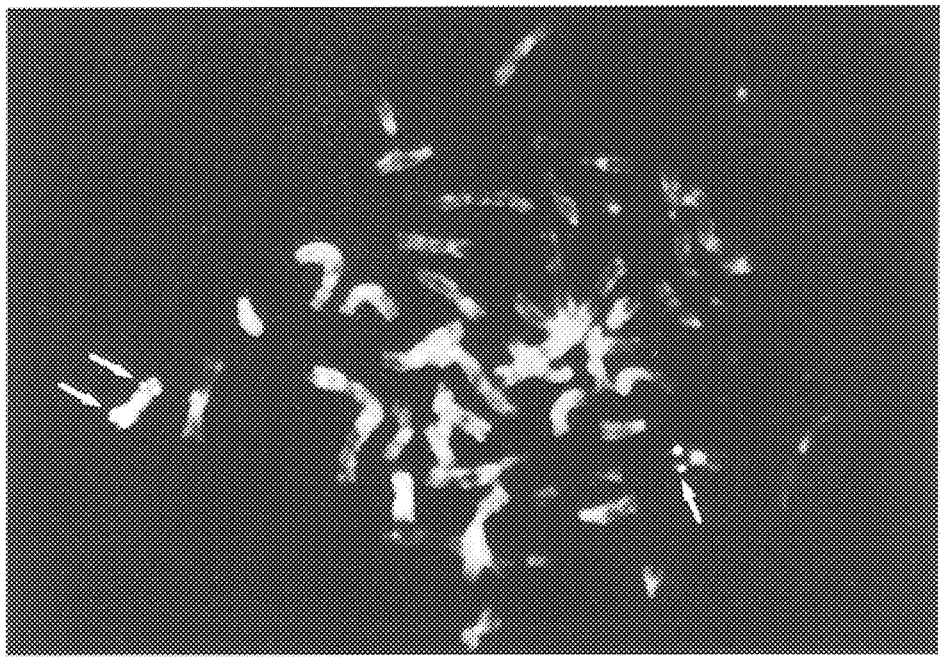

To clone the q arm breakpoint region, this 0.7 kb HindIII fragment from cosmid CC19 was used to screen Los Alamos chromosome 16 cosmid library. Two overlapping cosmid clones, LA2-2 and LA4-1, were identified. Both of them were shown to contain the q arm breakpoint of inv(16) when used as FISH probes, they produced single signal on the q arm of the normal chromosome and a signal on both arms of the inverted chromosome (FIGS. 4A and 5C).

To identify genes affected by the inversion, single copy fragments and whole cosmid DNA from cosmids 16C3, CC19, and LA2-2 were used to screen cDNA libraries. Screening of a human fetal brain cDNA library (from Stratagene) with 16C3e or the entire 16C3 cosmid identified two related cDNA clones, FB3A and FB7A. Sequencing of the cDNA clones showed that they contain partial sequences of a non-muscle myosin heavy chain gene (NMMHC, or MYH9 according to Human Gene Mapping nomenclature) previously isolated and assigned to chromosome 22. Saez, C. G. et al., *PNAS (USA)* 87:1164 (1990) and Toothaker, L. E. et al., *Blood* 78:1826 (1991). Besides additional MYH9 cDNA clones, no cDNAs were identified with 16C3e or 16C3 from this human fetal brain cDNA library or human bone marrow cDNA library.

Sequencing of 16C3e, the 1.2 kb EcoRI fragment of 16C3, identified a 108 bp sequence 72% identical to the human MYH9 mentioned above, indicating that FB3A and FB7A were cloned by cross-hybridization. This 108 bp sequence was 90% identical to the rabbit smooth muscle myosin heavy chain (SMMHC) gene (Nagai, R. et al., *J. Biol Chem.* 264:9734 (1989)), 87% identical to rat SMMHC (Babij, P. et al., *J. Mol. Biol.* 210:673 (1989)), and 77% identical to the chicken SMMHC gene. Yanagisawa, M. et al., *J. Mol. Biol.* 198:143 (1987). This 108 bp segment contained an open reading frame flanked by conserved 5' and 3' splicing signals, suggesting that it was an exon of the human homologue of the rabbit and rat SMMHC genes. Gene-specific PCR primers were designed to amplify from the locus on chromosome 16 and not the one on chromosome 22 (data not shown). Using these primers, the chromosome 16 SMMHC gene was shown to be expressed in ME-1 cells in a reverse transcription-PCR (RT-PCR) experiment (data not shown). Therefore, it appears that a human smooth muscle myosin heavy chain gene has been identified which is located in the p arm breakpoint region of inv(16).

A human large intestine cDNA library was screened with 16C3e. One of the isolated cDNA clones (named L11a, with an insert 1.8 kb long) contained identical sequence to the exon described above for 16C3e. Hybridization with L11a against cosmid 16C3 DNA revealed that there were exons on both sides of the inv(16) breakpoints, indicating that this SMMHc gene is disrupted by the inversion (FIG. 4B).

Matsuoka et al., have reported the cloning of a human SMMHC gene, MYH11. Matsuoka, R. et al., *Am. J. Med. Genet.* 46:61 (1993). The sequence of this gene is identical to that of L11a for 1.8 kb except for a few nucleotide differences (<0.3%) which are most likely due to sequencing errors (L11a contains a sequence corresponding to nt1579-3364 of that reported by Matsuoka et al. and the exon of 16C3e is nt 2847-2955). By correlating hybridization intensity and gene dosage on Southern blot and FISH, Matsuoka et al. regionally assigned MYH11 to 16q12. From the results described herein it is concluded that the location of MYH11 on chromosome 16 is actually in the region 16p13.13, spanning the p arm breakpoint of inv(16).

To identify the q arm component of the postulated fusion gene, the same human fetal brain cDNA library used to isolate FB3A and FB7a was screened with whole cosmid DNA or single copy fragments of LA2-2 and LA4-1. Three cDNA clones (FB3d, FB4d, and FBI 2c) were identified. Sequencing of the cDNA clones and GenBank search revealed high sequence homology to a newly described mouse DNA-binding factor CBFβ (Wang, S. et al., *Mol. Cell. Biol.* 13:3324 (1993)); FB12c contained most of the coding sequence and part of the 3' untranslated region, and FB3d and FB4d contained sequences in the 3' untranslated region. Screening of a HeLa expression cDNA library (Peterson, C. et al., *Gene* 107:279 (1991)) with FB12c identified a near full-length cDNA clone, named RL9a. This sequence, shown in SEQ ID NOs: 7 and 9 starts from the second codon of the mouse CBFβ/PEBP2β gene. The first 75 nucleotides were derived from sequencing of an RT-PCR product generated from RNA of inv(16)-positive leukemic cells using a primer in the 5' untranslated region of mouse CBFβ and primer M1 (see FIG. 7A and discussion below). The rest of the sequence was from the RL9a cDNA clone. There is an Alu-like sequence in the 3' untranslated region. Sequencing was performed as described herein.

The sequence homology of RL9a to mouse CBFβ at DNA level is more than 90% in the coding region and more than 70% in the 3' untranslated region. At the protein level, only three amino acid changes were identified out of the total of 181. Therefore, RL9a contains the gene coding for the human counterpart of the mouse CBFβ. This human gene is designated CBFB. The nucleic and amino acid sequences for CBFB are set forth in Sequence Listing IDs 7 and 8, respectively; the nucleic and amino acid sequences for the coding region alone are shown in Sequence Listing IDs 9 and 10, respectively. The GenBank accession numbers for partial human CBFβB cDNA sequence is L20298.

When FB12C was used to probe patient genomic DNA, rearranged bands were detected. Mapping on cosmids showed that the breakpoint in the inv(16) patient whose DNA was used to make the cosmid library falls in an intron of CBFB (FIG. 4B).

Since both CBFβB on the q arm and MYH11 on the p arm are disrupted by the inversion, a fusion transcript could potentially be made by splicing the exons of the two genes together on the inversion chromosome. Two fusions are possible, one containing 5' portion of the CBFB gene and the 3' portion of the MYH11; the other composed of the MYH11 5' region and CBFB 3' region. The former fusion is undoubtedly more important for leukemogenesis since in two AMML M4Eo patients with inv(16) there is an associated deletion centromeric to the p arm breakpoint, which would truncate the 5' portion of MYH11.

Figure 7A:
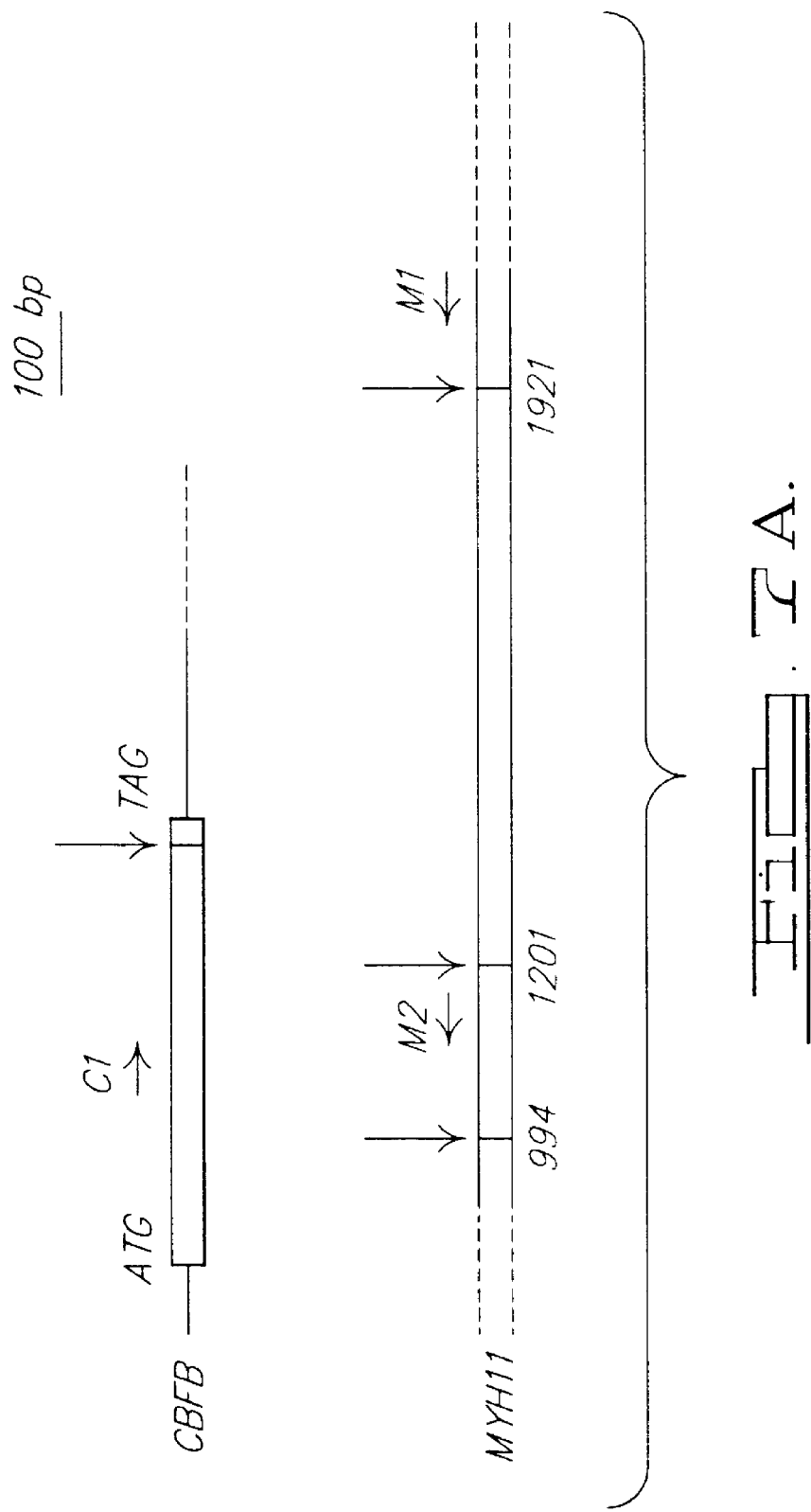
FIG. 7A is a diagram showing the locations in the CBFB and MYH11 genes of the primers C1, M1 and M2, which were used in PCR assays to detect the CBFB and MYH11 fusion products characteristic of inv(16).
Figure 7B:
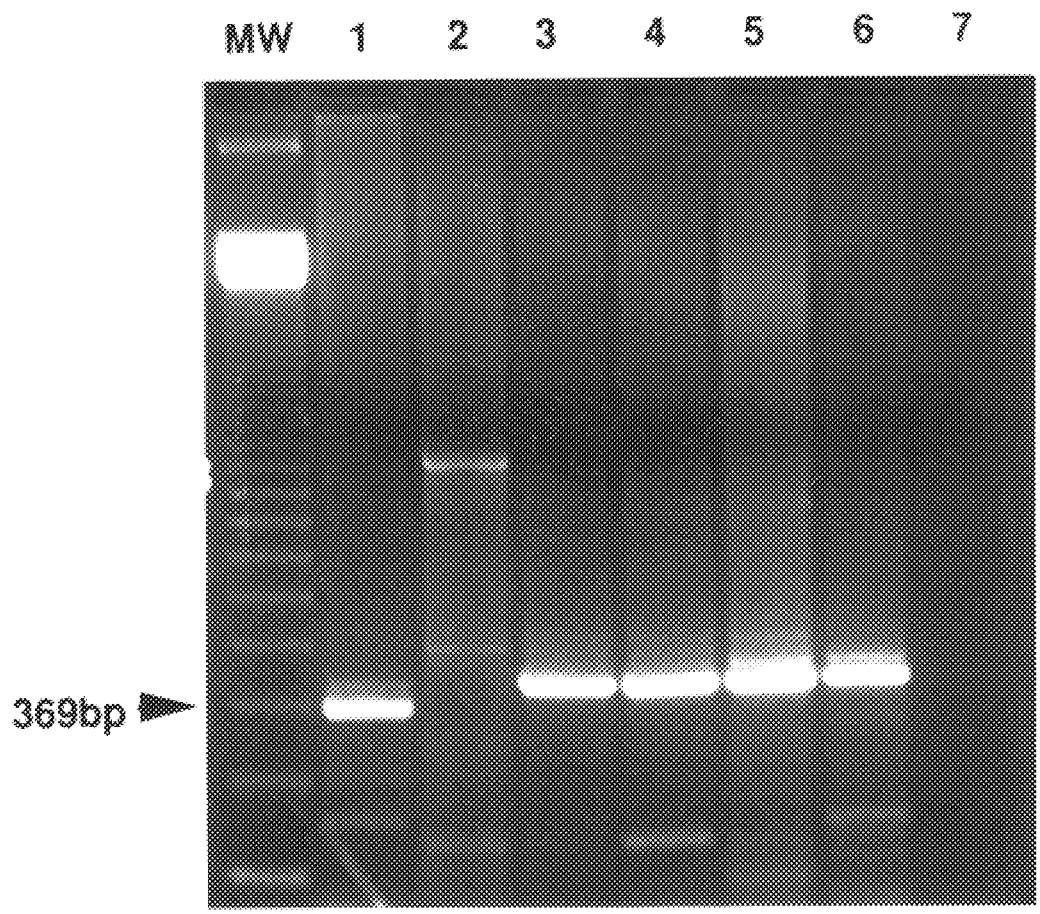
FIG. 7B is a photograph of ethidium bromide-stained agarose gel separating RT-PCR products.

Primers were designed from the middle of the CBFB coding sequence and the 3' region of MYH11. FIG. 7A is a diagram showing the locations of primer CBFB in the CBFB gene and M1 and M2 in the MYH11 gene. The sequences of the primers are: C1 (sense primer), 5' GCAGGCAAGG-TATATTTGAAGG 3' (nt 271 to 292 of CBFB, SEQ ID NOs: 7 and 9); M1 (antisense primer 1), 5' CTCTTCTCCTCAT-TCTGCTC 3' (complementary to nt 667 to 686 of SEQ ID NO: 1; reverse sequence of nt2095-21 14 of MYH11 (Matsuoka, R. et al., *Am. J. Med. Genet.* 46:61 (1993)); M2 (antisense primer 2), 5' ACTGCAGCTCCTGCACCTGC 3' (complementary to nt 618 to 637 of SEQ ID NO: 3; reverse sequence of nt 1119-1138 of MYH11). Matsuoka, R. et al., *Am. J. Med. Genet.* 46:61 (1993). The locations of the discontinuities in patient RNA are indicated with vertical arrows in FIG. 7A. RT-PCR was conducted using total cellular RNA from the cell line ME-1 and peripheral leukemia cells of 5 patients with inv(16). PCR products were generated in all 6 samples using different combinations of CBFB and MYH11 primers. FIG. 7B is a photograph of an ethidium bromide-stained agarose gel separating the RT-PCR products. Lanes 1–5 in FIG. 7B show products of RT-PCR using RNA from peripheral leukemic cells of 5 inv(16) patients; lane 6 shows RT-PCR products generated from RNA from the cell line ME-1; and, lane 7 is RT-PCR with no template. Primers C1 and M1 were used for reactions in lanes 2–7 and primers C1 and M2 were used for lane 1. RNA was isolated from cells using RNAzol (CINNA/BIOTECX, Friendswood, Tex). RT-PCR was performed as described. Liu, P. et al., *Somat. Cell Mol. Genet.* 18:7 (1992). PCR products were separated on an LMP agarose gel (NuSieve GTG; FMC, Rockland, Me.), excised from the gel under long wavelength UV light, and used directly for sequencing with the Sequenase kit (USB, Cleveland, Ohio). Sequencing of the PCR products confirmed that they are in-frame fusion gene transcripts derived from CBFB and MYH11. The CBFB breakpoint in all 6 samples is the same, located close to the 3' end of the coding region with only the last 17 of the 182 aa of the potential CBFβ protein deleted (see SEQ ID NOs: 1–10). Interestingly, this CBFB breakpoint is located at a sequence which serves as an alternative splice donor in both mouse and human. Wang, S. et al., *Mol. Cell. Biol.* 13:3324 (1993) and studies described herein.

Three different breakpoints in the MYH11 coding region were identified in the six patients. The cell line ME-1 and the three patients shared the same breakpoint (see FIG. 7B, lanes 3–6), whereas two other patients have their breakpoints at 927 bp and 720 bp upstream from the first one respectively (FIG. 7B, lanes 1 and 2). All of these rearrangements maintain the reading frame of the fusion transcript. Primers designed to amplify the potential reciprocal fusion transcript were used in RT-PCR with RNA from three inv(16) samples. No PCR products were generated (data not shown).

By analogy to the molecular events revealed in other leukemias, it is likely that the fusion of CBFB and MYH11 produces a protein which contributes to leukemogenesis. Moreover, this fusion protein must have a dominant effect since only one of the two chromosome 16s is inverted in leukemic cells. The mouse CBFβ gene has been cloned and analyzed recently. Wang, S. et al., *Mol. Cell. Biol.* 13:3324 (1993); Speck, N. A. et al., *Mol. Cell. Biol.* 7:1101 (1987); Redondo, J. M. et al., *Mol Cell. Biol.* 12:4817 (1992); Speck, N. A. et al., *Genes Dev.* 4:233 (1990) and Wang, S. et al., *Mol. Cel. Biol.* 12:89 (1992). CBF, or core-binding factor, binds to the core site of murine leukemia virus and also to the enhancers of the T cell receptor genes. Speck, N. A. et al., *Mol. Cell. Biol* 7:1101 (1987); Redondo, J. M. et al., *Mol.Cell. Biol.* 12:4817 (1992). The core site appears to be a major genetic determinant of the tissue specificity of leukemias induced by the murine leukemia virus. Speck, N. A. et al., *Genes Dev.* 4:233 (1990). Affinity-purified CBF contains at least two subunits, CBFα and CBFβ. Wang, S. et al., *Mol. Cell. Biol.* 13:3324 (1993) and Wang, S. et al., *Mol. Cell. Biol.* 12:89 (1992). CBFα has been shown to be identical to AML1, the gene found to be disrupted in the characteristic t(8;21) translocation in the M2 subtype of AML. Wang, S. et al., *Mol. Cell. Biol.* 13:3324 (1993). Another DNA-binding factor, named PEBP2, which binds to similar core sequences in the enhancer of the polyomavirus has been identified in NIH3T3 cells. Kamachi, Y. et al., *J. Virol* 64:4808 (1990) Ogawa, E. et al., *Virol.* 194:314 (1993); Bae, S. C. et al., *Oncogene* 8:809 (1993) PEBP2 contains two subunits, PEBP2α and PEBP2β. Two α subunits have been identified, one is identical to CBFα (Bae, S. C. et al., *Oncogene* 8:809 (1993)).

PEBP2β and CBFβ, however, are identical. Wang, S. et al., *Mol. Cell. Biol.* 13:3324 (1993) and Ogawa, E. et al., *Virol.* 194:314 (1993).

SPECIFIC EXAMPLE 3

DIAGNOSTIC APPLICATIONS

The inv(16) fusion gene of the present invention can be used to determine the presence or absence of chromosome 16 abnormalities in leukemic cells. The present invention utilizes PCR and DNA probes such as YACs, cosmids and plasmids to identify inv(16) in leukemic cells. PCR offers the most sensitive and rapid detection of the presence of these abnormalities. Furthermore, it is less affected by the quality of the samples than chromosome preparation-based methods such as karyotyping and FISH, and can detect leukemic cells present in a very small percentage of the cell population. Therefore, PCR may also be the best method for follow-up monitoring of the disease as well as for diagnosis. YACs and cosmids may also be used as probes for FISH as an alternative diagnosis tool. Since YACs and cosmids of the present invention contain the breakpoints of the inversion and translocation, the diagnosis is more specific. Also, in some rare atypical cases where PCR is negative, the YAC probe may still detect the abnormality since YAC clones cover a large region of the chromosome. Plasmids containing DNA from the breakpoint region are also used as probes to detect the chromosome abnormalities by Southern blot hybridization.

PCR. RNA is isolated from cells. Reverse transcription is performed using the RNA to generate cDNA. PCR is then performed using the cDNA and primers specific for the detection of the chromosome 16 rearrangements. The PCR products are separated by agarose gel electrophoresis and visualized by UV light after ethidium bromide staining.

FISH Using YACs and Cosmids as Probes. YAC and cosmid DNA are labeled with biotin. Metaphase chromosomes are prepared from patient cells. The biotin-labeled probes are hybridized to the chromosome and the location of hybridization on the chromosomes are detected using fluorescence-tagged avidin and antibodies.

Southern Blot Hybridization. DNA is isolated from patient cells, digested with restriction endonucleases, separated by electrophoresis and transferred to nylon membranes. The patient DNA on the nylon membrane is then probed with radioisotope-labeled plasmids and any abnormal fragments of DNA are detected by autoradiography.

Assay Kits. Diagnostic assays and assay kits are also contemplated within the scope of the present invention. One embodiment of an assay kit comprises a container, nucleic acid probes specific for the inv(16) inversion and/or the CBF and MYH11 genes, and/or antibodies raised to the inversion gene product and/or FISH probes specific for inv(6) DNA or CBF and MYH11 DNA, and various reagents known to those skilled in the art required to perform diagnostic assays such as those described above in this Specific Example.

Another embodiment comprises oligonucleotide primers specific for regions of CBFB and MYH11 which allow PCR amplification of the inversion 16 gene product in patients with AMML (M4, inv(16)). Also included in this embodiment would be DNAs positive and negative for inversion 16, which would serve as positive and negative controls, respectively.

The teachings of the publications referenced herein are incorporated by reference.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

---

We claim:

1. An isolated and purified nucleic acid molecule having a nucleotide sequence chosen from the group consisting of SEQ ID NOs. 1, 3, 5, 7 and 9.

2. An isolated and purified nucleic acid probe having a nucleotide sequence which specifically hybridizes to the sequence of claim 1.

3. An isolated and purified transcript of the nucleic acid molecule of claim 1.

4. A first and second primer, wherein the first primer is a purified nucleic acid having a nucleotide sequence as set forth by nucleotides 271 to 292 of SEQ ID NO. 7, and the second primer is a purified nucleic acid having a nucleotide sequence which hybridizes under high stringency conditions to a nucleotide sequence as set forth by nucleotides 687 to 686 of SEQ ID NO. 1.

5. A first and second primer, wherein the first primer is a purified nucleic acid having a nucleotide sequence as set forth by nucleotides 271 to 292 of SEQ ID NO. 7, and the second primer is a purified nucleic acid having a nucleotide sequence which hybridizes under high stringency conditions to a nucleotide sequence as set forth by nucleotides 618 to 637 of SEQ ID NO. 3.

6. An isolated and purified nucleic acid probe having a nucleotide sequence that specifically hybridizes to the complementary sequence of a sequence chosen from the group consisting of SEQ ID Nos. 1, 3, 5, 7 and 9.

7. The nucleic acid molecule of claim 1, wherein the nucleotide sequence is SEQ ID No. 1.

8. The nucleic acid molecule of claim 1, wherein the nucleotide sequence is SEQ ID No. 3.

9. The nucleic acid molecule of claim 1, wherein the nucleotide sequence is SEQ ID No. 5.

10. The nucleic acid molecule of claim 1, wherein the nucleotide sequence is SEQ ID No. 7.

11. The nucleic acid molecule of claim 1, wherein the nucleotide sequence is SEQ ID No. 9.

12. The nucleic acid molecule of claim 1, wherein thymine is replaced with uracil.

13. The nucleic acid molecule of claim 6, wherein the sequence is SEQ ID No. 1.

14. The nucleic acid molecule of claim 6, wherein the sequence is SEQ ID No. 3.

15. The nucleic acid molecule of claim 6, wherein the sequence is SEQ ID No. 5.

16. The nucleic acid molecule of claim 6, wherein the sequence is SEQ ID No. 7.

17. The nucleic acid molecule of claim 6, wherein the sequence is SEQ ID No. 9.

18. An isolated and purified nucleic acid molecule having a nucleotide sequence that encodes an amino acid sequence chosen from the group consisting of SEQ ID Nos. 2, 4, 6, 8 and 10.

19. The nucleic acid molecule of claim 18, wherein the nucleotide sequence encodes the amino acid sequence of SEQ ID No. 2.

20. The nucleic acid molecule of claim 18, wherein the nucleotide sequence encodes the amino acid sequence of SEQ ID No. 4.

21. The nucleic acid molecule of claim 18, wherein the nucleotide sequence encodes the amino acid sequence of SEQ ID No. 6.

22. The nucleic acid molecule of claim 18, wherein the nucleotide sequence encodes the amino acid sequence of SEQ ID No. 8.

23. The nucleic acid molecule of claim 18, wherein the nucleotide sequence encodes the amino acid sequence of SEQ ID No. 10.

24. An isolated and purified DNA fragment comprising contiguous nucleotides on the 5' and 3' sides of the fused site of HCBFB-MYH11 fused DNA, the fused site being the site between bases 492 and 493 of the nucleotide sequence of SEQ ID No. 1, wherein said DNA fragment specifically hybridizes with the nucleotide sequence of SEQ ID No. 1, but does not specifically hybridize with HCBFB DNA or MYH11 DNA.

25. An isolated and purified DNA fragment comprising contiguous nucleotides on the 5' and 3' sides of the fused site of HCBFB-MYH11 fused DNA, the fused site being the site between bases 492 and 493 of the nucleotide sequence of SEQ ID No. 3, wherein said DNA fragment specifically hybridizes with the nucleotide sequence of SEQ ID No. 3, but does not specifically hybridize with HCBFB DNA or MYH11 DNA.

26. An isolated and purified DNA fragment comprising contiguous nucleotides on the 5' and 3' sides of the fused site of HCBFB-MYH11 fused DNA, the fused site being the site between bases 492 and 493 of the nucleotide sequence of SEQ ID No. 5, wherein the DNA fragment specifically hybridizes with the nucleotide sequence of SEQ ID No. 5, but does not specifically hybridize with HCBFB DNA or MYH11 DNA.

27. A probe which is HCBFB-MYH11 fused DNA comprising the contiguous nucleotide sequence of SEQ ID No. 1 or which is a DNA fragment comprising contiguous nucleotides on the 5' and 3' sides of the fused site of HCBFB-MYH11 fused DNA, the fused site being the site between bases 492 and 493 of the nucleotide sequence of SEQ ID No. 1, wherein the DNA fragment specifically hybridizes with the nucleotide sequence of SEQ ID No. 1, but does not specifically hybridize with HCBFB DNA or MYH11 DNA.

28. A method for detecting fused DNA containing the fused site of HCBFB-MYH11 fused DNA, the fused site being the site between bases 492 and 493 of the nucleotide sequence of SEQ ID No. 1, comprising the steps of:
   a) contacting the probe of claim 27 with a sample to be tested; and
   b) determining whether the probe specifically hybridizes with the fused DNA in the sample but not with HCBFB DNA or MYH11 DNA.

29. A probe which is HCBFB-MYH11 fused DNA comprising the contiguous nucleotide sequence of SEQ ID No. 3 or which is a DNA fragment comprising contiguous nucleotides on the 5' and 3' sides of the fused site of HCBFB-MYH11 fused DNA, the said fused site being the site between bases 492 and 493 of the nucleotide sequence of SEQ ID No. 3, wherein the DNA fragment specifically hybridizes with the nucleotide sequence of SEQ ID No. 3, but does not specifically hybridize with HCBFB DNA or MYH11 DNA.

30. A method for detecting fused DNA containing the fused site of HCBFB-MYH11 fused DNA, the fused site being the site between bases 492 and 493 of the nucleotide sequence of SEQ ID No. 3, comprising the steps of:
   a) contacting the probe of claim 29 with a sample to be tested; and
   b) determining whether the probe specifically hybridizes with the fused DNA in the sample but not with HCBFB DNA or MYH11 DNA.

31. A probe which is HCBFB-MYH11 fused DNA comprising the contiguous nucleotide sequence of SEQ ID No. 5 or which is a DNA fragment comprising contiguous nucleotides on the 5' and 3' sides of the fused site of HCBFB-MYH11 fused DNA, the fused site being the site between bases 492 and 493 of the nucleotide sequence of SEQ ID No. 5, wherein the DNA fragment specifically hybridizes with the nucleotide sequence of SEQ ID No. 5, but does not specifically hybridize with HCBFB DNA or MYH11 DNA.

32. A method for detecting fused DNA containing the fused site of HCBFB-MYH11 fused DNA, said fused site being the site between bases 492 and 493 of the nucleotide sequence of SEQ ID No. 5, comprising the steps of:
   a) contacting the probe of claim 31 with a sample to be tested; and
   b) determining whether the probe specifically hybridizes with the fused DNA in the sample but not with HCBFB DNA or MYH11 DNA.

33. A pair of oligonucleotides wherein one of the oligonucleotides specifically hybridizes with HCBFB-MYH11 fused DNA comprising the contiguous nucleotide sequence of SEQ ID No. 1 on the 3' side of a fused site which is the site between bases 492 and 493 of SEQ ID No. 1 and the other of the oligonucleotides specifically hybridizes with the HCBFB-MYH11 fused DNA on the 5' side of said fused site.

34. A pair of oligonucleotides wherein one of the oligonucleotides specifically hybridizes with HCBFB-MYH11 fused DNA comprising the contiguous nucleotide sequence of SEQ ID No. 3 on the 3' side of a fused site which is the site between bases 492 and 493 of SEQ ID No. 3 and the other of the oligonucleotides specifically hybridizes with the HCBFB-MYH11 fused DNA on the 5' side of the fused site.

35. A pair of oligonucleotides wherein one of the oligonucleotides specifically hybridizes with HCBFB-MYH11 fused DNA comprising the contiguous nucleotide sequence of SEQ ID No. 5 on the 3' side of a fused site which is the site between bases 492 and 493 of SEQ ID No. 5 and the other of the oligonucleotides specifically hybridizes with the HCBFB-MYH11 fused DNA on the 5' side of the fused site.

* * * * *

UNITED STATES PATENT AND TRADEMARK OFFICE
CERTIFICATE OF CORRECTION

PATENT NO. : 5,837,457
DATED : November 17, 1998
INVENTOR(S) : Pu Liu et al

Page 1 of 5

It is certified that error appears in the above-identified patent and that said Letters Patent is hereby corrected as shown below:

On page 2 of the Title Page under Other Publications, Col. 2, line 29, "Caller" should be --Callen--.

On the Title Page under Publications, Col. 2, line 5, "Inv(6)" should be --Inv(16)--.

On the Title Page under Publications, Col. 2, line 6, "Closing" should be --Cloning--.

On the Title Page under Publications, Col. 2, line 14, "Syntheny" should be --Synteny--.

On page 2 of the Title Page under Other Publications, Col. 1, line 13, delete "P. et al.," (second occurrence).

On page 2 of the Title Page under Other Publications, Col. 1, line 14, "of" (first occurrence) should be --for--.

On page 2 of the Title Page under Other Publications, Col. 1, line 30, "Drosophjila" should be --Drosophila--.

On page 2 of the Title Page under Other Publications, Col. 2, lines 16,17, "Enhancers" should be --Enhancer--.

On page 2 of the Title Page under Other Publications, Col. 2, line 23, "Heary" should be --Heavy--.

UNITED STATES PATENT AND TRADEMARK OFFICE
CERTIFICATE OF CORRECTION

PATENT NO. : 5,837,457
DATED : November 17, 1998
INVENTOR(S) : Pu Liu et al

It is certified that error appears in the above-identified patent and that said Letters Patent is hereby corrected as shown below:

Column 1 between lines 7 and 9 (required under 37 C.F.R. §401.14(f)(4)) to include the following:

--SPONSORSHIP

Work on this invention was sponsored in part by National Institute of Health Grant No. DK028164. The Government has certain rights in the invention.--.

Column 2, line 9, after "(1991)" insert --.--.

Column 2, line 29, "arrangement" should be --rearrangement--.

Column 3, line 64, "hybridzaing" should be --hybridizing--.

Column 5, line 3, "form" should be --from--.

Column 6, line 16, "a" should be --$\alpha$--.

Column 7, line 3, "PEBP2ß" should be --PEPB2$\alpha$--.

Column 7, line 15, "a" (second occurrence) should be --$\alpha$--.

Column 7, line 54, "Lui" should be --Liu--.

UNITED STATES PATENT AND TRADEMARK OFFICE
CERTIFICATE OF CORRECTION

PATENT NO. : 5,837,457
DATED : November 17, 1998
INVENTOR(S) : Pu Liu et al

Page 3 of 5

It is certified that error appears in the above-identified patent and that said Letters Patent is hereby corrected as shown below:

Column 8, line 23, "ERCCR" should be --ERCC4--.

Column 8, line 26, "the" (second occurrence) should be --a--.

Column 8, line 44, "inv( 16)" should be --inv(16)--.

Column 9, line 11, "1-2" should be --1.2--.

Column 9, line 37, "lone" should be --(one--.

Column 10, line 11, "21" should be --2I--.

Column 10, line 19, "yC8E1 2" should be --yC8E12--.

Column 10, line 19, "metaphese" should be --metaphase--.

Column 11, line 67, "Lui" should be --Liu--.

Column 12, line 12, "Lui" should be --Liu--.

Column 12, line 19, "fluoscein" should be --fluorescein--.

Column 12, line 32, "4A" (second occurrence) should be --4B--.

UNITED STATES PATENT AND TRADEMARK OFFICE
CERTIFICATE OF CORRECTION

PATENT NO. : 5,837,457

DATED : November 17, 1998            Page 4 of 5

INVENTOR(S) : Pu Liu et al

It is certified that error appears in the above-identified patent and that said Letters Patent is hereby corrected as shown below:

Column 12, line 39, "HindII" should be --HindIII--.

Column 12, line 51, "yC8E1 2" should be --yC8E12--.

Column 12, line 54, after "(1993)" insert --.--.

Column 12, line 56, "yC8E1 2" should be --yC8E12--.

Column 13, line 7, "6C" should be --6--.

Column 13, line 19, delete "As shown in FIG. 6,".

Column 13, line 38, delete "10".

Column 14, line 43, "SMMHc" should be --SMMHC--.

Column 14, line 61, "FBI 2c" should be --FBI2c--.

Column 15, line 24, "CBFßB" should be --CBFB--.

Column 15, line 30, "CBFßB" should be --CBFB--.

Column 15, line 43, "CBFB" (first occurrence) should be --C1--.

UNITED STATES PATENT AND TRADEMARK OFFICE
CERTIFICATE OF CORRECTION

PATENT NO. : 5,837,457
DATED : November 17, 1998
INVENTOR(S) : Pu Liu et al

Page 5 of 5

It is certified that error appears in the above-identified patent and that said Letters Patent is hereby corrected as shown below:

Column 15, line 49, "21 14" should be --2114--.

Column 16, line 55, after "(1990)" insert --;--.

Column 16, line 56, after "(1993)" insert --.--. ($2^{nd}$ occurrence)

Column 18, line 12, "inv( 6)" should be --inv(16)--.

Column 57, line 40, Claim 4, "687" should be --667--.

Signed and Sealed this

Twentieth Day of February, 2001

Attest:

NICHOLAS P. GODICI

Attesting Officer

Acting Director of the United States Patent and Trademark Office